US010604581B2

(12) United States Patent
Marasco et al.

(10) Patent No.: US 10,604,581 B2
(45) Date of Patent: Mar. 31, 2020

(54) HUMAN MONOCLONAL ANTI-PD-L1 ANTIBODIES AND METHODS OF USE

(71) Applicant: Dana-Farber Cancer Institute, Inc., Boston, MA (US)

(72) Inventors: Wayne A. Marasco, Wellesley, MA (US); Jianhua Sui, Waltham, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 45 days.

(21) Appl. No.: 15/821,087

(22) Filed: Nov. 22, 2017

(65) Prior Publication Data

US 2018/0346587 A1 Dec. 6, 2018

Related U.S. Application Data

(62) Division of application No. 14/433,826, filed as application No. PCT/US2013/063509 on Oct. 4, 2013, now Pat. No. 9,828,434.

(60) Provisional application No. 61/779,969, filed on Mar. 13, 2013, provisional application No. 61/709,731, filed on Oct. 4, 2012.

(51) Int. Cl.
| | |
|---|---|
| *C07K 16/30* | (2006.01) |
| *C07K 16/40* | (2006.01) |
| *C07K 16/20* | (2006.01) |
| *C07K 16/00* | (2006.01) |
| *C07K 16/28* | (2006.01) |
| *C07K 16/24* | (2006.01) |
| *C07K 16/46* | (2006.01) |

(52) U.S. Cl.
CPC ........ *C07K 16/2896* (2013.01); *C07K 16/244* (2013.01); *C07K 16/2803* (2013.01); *C07K 16/2827* (2013.01); *C07K 16/30* (2013.01); *C07K 16/3076* (2013.01); *C07K 16/40* (2013.01); *C07K 16/468* (2013.01); *C07K 2317/21* (2013.01); *C07K 2317/31* (2013.01); *C07K 2317/33* (2013.01); *C07K 2317/526* (2013.01); *C07K 2317/53* (2013.01); *C07K 2317/565* (2013.01); *C07K 2317/622* (2013.01); *C07K 2317/73* (2013.01); *C07K 2317/732* (2013.01); *C07K 2317/734* (2013.01); *C07K 2317/76* (2013.01); *C07K 2317/92* (2013.01)

(58) Field of Classification Search
CPC ........ C07K 16/00; C07K 16/20; C07K 16/30; C07K 16/40
USPC .......................................... 424/133.1, 142.2
See application file for complete search history.

(56) References Cited

U.S. PATENT DOCUMENTS

| | | | |
|---|---|---|---|
| 3,773,919 A | 11/1973 | Boswell et al. | |
| 4,485,045 A | 11/1984 | Regen | |
| 4,522,811 A | 6/1985 | Eppstein et al. | |
| 4,544,545 A | 10/1985 | Ryan et al. | |
| 4,676,980 A | 6/1987 | Segal et al. | |
| 4,816,567 A | 3/1989 | Cabilly et al. | |
| 4,946,778 A | 8/1990 | Ladner et al. | |
| 5,013,556 A | 5/1991 | Woodle et al. | |
| 5,030,719 A | 7/1991 | Umemoto et al. | |
| 5,091,513 A | 2/1992 | Huston et al. | |
| 5,132,405 A | 7/1992 | Huston et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 5,916,771 A | 6/1999 | Hori et al. | |
| 5,939,598 A | 8/1999 | Kucherlapati et al. | |
| 2009/0055944 A1 | 2/2009 | Korman et al. | |
| 2011/0209230 A1 | 8/2011 | Korman et al. | |
| 2016/0176962 A1 | 6/2016 | Murriel | |
| 2016/0256527 A1 | 9/2016 | Gurney | |
| 2016/0311903 A1 | 10/2016 | West | |
| 2017/0304444 A1* | 10/2017 | Marasco | .......... A61K 39/39558 |
| 2017/0362297 A1* | 12/2017 | Marasco | .............. C07K 14/705 |

FOREIGN PATENT DOCUMENTS

| | | |
|---|---|---|
| CN | 101104640 A | 1/2008 |
| CN | 101248089 A | 8/2008 |
| CN | 101663323 A | 3/2010 |
| CN | 102264762 A | 11/2011 |
| EP | 2003089 A2 | 12/2008 |
| WO | WO1991/000360 | 1/1991 |
| WO | WO92/20373 | 11/1992 |
| WO | WO1994/002602 | 2/1994 |
| WO | WO1994/011026 | 5/1994 |
| WO | WO1995/022618 | 8/1995 |

(Continued)

OTHER PUBLICATIONS

Faiena et al. (Journal for ImmunoTherapy of Cancer, (Nov. 2018) vol. 6, Supp. Supplement 1. Abstract No. P47; Meeting Info: 33rd Annual Meeting and Pre-Conference Programs of theSociety for Immunotherapy of Cancer, SITC 2018. Washington, DC, United States. Nov. 7, 2018-Nov. 11, 2018).*

(Continued)

*Primary Examiner* — Lynn A Bristol
(74) *Attorney, Agent, or Firm* — Baker Donelson

(57) ABSTRACT

The present invention comprises human monoclonal antibodies that bind to PD-L1 (also known as programmed death ligand 1 or B7H1). Binding of the invented antibody to PD-L1 inhibits binding to its receptor, PD1 (programmed death 1), and ligand-mediated activities and can be used to treat cancer and chronic viral infections.

15 Claims, 9 Drawing Sheets
Specification includes a Sequence Listing.

(56) References Cited

FOREIGN PATENT DOCUMENTS

| | | |
|---|---|---|
| WO | WO1996/033735 | 10/1996 |
| WO | WO1996/034096 | 10/1996 |
| WO | WO1999/053049 | 10/1999 |
| WO | WO2010/036959 A2 | 4/2010 |
| WO | WO2011/066389 A1 | 6/2011 |

OTHER PUBLICATIONS

Kammerer-Jacquet, et al. (International Journal of Cancer (2017), 140(1), 142-148).*

Pinato et al. (OncoImmunology (2017), 6(11), e1358332/1-e1358332/8).*

Pinato, et al. (Journal of Clinical Oncology, (Jun. 20, 2017) vol. 35, No. 15, Supp. Supplement 1; Meeting Info: 2017 Annual Meeting of the American Society of Clinical Oncology, ASCO. Chicago, IL, United States. Jun. 2, 2017-Jun. 6, 2017).*

Pinato, et al. (Journal of Clinical Oncology, (May 2016) vol. 34, Supp. Supplement 15. Abstract No. e15658; Meeting Info: 2016 Annual Meeting of the American Society of Clinical Oncology, ASCO 2016. Chicago, IL, United States. Jun. 3, 2016-Jun. 7, 2016).*

Combe et al. (Oncoimmunology, (May 2015) vol. 4, No. 5, pp. e1001236. Electronic Publication Date: Mar. 19, 2015.*

Barbas C. et al., "Recombinant human Fab fragments neutralize human type 1 immunodeficiency virus in vitro", *Proc. Natl. Acad. Sci. USA*, vol. 89, pp. 9339-9343, (Oct. 1992).

Zebedee S. et al., "Human combinatorial antibody libraries to hepatitis B surface antigen", *Proc. Natl. Acad. Sci. USA*, vol. 89, pp. 3175-3179, (1992).

Malmqvist M., "Biospecific interaction analysis using biosensor technology", *Nature*, vol. 361, pp. 186-187 (1993).

Davies D. et al., "Antibody-Antigen Complexes[1]" *Annual Review of Biochemistry*, vol. 59, pp. 439-473, (1990).

Wilkinson D., "Immunochemical techniques inspire development of new antibody purification methods", *The Scientist*, vol. 14, No. 8, pp. 25-28, (Apr. 17, 2000).

Köhler G. et al., "Continuous cultures of fused cells secreting antibody of predefined specificity", *Nature*, vol. 256, pp. 495-497 (Aug. 7, 1975).

Coding J., "Monoclonal Antibodies: Principles and Practice", *Academic Press*, pp. 59-103, (1986).

Kozbor D. et al., "A Human Hybrid Myeloma for Production of Human Monoclonal Antibodies", *The Journal of Immunology*, vol. 133, No. 6, pp. 3001-3005, (Dec. 1984).

Brodeur B. et al., "Mouse-Human Myeloma Partners for the Production of Heterohybridomas", *Monoclonal Antibody Production Techniques and Applications*, Marcel Dekker, Inc., New York, pp. 51-63, (1987).

Munson P. et al., "Ligand: A Versatile Computerized Approach for Characterization of Ligand-Binding Systems", *Analytical Biochemistry*, vol. 107, pp. 220-239, (1980).

Morrison P. et al., Success in specification, *Nature*, vol. 368, pp. 812-813 (Apr. 28, 1994).

Kozbor D. et al., "The production of monoclonal antibodies from human lymphocytes", *Immunology Today*, vol. 4, No. 3, pp. 72-79, (1983).

Cole, et al.,"The EBV-Hybridoma Technique and its application to human lung cancer", *Monoclonal Antibodies and Cancer Therapy*, pp. 77-96, (1985).

Cote R. et al., "Generation of human monoclonal antibodies reactive with cellular antigens", *Proc. Natl. Acad. Sci. USA*, vol. 80, pp. 2026-2030, (Apr. 1983).

Hoogenboom H. et al., "By-passing immunization. Human Antibodies from Synthetic Repertoires of Germline $V_H$ Gene Segments Rearranged in Vitro", *Journal of Molecular Biology*, vol. 227, pp. 381-388, (1992).

Marks J. et al., "By-passing immunization. Human Antibodies from V-gene Libraries Displayed on Phage", *Journal of Molecular Biology*, vol. 222, pp. 581-597, (1991).

Marks et al., "By-passing immunization: Building High Affinity Human Antibodies by Chain Shuffling", *Bio/Technology*, vol. 10, 779-783 (Jul. 1992).

Huston et al., "Protein engineering of antibody binding sites: Recovery of specific activity in an anti-digoxin single-chain Fv analogue produced in *Escherichia coli*", *Proc Nat Acad Sci USA*, vol. 85, No. 16, pp. 5879-5883, (1988).

Lonberg N. et al., "Antigen-specific human antibodies from mice comprising four distinct genetic modifications", *Nature*, vol. 368, pp. 856-859, (1994).

Fishwild D. et al., "High-avidity human IgGk monoclonal antibodies from a novel strain of minilocus transgenic mice", *Nature Biotechnology*, vol. 14, pp. 845-851, (1996).

Neuberger M., "Generating high-avidity human Mabs in mice", *Nature Biotechnology*, vol. 14, p. 826, (1996).

Lonberg et al., "Human Antibodies from Transgenic Mice", *Intern. Rev. Immunol*, vol. 13, pp. 65-93, (1995).

Geller, A. et al., "An HSV-1 Vector Expressing Tyrosine Hydroxylase Causes Production and Release of L-DOPA from Cultured Rat Striatal Cells", *Journal of Neurochemistry*, vol. 64, pp. 487-496 (1995).

Geller, A. et al., "Long-term increases in neurotransmitter release from neuronal cells expressing a constitutively active adenylate cyclase from a herpes simplex virus type 1 vector", *Proc Natl. Acad. Sci. USA*, vol. 90, pp. 7603-7607 (1993).

Geller, A. et al., "Infection of cultured central nervous system neurons with a defective herpes simplex virus 1 vector results in stable expression of *Escherichia coli* fi-galactosidase", *Proc Natl. Acad. Sci USA*, vol. 87, pp. 1149-1153, (1990).

Le Gal La Salle G. et al., "An Adenovirus Vector for Gene Transfer into Neurons and Glia in the Brain", *Science*, vol. 259, pp. 988-990, (1993).

Davidson B., et al., "A model system for in vivo gene transfer into the central nervous system using an adenoviral vector", *Nature Genetics*, vol. 3, pp. 219-223, (1993).

Yang Y. et al., "Cellular and Humoral Immune Responses to Viral Antigens Create Barriers to Lung-Directed Gene Therapy with Recombinant Adenoviruses", *Journal of Virology*, vol. 69, No. 4, pp. 2004-2015, (1995).

Kaplitt, M. et al., "Long-term gene expression and phenotypic correction using adeno-associated virus vectors in the mammalian brain", *Nature Genetics*, vol. 8, pp. 148-154 (1994).

Bobo et al., "Convection-enhanced delivery of macromolecules in the brain", *Proc. Natl. Acad. Sci. USA*, vol. 91, pp. 2076-2080 (1994).

Morrison P. et al., "High-flow microinfusion: tissue penetration and pharmacodynamics", *Am. J. Physiol.* 266, pp. 292-305, (1994).

Huse W. et al., "Generation of a Large Combinatorial Library of the Immunoglobulin Repertoire in Phage Lambda", *Science*, vol. 246, pp. 1275-1281, (1989).

Caron et al., "Engineered Humanized Dimeric Forms of IgG are More Effective Antibodies", *J. Exp. Med.*, vol. 176, pp. 1191-1195 (1992).

Shopes B., A Genetically Engineered Human IgG Mutant with Enhanced Cytolytic Activity[1], *The Journal of Immunology*, vol. 148, pp. 2918-2922, (1992).

Stevenson G. et al., "A chimeric antibody with dual Fc regions (bisFabFc) prepared by manipulations at the IgG hinge", *Anti-Cancer Drug Design*, 3, pp. 219-230 (1989).

Vitetta E. et al., "Redesigning Nature's Poisons to Create Anti-Tumor Reagents", *Science*, vol. 238, pp. 1098-1104 (1987).

Killen J. et al., "Specific Killing of Lymphocytes that Cause Experimental Autoimmune Myasthenia Gravis by Ricin Toxin-Acetyloholine Receptor Conjugates[1]", *The Journal of Immunology*, vol. 133, No. 5, pp. 2549-2553, (1984).

Jansen F. et al., "Immunotoxins: Hybrid Molecules Combining High Specificity and Potent Cytoxicity", *Immunological Reviews*, Vo. 62, pp. 185-216 (1982).

Ramakrishnan, S. et al., "Comparison of the Selective Cytotoxic Effects of Immunotoxins Containing Ricin A Chain or Pokeweed

(56) References Cited

OTHER PUBLICATIONS

Antiviral Protein and Anti-Thy 1.1 Monoclonal Antibodies[1]", *Cancer Research*, vol. 44, pp. 201-208 (1984).
Eppstein D. et al., "Biological activity of liposome-encapsulated murine interferon y is mediated by a cell membrane receptor", *Proc. Natl. Acad. Sci. USA*, vol. 82,pp. 3688-3692, (1985).
Hwang K. et al., "Hepatic uptake and degradation of unilamellar sphingomyelin/cholesterol liposomes: A kinetic study", *Proc. Natl Acad. Sci. USA*, vol. 77, No. 7, pp. 4030-4034 (1980).
Martin et al., "Irreversible Coupling of Immunoglobulin Fragments to Preformed Vesicles", *The Journal of Biological Chemistry*, vol. 257, No. 1, pp. 286-288 (1982).
Marasco W. et al., "Design, intracellular expression, and activity of a human anti-human immunodeficiency virus type 1 gp120 single-chain antibody", *Proc. Natl. Acad. Sci. USA*, vol. 90, pp. 7889-7893 (1993).
Ridgway J. et al., "Knobs-into-holes' engineering of antibody CH3 domains for heavy chain heterodimerization", *Protein Engineering*, vol. 9, No. 7, pp. 617-621 (1996).
Van der Neut Kolfschoten, M. et al., "Anti-Inflammatory Activity of Human IgG4 Antibodies by Dynamic Fab Arm Exchange", *Science*, vol. 317, pp. 1554-1557, (2007).
Labrijn, A. et al, "Species-Specific Determinants in the IgG CH3 Domain Enable Fab-Arm Exchange by Affecting the Noncovalent Interaction Strength", *Journal of Immunology*, vol. 187, pp. 3238-3246, (2011).
Sondergaard, H. et al., "IL-21: roles in immunopathology and cancer therapy", *Tissue Antigens*, vol. 74, pp. 467-479, (2009).
Kasaian, M. et al, "IL-21 Limits NK Cell Responses and Promotes Antigen-Specific T Cell Activation: A Mediator of the Transition from Innate to Adaptive Immunity", *Immunity*, vol. 16, 559-569, (2002).
Coquet, J. et al, "IL-21 IS Produced by NKT Cells and Modulates NKT Cell Activation and Cytokine Production[1]", *The Journal of Immunology*, vol. 178, pp. 2827-2834, (2007).
Li, Y. et al, "IL-21 Influences the Frequency, Phenotype, and Affinity of the Antigen-Specific CD8 T Cell Response[1]", *The Journal of Immunology*, vol. 175:2261-2269, (2005).
Schmidt, H. et al, "Safety and Clinical Effect of Subcutaneous Human Interleukin-21 in Patients with Metastatic Melanoma or Renal Cell Carcinoma: A Phase I Trial", *Clinical cancer Research*, vol. 16, No. 21, pp. 5312-5319, (2010).
Grünwald, V. et al, "A Phase I study of recombinant human interleukin-21 (rIL-21) in combination with sunitinib in patients with metastatic renal cell carcinoma (RCC)", *Acta Oncologica*, vol. 50:121-126, (2011).
Crotty, S. et al, Follicular Helper CD4 T Cells ($T_{FH}$), *Annual review of Immunology*, vol. 29, pp. 621-623, (2011).
Sakuishi, K. et al, "Targeting Tim-3 and PD-1 pathways to reverse T cell exhaustion and restore anti-tumor immunity", *The Journal of Experimental Medicine*, vol. 207, No. 10, pp. 2187-2194, (2010).
Zhang, Y. et al, "Tim-3 regulates pro- and anti-inflammatory cytokine expression in human CD14_monocytes", *Journal of Leukocyte Biology*, vol. 91, pp. 189-196, (2012).
Dardalhon, V. et al., "Tim-3/Galectin-9 Pathway: Regulation of Th1 Immunity through Promotion of CD11b+Ly-6G+ Myeloid Cells", *Journal of Leukocyte Biology*, vol. 185, pp. 1383-1392, (2012).
Lam K., "Application of combinatorial library methods in cancer research and drug discovery", *Anti-Cancer Drug Design*, vol. 12, pp. 145-167, (1997).
Brahmer, J. et al., "Safety and activity of anti-PD-L1 antibody in patients with advanced cancer", *The New England Journal of Medicine*, Massachusetts Medical Society, Boston, MA, US, vol. 366, No. 26, pp. 2455-2465, (2012).
Topalian S. et al., "Safety, activity, and immune correlates of anti-PD-1 antibody in cancer", *The New England Journal of Medicine*, vol. 366, No. 26, pp. 2443-2454, (2012).
International Search Report issued for PCT/US2013/063509 and dated Apr. 23, 2014.
Written Opinion issued for PCT/US2013/063509 and dated Apr. 23, 2014.
Seibutsu Butsuri, 2008, vol. 48, No. 5, p. 294-298.
Japanese Patent Application No. 2015-535829, Notice of Reasons for Rejection.
Karu, Alexander, Recombinant Antibody Technology, ILAR Journal, vol. 37, No. 3, pp. 132-141, 1995.
Suarez, E., et al., "Chimeric antigen receptor T cells secreting anti-PD-L1 antibodies more effectively regress renal cell carcinoma in a humanized mouse model," *Oncotarget*, vol. 7, No. 23: 34341-34355, (2016).

* cited by examiner

Figure 1

HUMAN MONOCLONAL ANTI-PD-L1 ANTIBODIES AND METHODS OF USE

RELATED APPLICATIONS

This application is a divisional application of U.S. patent application Ser. No. 14/433,826, filed Apr. 6, 2015, which is a National Stage of International Patent Application No. PCT/US2013/063509, filed Oct. 4, 2013, which claims priority to and benefit of U.S. Provisional Application No. 61/709,731, filed on Oct. 4, 2012, and U.S. Provisional Application No. 61/779,969 filed on Mar. 13, 2013; the contents of which are each hereby incorporated by reference in their entireties.

FIELD OF THE INVENTION

This invention relates generally to anti-PD-L1 (also known as programmed cell death 1 ligand 1 or B7H1) antibodies as well as to methods for use thereof.

INCORPORATION-BY-REFERENCE OF SEQUENCE LISTING

The contents of the text file named "DFCI-068_D01US_ST25.txt", which was created on Oct. 6, 2016 and is 71 kilobytes in size, are hereby incorporated by reference in their entirety.

BACKGROUND OF THE INVENTION

The immune system must achieve a balance between effective responses to eliminate pathogenic entities and maintaining tolerance to prevent autoimmune disease. T cells are central to preserving this balance, and their proper regulation is primarily coordinated by the B7-CD28 family of molecules. Interactions between B7 family members, which function as ligands, and CD28 family members, which function as receptors, provide critical positive signals that not only initiate, augment and sustain T cell responses, but also contribute key negative signals that limit, terminate and/or attenuate T cell responses when appropriate. A member of the CD28 family, called PD-1 (also known as programmed cell death-1) is upregulated on activated T cells, B cells, and monocytes. PD-1 has two identified ligands in the B7 family, PD-L1 (also known as BH71 or programmed cell death-1 ligand 1) and PD-L2. While PD-L2 expression tends to be more restricted, found primarily on activated antigen-presenting cells (APCs), PD-L1 expression is more widespread, including cells of hematopoietic lineage (including activated T cells, B cells, monocytes, dendritic cells and macrophages) and peripheral nonlymphoid tissues (including heart, skeletal, muscle, placenta, lung, kidney and liver tissues). The widespread expression of PD-L1 suggests its significant role in regulating PD-1/PD-L1-mediated peripheral tolerance.

Binding between PD-L1 and PD-1 has a profound effect on the regulation of T cell responses. Specifically, PD-L1/PD-1 interaction inhibits T cell proliferation and production of effector cytokines that mediate T cell activity and immune response, such as IL-2 and IFN-γ. This negative regulatory function is important for preventing T cell-mediated autoimmunity and immunopathology. However, the PD-1/PD-L1 axis has also been shown to play a role in T cell exhaustion, whereby the negative regulatory function inhibits T cell response to the detriment of the host. Prolonged or chronic antigenic stimulation of T cells can induce negative immunological feedback mechanisms which inhibit antigen-specific responses and results in immune evasion of pathogens. T cell exhaustion can also result in progressive physical deletion of the antigen-specific T cells themselves. T cell expression of PD-1 is up-regulated during chronic antigen stimulation, and its binding to PD-L1 results in a blockade of effector function in both CD4+ (T helper cells) and CD8+ (cytotoxic T lymphocytes or CTL) T cells, thus implicating the PD-1/PD-L1 interaction in the induction of T cell exhaustion.

More recently, it has been shown that some chronic viral infections and cancers have developed immune evasion tactics that specifically exploit the PD-1/PD-L1 axis by causing PD-1/PD-L1-mediated T cell exhaustion. Many human tumor cells and tumor-associated antigen presenting cells express high levels of PD-L1, which suggests that the tumors induce T cell exhaustion to evade anti-tumor immune responses. During chronic HIV infection, HIV-specific CD8+ T cells are functionally impaired, showing a reduced capacity to produce cytokines and effector molecules as well as a diminished ability to proliferate. Studies have shown that PD-1 is highly expressed on HIV-specific CD8+ T cells of HIV infected individuals, indicating that blocking the PD-1/PD-L1 pathway may have therapeutic potential for treatment of HIV infection and AIDS patients. Taken together, agents that block the PD-1/PD-L1 pathway will provide a new therapeutic approach for a variety of cancers, HIV infection, and/or other diseases and conditions that are associated with T-cell exhaustion. Therefore, there exists an urgent need for agents that can block or prevent PD-1/PD-L1 interaction.

SUMMARY OF THE INVENTION

The invention is based upon the discovery of monoclonal antibodies which bind PD-L1. The monoclonal antibody is fully human. The antibodies bind PD-L1. The antibodies are referred to herein as huPD-L1 antibodies.

PD-L1 is also known as programmed cell death 1 ligand 1, programmed death ligand 1, PDCD1 ligand 1, PDCD1L1, PDL1, B7 homolog 1, B7H1, B7-H, CD274 and CD274 antigen.

The present invention provides an isolated humanized monoclonal antibody having a heavy chain with three CDRs comprising the amino acid sequences SYGIS (SEQ ID NO:57), WISAYNGNTNYAQKLED (SEQ ID NO:70), and ALPSGTILVGGWFDP (SEQ ID NO:86) respectively and a light chain with three CDRs comprising the amino acid sequences TRSSGNIASNYVQ (SEQ ID NO:101), EDNQRPS (SEQ ID NO:115), and QSYDSSNLWV (SEQ ID NO:127) respectively; a heavy chain with three CDRs comprising the amino acid sequences SYALS (SEQ ID NO:58), AISGGGGSTYYADSVKD (SEQ ID NO:71), and DVFPETFSMNYGMDV (SEQ ID NO:87) respectively and a light chain with three CDRs comprising the amino acid sequences QGDSLRSYYAS (SEQ ID NO:102), GKNNRPS (SEQ ID NO:116), and NSRDSSGNHYV (SEQ ID NO:128) respectively; a heavy chain with three CDRs comprising the amino acid sequences DYAMH (SEQ ID NO:60), LISGDGGSTYYADSVKD (SEQ ID NO:73), and VLLPCSSTSCYGSVGAFDI (SEQ ID NO:88) respectively and a light chain with three CDRs comprising the amino acid sequences GGSDIGRKSVH (SEQ ID NO:103), SDRDRPS (SEQ ID NO:117), and QVWDNNSDHYV (SEQ ID NO:129) respectively; a heavy chain with three CDRs comprising the amino acid sequences NYDMS (SEQ ID NO:61), RVNWNGGSTTYADAVKD (SEQ ID NO:74), and EFVGAYDL (SEQ ID NO:89) respectively and a light chain with three CDRs comprising the amino acid sequences TGTSSDVGGYNYVS (SEQ ID NO:104), DVSNRPS (SEQ ID NO:118), and SSYTSSTLP (SEQ ID NO:130) respectively; a heavy chain with three CDRs comprising the amino acid sequences GLYIH (SEQ ID NO:62), WIIPIFG-TANYAQKFED (SEQ ID NO:75), and GLRWGIWG-WFDP (SEQ ID NO:90) respectively and a light chain with three CDRs comprising the amino acid sequences RASQ-SIGNSLA (SEQ ID NO:105), GASSRAT (SEQ ID NO:119), and QQHTIPTFS (SEQ ID NO:131) respectively; a heavy chain with three CDRs comprising the amino acid sequences DNAIS (SEQ ID NO:63), WIIPIFGKP-NYAQKFED (SEQ ID NO:76), and TMVRGFLGVMDV (SEQ ID NO:91) respectively and a light chain with three CDRs comprising the amino acid sequences RASQGIG-SYLA (SEQ ID NO:106), AASTLQS (SEQ ID NO:120), and QQLNNYPIT (SEQ ID NO:132) respectively; a heavy chain with three CDRs comprising the amino acid sequences SYAMS (SEQ ID NO:64), AISGSGGSTYYADSVKD (SEQ ID NO:77), and DQFVTIFGVPRYGMDV (SEQ ID NO:92) respectively and a light chain with three CDRs comprising the amino acid sequences SGDKLGNKYAY (SEQ ID NO:107), QDIKRPS (SEQ ID NO:121), and QTWDNSVV (SEQ ID NO:133) respectively; a heavy chain with three CDRs comprising the amino acid sequences SYAIS (SEQ ID NO:57), WIIPIFGTANYAQKFED (SEQ ID NO:78), and GRQMFGAGIDF (SEQ ID NO:93) respectively and a light chain with three CDRs comprising the amino acid sequences TRSSGSIDSNYVQ (SEQ ID NO:108), EDNQRPS (SEQ ID NO:115), and QSYDSN-NRHVI (SEQ ID NO:134) respectively; a heavy chain with three CDRs comprising the amino acid sequences TYALN (SEQ ID NO:65), RIVPLIGLVNYAHNFED (SEQ ID NO:79), and EVYGGNSDY (SEQ ID NO:94) respectively and a light chain with three CDRs comprising the amino acid sequences TRSSGNIGTNYVQ (SEQ ID NO:109), EDYR-RPS (SEQ ID NO:122), and QSYHSSGWE (SEQ ID NO:135) respectively; a heavy chain with three CDRs comprising the amino acid sequences SHGIT (SEQ ID NO:66), WISAHNGHASNAQKVED (SEQ ID NO:80), and VHAALYYGMDV (SEQ ID NO:95) respectively and a light chain with three CDRs comprising the amino acid sequences GGNNIGSKGVH (SEQ ID NO:110), DDSDRPS (SEQ ID NO:123), and QVWDSSSDHWV (SEQ ID NO:136) respectively; a heavy chain with three CDRs comprising the amino acid sequences RHGMH (SEQ ID NO:67), VISHDGSVKYYADSMKD (SEQ ID NO:81), and GLSYQVSGWFDP (SEQ ID NO:96) respectively and a light chain with three CDRs comprising the amino acid sequences TRSSGSIASNYVQ (SEQ ID NO:111), EDN-QRPS (SEQ ID NO:115), and QSYDSTTPSV (SEQ ID NO:137) respectively; a heavy chain with three CDRs comprising the amino acid sequences SYGIS (SEQ ID NO:58), WTSPHNGLTAFAQILED (SEQ ID NO:82), and VHPVFSYALDV (SEQ ID NO:97) respectively and a light chain with three CDRs comprising the amino acid sequences TRSSGSIASNYVQ (SEQ ID NO:112), EDNQRPS (SEQ ID NO:115), and QSYDGITVI (SEQ ID NO:138) respectively; a heavy chain with three CDRs comprising the amino acid sequences TYAFS (SEQ ID NO:68), RIIPILGIAN-YAQKFED (SEQ ID NO:83), and DGYGSDPVL (SEQ ID NO:98) respectively and a light chain with three CDRs comprising the amino acid sequences TRSSGSIASHYVQ (SEQ ID NO:113), EDNKRPS (SEQ ID NO:124), and QSYDSSNRWV (SEQ ID NO:139) respectively; or a heavy chain with three CDRs comprising the amino acid sequences NYGIS (SEQ ID NO:69), WISAYNGNTNYAQKVED (SEQ ID NO:84), and GDFRKPFDY (SEQ ID NO:99) respectively and a light chain with three CDRs comprising the amino acid sequences TLRSGLNVGSYRIY (SEQ ID NO:114), YKSDSNKQQAS (SEQ ID NO:125), and MIWYSSAVV (SEQ ID NO:140) respectively; wherein said antibody binds human PD-L1.

In one aspect, the antibody is monovalent or bivalent. In another aspect, the antibody is a single chain antibody.

The present invention provides a single chain antibody comprising a $V_H$ nucleotide sequence comprising SEQ ID NO: 1 and a $V_L$ nucleotide sequence comprising SEQ ID NO: 3; a $V_H$ nucleotide sequence comprising SEQ ID NO: 5 and a $V_L$ nucleotide sequence comprising SEQ ID NO:7; a $V_H$ nucleotide sequence comprising SEQ ID NO: 9 and a $V_L$ nucleotide sequence comprising SEQ ID NO: 11; a $V_H$ nucleotide sequence comprising SEQ ID NO: 13 and a $V_L$ nucleotide sequence comprising SEQ ID NO: 15; a $V_H$ nucleotide sequence comprising SEQ ID NO: 17 and a $V_L$ nucleotide sequence comprising SEQ ID NO:19; a $V_H$ nucleotide sequence comprising SEQ ID NO: 21 and a $V_L$ nucleotide sequence comprising SEQ ID NO:23; a $V_H$ nucleotide sequence comprising SEQ ID NO: 25 and a $V_L$ nucleotide sequence comprising SEQ ID NO:27; a $V_H$ nucleotide sequence comprising SEQ ID NO: 29 and a $V_L$ nucleotide sequence comprising SEQ ID NO:31; a $V_H$ nucleotide sequence comprising SEQ ID NO: 33 and a $V_L$ nucleotide sequence comprising SEQ ID NO:35; a $V_H$ nucleotide sequence comprising SEQ ID NO: 37 and a $V_L$ nucleotide sequence comprising SEQ ID NO:39; a $V_H$ nucleotide sequence comprising SEQ ID NO: 41 and a $V_L$ nucleotide sequence comprising SEQ ID NO:43; a $V_H$ nucleotide sequence comprising SEQ ID NO: 45 and a $V_L$ nucleotide sequence comprising SEQ ID NO:47; a $V_H$ nucleotide sequence comprising SEQ ID NO: 49 and a $V_L$ nucleotide sequence comprising SEQ ID NO:51; or a $V_H$ nucleotide sequence comprising SEQ ID NO: 53 and a $V_L$ nucleotide sequence comprising SEQ ID NO:55.

In another aspect, the present invention provides a single chain antibody comprising a $V_H$ amino acid sequence comprising SEQ ID NO: 2 and a $V_L$ amino acid sequence comprising SEQ ID NO: 4; a $V_H$ amino acid sequence comprising SEQ ID NO: 6 and a $V_L$ amino acid sequence comprising SEQ ID NO: 8; a $V_H$ amino acid sequence comprising SEQ ID NO: 10 and a $V_L$ amino acid sequence comprising SEQ ID NO: 12; a $V_H$ amino acid sequence comprising SEQ ID NO: 14 and a $V_L$ amino acid sequence comprising SEQ ID NO: 16; a $V_H$ amino acid sequence comprising SEQ ID NO: 18 and a $V_L$ amino acid sequence comprising SEQ ID NO: 20; a $V_H$ amino acid sequence comprising SEQ ID NO: 22 and a $V_L$ amino acid sequence comprising SEQ ID NO: 24; a $V_H$ amino acid sequence comprising SEQ ID NO: 26 and a $V_L$ amino acid sequence comprising SEQ ID NO: 28; a $V_H$ amino acid sequence comprising SEQ ID NO: 30 and a $V_L$ amino acid sequence comprising SEQ ID NO: 32; a $V_H$ amino acid sequence comprising SEQ ID NO: 34 and a $V_L$ amino acid sequence comprising SEQ ID NO: 36; a $V_H$ amino acid sequence comprising SEQ ID NO: 38 and a $V_L$ amino acid sequence comprising SEQ ID NO: 40; a $V_H$ amino acid sequence comprising SEQ ID NO: 42 and a $V_L$ amino acid sequence comprising SEQ ID NO: 44; a $V_H$ amino acid sequence comprising SEQ ID NO: 46 and a $V_L$ amino acid sequence comprising SEQ ID NO: 48; a $V_H$ amino acid sequence comprising SEQ ID NO: 50 and a $V_L$ amino acid sequence comprising SEQ ID NO: 52; or a $V_H$ amino acid sequence comprising SEQ ID NO: 54 and a $V_L$ amino acid sequence comprising SEQ ID NO: 56.

In some aspects, the antibody has a binding affinity within the range of $10^{-5}$ M to $10^{-12}$ M.

In another aspect, the antibody is a bi-specific antibody that also binds to a tumor-associated antigen, a cytokine or a cell surface receptor. For example, the tumor-associated antigen is CAIX. For example, the cytokine is IL-10. For example, the cell surface receptor is CCR4, IL21R, BTLA, HVEM or TIM3.

The present invention provides an antibody linked to a therapeutic agent. For example, the therapeutic agent is a toxin, a radiolabel, a siRNA, a small molecule, or a cytokine.

The present invention provides a cell producing any of the foregoing antibodies.

The present invention also provides methods of selectively killing a tumor cell comprising contacting said cell with any of the foregoing antibodies. In one aspect, the selective killing occurs by antibody-dependent cellular toxicity (ADCC), complement-dependent cytotoxicity (CDC), antibody dependent cellular phagocytosis (ADCP). In another aspect, the tumor cell expresses PD-L1.

The present invention also provides methods of preventing or reversing T cell exhaustion comprising administering to a subject in need thereof a composition comprising any of the foregoing antibodies.

The present invention also provides methods of augmenting an immune response to an antigen comprising administering to a subject in need thereof a composition comprising any of the foregoing antibodies. In one aspect, the antigen is a viral antigen, a bacterial antigen or a tumor associated antigen. In another aspect, the viral antigen is HIV. In a further aspect, the tumor associated antigen is CAIX. In another aspect, the antibody is administered prior to or after exposure to the antigen. In another aspect, the administration of said antibody causes an increase in antigen specific T cell activity. In another aspect, the T-cell is an effector T cell.

The present invention also provides methods of treating or alleviating a symptom of cancer, comprising administering to a subject in need thereof a composition comprising any of the foregoing antibodies. For example, the cancer is renal cell carcinoma or breast cancer. For example, the cancer is a cancer in which PD-L1 is overexpressed. In another example, the cancer is a cancer that induces T cell exhaustion.

The present invention also provides methods of treating or alleviating a symptom of a chronic viral infection, comprising administering to a subject in need thereof a composition comprising any of the foregoing antibodies. For example, the chronic viral infection is an HIV infection. For example, the chronic viral infection is a viral infection that induces T cell exhaustion.

The present invention provides a nucleic acid sequence comprising the nucleic acid sequence of SEQ ID NO: 1, 3, 5, 7, 9, 11, 13. 15. 17, 19, 21, 23, 25, 27, 29, 31, 33, 35, 37, 39, 41, 43, 45, 47, 49, 51, 53 or 55.

In another aspect, the present invention provides a nucleic acid sequence encoding the polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54 or 56.

In another aspect, the present invention provides a polypeptide comprising the amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54 or 56.

In another aspect, the present invention provides a vector comprising a nucleic acid sequence of SEQ ID NO: 1, 3, 5, 7, 9, 11, 13. 15. 17, 19, 21, 23, 25, 27, 29, 31, 33, 35, 37, 39, 41, 43, 45, 47, 49, 51, 53 or 55. The present invention provides a vector comprising a nucleic acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54 or 56. The present invention further provides a cell comprising any one of the foregoing vectors.

The administration routes, in any methods of this disclosure, include, but are not limited to parenteral, (e.g., intravenous), intradermal, subcutaneous, oral (e.g., inhalation), transdermal (i.e., topical), transmucosal, and rectal administration.

The subject in any methods of this disclosure is, for example, a mammal. The mammal is, for example, a human.

Other features and advantages of the invention will be apparent from and are encompassed by the following detailed description and claims.

BRIEF DESCRIPTION OF THE DRAWINGS

FIG. 1. Amino acid sequences of anti-PD-L1 scFv-phage clones (14 clones). Framework regions 1-4 (FW1-4), Complementarily determining regions 1-3 (CDR1-3) and family designations for both the IGHV and IGLV/IGKV are shown. Kabat number is used. Key: "." AA matches to consensus, "X" no consensus AA, and "–" is a space (i.e. no AA). Ab50 VH (SEQ ID NO:38); Ab55VH (SEQ ID NO:46); Ab14 VH (SEQ ID NO:2); Ab65 VH (SEQ ID NO:54); Ab 46VH (SEQ ID NO:34); Ab31 VH (SEQ ID NO:18); Ab32 VH (SEQ ID NO:22); Ab56 VH (SEQ ID NO:50); Ab42 VH (SEQ ID NO:30); Ab52 VH (SEQ ID NO:42); Ab30 VH (SEQ ID NO:14); Ab22 VH (SEQ ID NO:10); Ab16 VH (SEQ ID NO:6); Ab38 VH (SEQ ID NO:26); Ab50 VL (SEQ ID NO:40); Ab55VL (SEQ ID NO:48); Ab14 VL (SEQ ID NO:4); Ab65 VL (SEQ ID NO:56); Ab 46VL (SEQ ID NO:36); Ab31 VL (SEQ ID NO:20); Ab32 VL (SEQ ID NO:24); Ab56 VL (SEQ ID NO:52); Ab42 VL (SEQ ID NO:32); Ab52 VL (SEQ ID NO:44); Ab30 VL (SEQ ID NO:16); Ab22 VL (SEQ ID NO:12); Ab16 VL (SEQ ID NO:8); Ab38 VL (SEQ ID NO:28).

FIG. 7A) Protein gel showing the dissociation of engineered (G37 KIHA) antibody under reducing conditions compared to conjugated (non-reduced) control IgG, parental G37 (WT), and bi-specific (G37 KIHA+PD-L1 KIHB) antibodies. FIG. 7B) Protein gel showing the dissociation of engineered (PD-L1 KIHB) antibody under reducing conditions compared to control IgG, parental PDL-1 (WT), and bi-specific (G37 KIHA+PD-L1 KIHB) antibodies. FIG. 7C) Analysis of bi-specific antibody binding to CAIX$^+$PD-L1$^-$SKRC-52 cells by flow cytometry.

DETAILED DESCRIPTION

Figure 2:
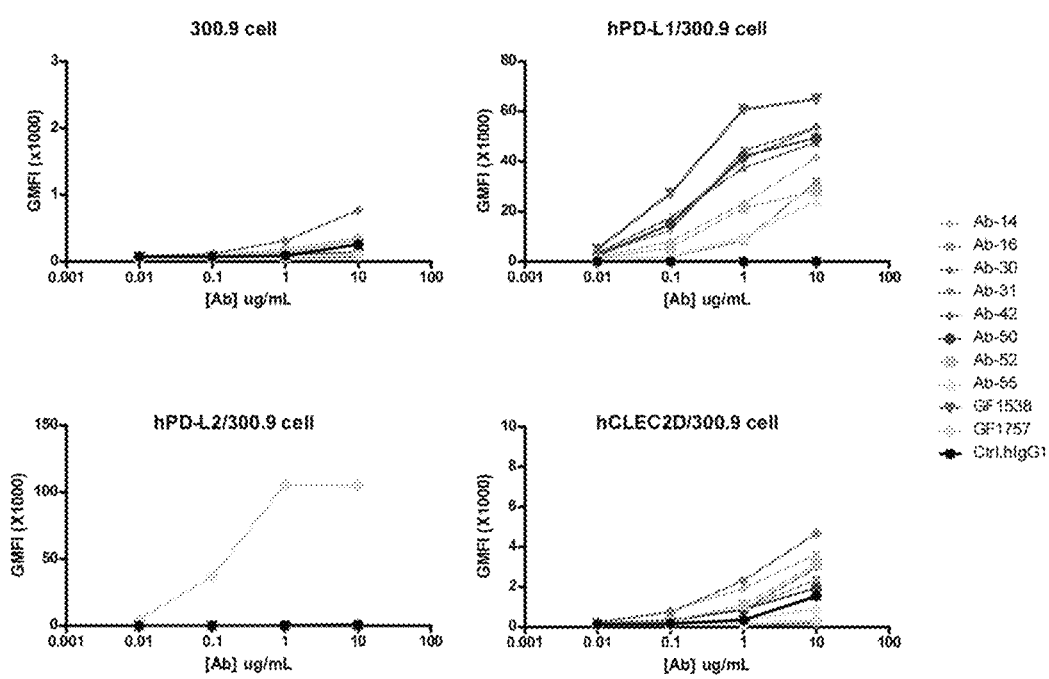
FIG. 2. Binding analysis of huPD-L1 antibodies with human PD-L1 (hPD-L1) expressing cells by FACS. Four types of cells were tested, including parental cell line 300.9 and hPD-L1, hPD-L2 or human C-type lectin domain family 2 member (hCLEC2D) transfected 300.9 cells. GF1538 is a humanized Ab against hPD-L1. GF1757 is a humanized Ab against hPD-L2. Secondary antibody is PE-goat anti-human IgG.

The present invention provides humanized monoclonal antibodies specific against PD-L1, also known as B7H1. The antibodies were identified by a method of phage display antibody library selection by using proteoliposome-coupled-PD-L1 as the library selection target. These antibodies represent a new class of human monoclonal antibodies against PD-L1.

These anti-PD-L1 human monoclonal antibodies are referred to herein as "huPD-L1 antibodies".

Binding of PD-L1 to PD-1 negatively regulates T cell antigen-specific responses, which is critical for tolerance and prevention of autoimmunity and immunopathology. However, excessive PD-L1/PD-1 interaction, which can be caused by chronic antigenic stimulation, can result in inhibition of T cell antigen-specific responses and loss of T cells, which are characteristics of T cell exhaustion. T cell exhaustion is a state of T cell dysfunction that can arise in chronic infections and cancer. It is defined by poor effector function, sustained expression of inhibitory receptors and a transcriptional state distinct from that of functional effector or memory T cells. Exhaustion prevents management of infection and tumor progression.

PD-L1 overexpression has been detected in different cancers. For example, in breast cancer, PD-L1 is overexpressed and associated with high-risk prognostic factors. In renal cell carcinoma, PD-L1 is upregulated and increased expression of PD-1 has also been found in tumor infiltrating leukocytes. Anti-PD-L1 and anti-PD-1 antibodies have demonstrated some clinical efficacy in phase I trials for renal cell carcinoma. Therapeutic agents that can bind to PD-1 or PD-L1 may be useful for specifically targeting tumor cells. Agents that are capable of blocking the PD-1/PD-L1 interaction may be even more useful in treating cancers that have induced T cell exhaustion to evade anti-tumor T cell activity. Use of such agents, alone or in combination with other anti-cancer therapeutics, can effectively target tumor cells that overexpress PD-L1 and increase anti-tumor T cell activity, thereby augmenting the immune response to target tumor cells.

PD-1 and PD-L1 can also be upregulated by T cells after chronic antigen stimulation, for example, by chronic infections. During chronic HIV infection, HIV-specific CD8+ T cells are functionally impaired, showing a reduced capacity to produce cytokines and effector molecules as well as a diminished ability to proliferate. PD-1 is highly expressed on HIV-specific CD8+ T cells of HIV infected individuals. Therefore, blocking this pathway may enhance the ability of HIV-specific T cells to proliferate and produce cytokines in response to stimulation with HIV peptides, thereby augmenting the immune response against HIV. Other chronic infections may also benefit from the use of PD-1/PD-L1 blocking agents, such as chronic viral, bacterial or parasitic infections.

The present invention provides a human monoclonal antibody that specifically binds PD-L1 proteins. Binding of the antibody of the present invention to PD-L1 interrupts the ligand's ability to bind to its receptor PD1. By a variety of mechanisms, the huPD-L1 antibody prevents the negative feedback mechanisms that inhibit T cell responses. In some cases, the huPD-L1 antibody prevents, inhibits or reverses T cell exhaustion. Administration of the huPD-L1 antibody may result in increased T cell proliferation, increased antigen-specific T cell activity, and increased production of effector cytokines. In some instances, the huPD-L1 antibody promotes or augments the antigen-specific immune response. This immune response may be mediated by effector T cells.

The huPD-L1 antibody is monovalent or bivalent and comprises a single or double chain. Functionally, the binding affinity of the huPD-L1 antibody is within the range of $10^{-5}$M to $10^{-12}$ M. For example, the binding affinity of the huPD-L1 antibody is from $10^{-6}$ M to $10^{-12}$ M, from $10^{-7}$ M to $10^{-12}$ M, from $10^{-8}$ M to $10^{-12}$ M, from $10^{-9}$ M to $10^{-12}$ M, from $10^{-5}$ M to $10^{-11}$ M, from $10^{-6}$ M to $10^{-11}$ M, from $10^{-7}$ M to $10^{-11}$ M, from $10^{-8}$ M to $10^{-11}$ M, from $10^{-9}$ M to $10^{-11}$ M, from $10^{-10}$ M to $10^{-11}$ M, from $10^{-5}$ M to $10^{-10}$ M, from $10^{-6}$ M to $10^{-10}$ M, from $10^{-7}$ M to $10^{-10}$ M, from $10^{-8}$ M to $10^{-10}$ M, from $10^{-9}$ M to $10^{-10}$ M, from $10^{-5}$ M to $10^{-9}$ M, from $10^{-6}$ M to $10^{-9}$ M, from $10^{-7}$ M to $10^{-9}$ M, from $10^{-8}$ M to $10^{-9}$ M, from $10^{-5}$ M to $10^{-8}$ M, from $10^{-6}$ M to $10^{-8}$ M, from $10^{-7}$ M to $10^{-8}$ M, from $10^{-5}$ M to $10^{-7}$ M, from $10^{-6}$ M to $10^{-7}$ M or from $10^{-5}$ M to $10^{-6}$ M.

Furthermore, the antibody of the present invention comprises a therapeutic agent including, but not limited to, a toxin, a radiolabel, a siRNA, or a cytokine.

The huPD-L1 antibody is capable of inducing cell death. Cell death is induced by either direct or indirect mechanisms. For instance, PD-L1 binding by the huPD-L1 antibody can lead to complement-dependent cytotoxicity (CDC). Alternatively, the huPD-L1 antibody binds PD-L1, and leads to the recruitment of a second cell type that will kill the PD-L14-expressing target cell. Exemplary mechanisms by which the huPD-L1 antibody mediates cell death by recruitment of a second cell type include, but are not limited to, antibody-dependent cellular toxicity (ADCC) and antibody dependent cellular phagocytosis (ADCP). Target PD-L1-expressing cell types comprise tumor and T cells, such as activated T cells.

Fourteen unique monoclonal huPD-L1 antibodies were identified. These include Ab-14, Ab-16, Ab-22, Ab-30, Ab-31, Ab-32, Ab-38, Ab-42, Ab-46, Ab-50, Ab-52, Ab-55, Ab-56 and Ab-65.

The nucleic acid and amino acid sequence of the monoclonal huPD-L1 antibodies are provided below:

TABLE 1A

Ab-14 Variable Region nucleic acid sequences

V<sub>H</sub> chain of Ab-14 (SEQ ID NO: 1)
CAGGTGCAGCTGGTGCAGTCTGGAGCTGAGGTGAAGAAGCCTGGGGCCTC

AGTGAAGGTCTCCTGCAAGGCTTCTGGTTACACCTTTACCAGCTATGGTA

TCAGCTGGGTGCGACAGGCCCCTGGACAAGGGCTTGAGTGGATGGGATGG

ATCAGCGCTTACAATGGTAACACAAACTATGCACAGAAGCTCCAGGGCAG

AGTCACCATGACCACAGACACATCCACGAGCACAGCCTACATGGAGCTGA

GGAGCCTGAGATCTGACGACACGGCCGTGTATTACTGTGCGAGAGCTCTA

CCTAGTGGGACTATACTGGTCGGAGGTTGGTTCGACCCCTGGGGCCAGGG

AACCCTGGTCACCGTCTCCTCA

V<sub>L</sub> chain of Ab-14 (SEQ ID NO: 3)
AATTTTATGCTGACTCAGCCCCACTCTGTGTCGGAGTCTCCGGGGAAGAC

GGTAACCATCTCCTGCACCCGCAGCAGTGGCAACATTGCCAGCAATTATG

TGCAGTGGTACCAACAGCGCCCGGGCAGTGCCCCCACCACTGTGATCTAT

GAGGATAACCAAAGACCCTCTGGGGTCCCTGATCGGTTCTCTGGCTCCAT

CGACAGCTCCTCCAACTCTGCCTCCCTCACCATCTCTGGACTGAAGACTG

AGGACGAGGCTGACTACTACTGTCAGTCTTATGATAGCAGCAATCTTTGG

GTGTTCGGCGGAGGGACCAAGCTGACCGTCCTA

TABLE 1B

Ab-14 Variable Region amino acid sequences

V<sub>H</sub> chain of Ab-14 (SEQ ID NO: 2)
QVQLVQSGAEVKKPGASVKVSCKASGYTFTSYGISWVRQAPGQGLEWMGW

ISAYNGNTNYAQKLQGRVTMTTDTSTSTAYMELRSLRSDDTAVYYCARAL

PSGTILVGGWFDPWGQGTLVTVSS

V<sub>L</sub> chain of Ab-14 (SEQ ID NO: 4)
NFMLTQPHSVSESPGKTVTISCTRSSGNIASNYVQWYQQRPGSAPTTVIY

EDNQRPSGVPDRFSGSIDSSSNSASLTISGLKTEDEADYYCQSYDSSNLW

VFGGGTKLTVL

TABLE 2A

Ab-16 Variable Region nucleic acid sequences

V<sub>H</sub> chain of Ab-16 (SEQ ID NO: 5)
GAGGTGCAGCTGGTGCAGTCTGGGGGAGGCGTGGTCCAGCCTGGGAGGTC

CCTGAGACTCTCCTGTGCAGCCTCTGGATTCACCTTTAGCAGCTATGCCC

TGAGCTGGGTCCGCCAGGCTCCAGGGAAGGGGCTGGAGTGGGTCTCAGCT

ATTAGTGGTGGTGGTGGTAGCACATACTACGCAGACTCCGTGAAGGGCCG

GTTCACCATCTCCAGAGACAATTCCAAGAACACGCTGTATCTGCAAATGA

ACAGCCTGAGAGCCGAGGACACGGCCGTATATTACTGTGCGAAAGACGTG

TTTCCAGAGACTTTTTCGATGAACTACGGTATGGACGTCTGGGGCCAAGG

AACCCTGGTCACCGTCTCCTCA

TABLE 2A-continued

Ab-16 Variable Region nucleic acid sequences

V<sub>L</sub> chain of Ab-16 (SEQ ID NO: 7)
TCTTCTGAGCTGACTCAGGACCCTGCTGTGTCTGTGGCCTTGGGACAGAC

AGTCAGGATCACATGCCAAGGAGACAGCCTCAGAAGCTATTATGCAAGCT

GGTACCAGCAGAAGCCAGGACAGGCCCCTGTACTTGTCATCTATGGTAAA

AACAACCGGCCCTCAGGGATCCCAGACCGATTCTCTGGCTCCAGCTCAGG

AAACACAGCTTCCTTGACCATCACTGGGGCTCAGGCGGAAGATGAGGCTG

ACTATTACTGTAACTCCCGGGACAGCAGTGGTAACCATTATGTCTTCGGA

ACTGGGACCAAGGTCACCGTCCTA

TABLE 2B

Ab-16 Variable Region amino acid sequences

V<sub>H</sub> chain of Ab-16 (SEQ ID NO: 6)
EVQLVQSGGGVVQPGRSLRLSCAASGFTFSSYALSWVRQAPGKGLEWVSA

ISGGGGSTYYADSVKGRFTISRDNSKNTLYLQMNSLRAEDTAVYYCAKDV

FPETFSMNYGMDVWGQGTLVTVSS

V<sub>L</sub> chain of Ab-16 (SEQ ID NO: 8)
SSELTQDPAVSVALGQTVRITCQGDSLRSYYASWYQQKPGQAPVLVIYGK

NNRPSGIPDRFSGSSSGNTASLTITGAQAEDEADYYCNSRDSSGNHYVFG

TGTKVTVL

TABLE 3A

Ab-22 Variable Region nucleic acid sequences

V<sub>H</sub> chain of Ab-22 (SEQ ID NO: 9)
CAGGTGCAGCTGGTGCAGTCTGGGGGAGGCGTGGTACAGCCTGGGGGGTC

CCTGAGACTCTCCTGTGCAGCCTCTGGATTCACCTTTGATGATTATGCCA

TGCACTGGGTCCGTCAAGCTCCAGGGAAGGGTCTGGAGTGGGTCTCTCTT

ATTAGTGGGGATGGTGGTAGCACATACTATGCAGACTCTGTGAAGGGCCG

ATTCACCATCTCCAGAGACAACAGCAAAAACTCCCTGTATCTGCAAATGA

ACAGTCTGAGAACTGAGGACACCGCCTTGTATTACTGTGCAAAAGTGCTC

CTCCCCTGTAGTAGTACCAGCTGCTATGGAAGCGTCGGTGCTTTTGATAT

CTGGGGCCAAGGGACCACGGTCACCGTCTCCTCA

V<sub>L</sub> chain of Ab-22 (SEQ ID NO: 11)
TAGGACGATGAGCTCGGTCCCAGCTCCGAAGACATAATGATCACTATTAT

TATCCCACACCTGACAGTAATAATCGGCCTCATCACCGGCTTCGACCCTG

CTGATGGTCAGGGTGGCCGTGTTCCCAGAGTTGGAGCCAGAGAATCGCTC

AGAGATCCCTGAGGGCCGGTCCCTATCAGATAGATGACCAACGCAGGGG

CCTGGCCTGGCTTCTGCTGGTACCAGTGCACACTCTTCCTTCCAATGTCG

CTTCCCCCACAGGTAATCCTGGCCGTCTTTCCTGGGGCCACTGACACTGA

GGGTGCCTGAGTCAGCACAGGCAG

TABLE 3B

Ab-22 Variable Region amino acid sequences

$V_H$ chain of Ab-22 (SEQ ID NO: 10)
QVQLVQSGGGVVQPGGSLRLSCAASGFTFDDYAMHWVRQAPGKGLEWVSL

ISGDGGSTYYADSVKGRFTISRDNSKNSLYLQMNSLRTEDTALYYCAKVL

LPCSSTSCYGSVGAFDIWGQGTTVTVSS $V_L$ chain of Ab-22 (SEQ ID NO: 12)
LPVLTQAPSVSVAPGKTARITCGGSDIGRKSVHWYQQKPGQAPALVIYSD

RDRPSGISERFSGSNSGNTATLTISRVEAGDEADYYCQVWDNNSDHYVFG

AGTELIVL

TABLE 4A

Ab-30 Variable Region nucleic acid sequences

$V_H$ chain of Ab-30 (SEQ ID NO: 13)
CAGGTGCAGCTGGTGCAGTCTGGGGGAAGTGTGGTACGGCCTGGGGAATC

CCTCAGACTCTCCTGTGTAGCCTCTGGATTCATCTTTGATAATTATGACA

TGAGTTGGGTCCGCCAAGTTCCAGGGAAGGGGCTGGAGTGGGTCTCTCGT

GTTAATTGGAATGGTGGTAGCACAACTTATGCAGACGCTGTGAAGGGCCG

ATTCACCATCTCCAGAGACAACACCAAGAACTCCCTGTATCTACAAATGA

ACAACCTGAGAGCCGAAGACACGGCCGTGTATTACTGTGTGCGCGAGTTT

GTCGGTGCTTATGATCTCTGGGGCCAGGGGACCACGGTCACCGTCTCCTC

A $V_L$ chain of Ab-30 (SEQ ID NO: 15)
CAGTCTGCCCTGACTCAGCCTGCCTCCGTGTCTGGGTCTCCTGGACAGTC

GATCACCATCTCCTGCACTGGAACCAGCAGTGACGTTGGTGGTTATAACT

ATGTCTCCTGGTACCAACAACACCCAGGCAAAGCCCCCAAACTCATGATT

TATGATGTCAGTAATCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATATACAAGCAGCACTCTGCCGTTC

GGCGGAgGGACCAAGCTGACCGTCCTA

TABLE 4B

Ab-30 Variable Region amino acid sequences

$V_H$ chain of Ab-30 (SEQ ID NO: 14)
QVQLVQSGGSVVRPGESLRLSCVASGFIFDNYDMSWVRQVPGKGLEWVSR

VNWNGGSTTYADAVKGRFTISRDNTKNSLYLQMNNLRAEDTAVYYCVREF

VGAYDLWGQGTTVTVSS $V_L$ chain of Ab-30 (SEQ ID NO: 16)
QSALTQPASVSGSPGQSITISCTGTSSDVGGYNYVSWYQQHPGKAPKLMI

YDVSNRPSGVSNRFSGSKSGNTASLTISGLQAEDEADYYCSSYTSSTLPF

GGGTKLTVL

TABLE 5A

Ab-31 Variable Region nucleic acid sequences

$V_H$ chain of Ab-31 (SEQ ID NO: 17)
CAGGTGCAGCTGGTGCAGTCTGGGGCTGAGGTGAAGAAGCCAGGGGCCAC

AGTGAAGGTCTCCTGCAAGGTTTTTGGAGACACCTTCCGCGGCCTCTATA

TACACTGGGTGCGACAGGCCCCTGGACAAGGGCTTGAGTGGATGGGAGGG

ATCATCCCTATCTTTGGTACAGCAAACTACGCACAGAAGTTCCAGGGCAG

AGTCACGATTACCACGGACGAATCCACGAGCACAGCCTACATGGAGCTGA

GCAGCCTGAGATCTGAGGACACGGCCGTGTATTACTGTGCGAGCGGACTA

CGTTGGGGGATCTGGGGCTGGTTCGACCCCTGGGGCCAGGGCACCCTGGT

CACCGTCTCCTCA $V_L$ chain of Ab-31 (SEQ ID NO: 19)
GAAATTGTGTTGACGCAGTCTCCAGCCACCCTGTCTTTGTCTCCAGGGGA

AAGAGCCACCCTCTCCTGCAGGGCCAGTCAGAGTATTGGCAACAGCTTAG

CCTGGTACCAGCAGAAACCTGGCCAGGCTCCCAGGCTCCTCATGTATGGT

GCATCCAGCAGGGCCACTGGCATCCCAGACAGGTTCAGTGGCAGTGGGGC

TGGGACAGACTTCACTCTCACCATCAGCAGCCTAGAGCCTGAAGATTTTG

CAACGTATTACTGTCAGCAGCATACTATCCCAACATTCTCTTTCGGCCCT

GGGACCAAAGTGGAAGTCAAA

TABLE 5B

Ab-31 Variable Region amino acid sequences

$V_H$ chain of Ab-31 (SEQ ID NO: 18)
QVQLVQSGAEVKKPGATVKVSCKVFGDTFRGLYIHWVRQAPGQGLEWMGG

IIPIFGTANYAQKFQGRVTITTDESTSTAYMELSSLRSEDTAVYYCASGL

RWGIWGWFDPWGQGTLVTVSS $V_L$ chain of Ab-31 (SEQ ID NO: 20)
EIVLTQSPATLSLSPGERATLSCRASQSIGNSLAWYQQKPGQAPRLLMYG

ASSRATGIPDRFSGSGAGTDFTLTISSLEPEDFATYYCQQHTIPTFSFGP

GTKVEVK

TABLE 6A

Ab-32 Variable Region nucleic acid sequences

$V_H$ chain of Ab-32 (SEQ ID NO: 21)
GAGGTGCAGCTGGTGCAGTCTGGGGCTGAGCTGAAGAAGCCTGGGTCCTC

GGTGAAGGTCTCCTGCAAGGCTTTTGGAGGCACCTTCAGTGACAATGCTA

TCAGCTGGGTGCGACAGGCCCCTGGACAAGGGCCTGAGTGGATGGGGGGC

ATCATTCCTATCTTTGGAAAACCAAACTACGCACAGAAGTTCCAGGGCAG

AGTCACGATTACCGCGGACGAATCCACGAGCACTGCCTACATGGTCCTGA

GCAGCCTGAGATCTGAGGACACGGCCGTATATTACTGTGCGAGAACTATG

GTTCGGGGCTTTCTTGGGGTTATGGACGTCTGGGGCCAAGGGACCACGGT

CACCGTCTCCTCA

TABLE 6A-continued

Ab-32 Variable Region nucleic acid sequences

V$_L$ chain of Ab-32 (SEQ ID NO: 23)
GATATTGTGATGACCCAGACTCCATCCTTCCTGTCCGCATCCATAGGAGA

CAGAGTCACCATCACTTGCCGGGCCAGTCAGGGCATTGGCAGTTATTTAG

CCTGGTATCAGCAAAGACCAGGGGAAGCCCCTAAGCTCCTGATCTATGCT

GCATCGACTTTGCAAAGTGGAGTCCCATCAAGGTTCAGCGGCAGTGGATC

TGGGACGGACTTCACTCTCACAATCAGCAACCTGCAGCCTGAAGATTTTG

CAACTTATTACTGTCAACAGCTTAATAATTACCCGATCACCTTCGGCCAA

GGGACACGACTGGAGATTAAA

TABLE 6B

Ab-32 Variable Region amino acid sequences

V$_H$ chain of Ab-32 (SEQ ID NO: 22)
EVQLVQSGAELKKPGSSVKVSCKAFGGTFSDNAISWVRQAPGQGPEWMGG
IIPIFGKPNYAQKFQGRVTITADESTSTAYMVLSSLRSEDTAVYYCARTM
VRGFLGVMDVWGQGTTVTVSS V$_L$ chain of Ab-32 (SEQ ID NO: 24)
DIVMTQTPSFLSASIGDRVTITCRASQGIGSYLAWYQQRPGEAPKLLIYA
ASTLQSGVPSRFSGSGSGTDFTLTISNLQPEDFATYYCQQLNNYPITFGQ
GTRLEIK

TABLE 7A

Ab-38 Variable Region nucleic acid sequences

V$_H$ chain of Ab-38 (SEQ ID NO: 25)
CAGGTGCAGCTGGTGCAGTCTGGGGGAGGCTTGGTACAGCCTGGGGGGTC

CCTGAGACTCTCCTGTGCAGCCTCTGGATTCACCTTTAGCAGCTATGCCA

TGAGCTGGGTCCGCCAGGCTCCAGGGAAGGGGCTGGAGTGGGTCTCAGCT

ATTAGTGGTAGTGGTGGTAGCACATACTACGCAGACTCCGTGAAGGGCCG

GTTCACCATCTCCAGAGACAATTCCAAGAACACGCTGTATCTGCAAATGA

ACAGCCTGAGAGCCGAGGACACGGCCGTATATTACTGTGCGAAAGATCAG

TTCGTTACGATTTTTGGAGTGCCAAGATACGGTATGGACGTCTGGGGCCA

AGGGACCACGGTCACCGTCTCCTCA

V$_L$ chain of Ab-38 (SEQ ID NO: 27)
CAGTCTGCCCTGACTCAGCCACCCTCAGTGTCCGTGTCCCCAGGACAGAC

AGCCAACATCCCCTGCTCTGGAGATAAATTGGGGAATAAATATGCTTACT

GGTATCAGCAGAAGCCAGGCCAGTCCCCTGTACTGCTCATCTATCAAGAT

ATCAAGCGGCCCTCAAGGATCCCTGAGCGATTCTCTGGCTCCAACTCTGC

GGACACAGCCACTCTGACCATCAGCGGGACCCAGGCTATGGATGAGGCTG

ACTATTACTGTCAGACGTGGGACAACAGCGTGGTCTTCGGCGGCGGGACC

AAGCTGACCGTCCTC

TABLE 7B

Ab-38 Variable Region amino acid sequences

V$_H$ chain of Ab-38 (SEQ ID NO: 26)
QVQLVQSGGGLVQPGGSLRLSCAASGFTFSSYAMSWVRQAPGKGLEWVSA
ISGSGGSTYYADSVKGRFTISRDNSKNTLYLQMNSLRAEDTAVYYCAKDQ
FVTIFGVPRYGMDVWGQGTTVTVSS V$_L$ chain of Ab-38 (SEQ ID NO: 28)
QSALTQPPSVSVSPGQTANIPCSGDKLGNKYAYWYQQKPGQSPVLLIYQD
IKRPSRIPERFSGSNSADTATLTISGTQAMDEADYYCQTWDNSVVFGGGT
KLTVL

TABLE 8A

Ab-42 Variable Region nucleic acid sequences

V$_H$ chain of Ab-42 (SEQ ID NO: 29)
CAGGTGCAGCTGGTGCAGTCTGGGGCTGAGGTGAAGAAGCCTGGGTCCTC

GGTGAAGGTCTCCTGCAAGGCTTCTGGAGGCACCTTCAGCAGCTATGCTA

TCAGCTGGGTGCGACAGGCCCCTGGACAAGGGCTTGAGTGGATGGGAGGG

ATCATCCCTATCTTTGGTACAGCAAACTACGCACAGAAGTTCCAGGGCAG

AGTCACGATTACCGCGGACAAATCCACGAGCACAGCCTACATGGAGCTGA

GCAGCCTGAGATCTGAGGACACGGCCGTCTATTACTGTGCGAGAGGGCGT

CAAATGTTCGGTGCGGGAATTGATTTCTGGGGCCCGGGCACCCTGGTCAC

CGTCTCCTCA

V$_L$ chain of Ab-42 (SEQ ID NO: 31)
AATTTTATGCTGACTCAGCCCCACTCTGTGTCGGAGTCTCCGGGGAAGAC

GGTAACCATCTCCTGCACCCGCAGCAGTGGCAGCATTGACAGCAACTATG

TGCAGTGGTACCAGCAGCGCCCGGGCAGCGCCCCCACCACTGTGATCTAT

GAGGATAACCAAAGACCCTCTGGGGTCCCTGATCGGTTCTCTGGCTCCAT

CGACAGCTCCTCCAACTCTGCCTCCCTCACCATCTCTGGACTGAAGACTG

AGGACGAGGCTGACTACTACTGTCAGTCTTATGATAGCAACAATCGTCAT

GTGATATTCGGCGGAGGGACCAAGCTGACCGTCCTA

TABLE 8B

Ab-42 Variable Region amino acid sequences

V$_H$ chain of Ab-42 (SEQ ID NO: 30)
QVQLVQSGAEVKKPGSSVKVSCKASGGTFSSYAISWVRQAPGQGLEWMGG
IIPIFGTANYAQKFQGRVTITADKSTSTAYMELSSLRSEDTAVYYCARGR
QMFGAGIDFWGPGTLVTVSS V$_L$ chain of Ab-42 (SEQ ID NO: 32)
NFMLTQPHSVSESPGKTVTISCTRSSGSIDSNYVQWYQQRPGSAPTTVIY
EDNQRPSGVPDRFSGSIDSSSNSASLTISGLKTEDEADYYCQSYDSNNRH
VIFGGGTKLTVL

TABLE 9A

Ab-46 Variable Region nucleic acid sequences

V$_H$ chain of Ab-46 (SEQ ID NO: 33)
GAGGTGCAGCTGGTGGAGTCTGGGGCTGAAGTAAAGAAGCCTGGGTCCTC
GGTGAAAGTCTCCTGCAAGGTTTCAGGAGGCACATTCGGCACCTATGCTC

TABLE 9A-continued

Ab-46 Variable Region nucleic acid sequences

TCAACTGGGTGCGCCAGGCCCCTGGACAAGGGCTTGAGTGGATGGGAAGG
ATCGTCCCTCTCATTGGTCTAGTAAACTACGCACATAACTTTGAGGGCAG
AATCTCGATTACCGCGGACAAGTCCACGGGCACAGCCTACATGGAACTGA
GCAACCTGAGATCTGACGACACGGCCGTGTATTACTGTGCGAGAGAGGTC
TACGGTGGTAACTCCGACTACTGGGGCCAGGGAACCCTGGTCACCGTCTC
CTCA $V_L$ chain of Ab-46 (SEQ ID NO: 35)
AATTTTATGCTGACTCAGCCCCACTCAGTGTCGGAGTCTCCGGGGAAGAC
GGTAACCATCTCCTGCACTCGCAGTAGTGGCAACATTGGCACCAACTATG
TGCAGTGGTACCAGCAGCGCCCGGGCAGTGCCCCCGTCGCTTTGATCTAC
GAGGATTATCGAAGACCCTCTGGGGTCCCTGATCGGTTCTCTGGCTCCAT
CGACAGCTCCTCCAACTCTGCCTCCCTCATCATCTCTGGACTGAAGCCTG
AGGACGAGGCTGACTACTACTGTCAGTCTTATCATAGCAGCGGTTGGGAA
TTCGGCGGAGGGACCAAGCTGACCGTCCTC

TABLE 9B

Ab-46 Variable Region amino acid sequences

$V_H$ chain of Ab-46 (SEQ ID NO: 34)
EVQLVESGAEVKKPGSSVKVSCKVSGGTFGTYALNWVRQAPGQGLEWMGR
IVPLIGLVNYAHNFEGRISITADKSTGTAYMELSNLRSDDTAVYYCAREV
YGGNSDYWGQGTLVTVSS $V_L$ chain of Ab-46 (SEQ ID NO: 36)
NFMLTQPHSVSESPGKTVTISCTRSSGNIGTNYVQWYQQRPGSAPVALIY
EDYRRPSGVPDRFSGSIDSSSNSASLIISGLKPEDEADYYCQSYHSSGWE
FGGGTKLTVL

TABLE 10A

Ab-50 Variable Region nucleic acid sequences

$V_H$ chain of Ab-50 (SEQ ID NO: 37)
CAGGTGCAGCTGGTGCAGTCTGGAGGTGAGGTGAAGAAGCCGGGGCCTC
AGTGAAGGTCTCCTGCAAGGCTTCTGGTTACACCTTGAGCAGTCATGGTA
TAACCTGGGTGCGACAGGCCCCTGGACAAGGGCTTGAGTGGATGGGATGG
ATCAGCGCTCACAATGGTCACGCTAGCAATGCACAGAAGGTGGAGGACGA
AGTCACTATGACTACTGACACATCCACGAACACAGCCTACATGGAACTGA
GGAGCCTGACAGCTGACGACACGGCCGTGTATTACTGTGCGAGAGTACAT
GCTGCCCTCTACTATGGTATGGACGTCTGGGGCCAAGGAACCCTGGTCAC
CGTCTCCTCA $V_L$ chain of Ab-50 (SEQ ID NO: 39)
CAGTCTGTGCTGACTCAGCCACCCTCGGTGTCAGTGGCCCCAGGACAGAC
GGCCAGGATTACCTGTGGGGGAAACAACATTGGAAGTAAAGGTGTGCACT
GGTATCAGCAGAAGCCAGGCCAGGCCCCTGTACTGGTCGTCTATGATGAT
AGTGACCGGCCCTCAGGGATCCCTGAGCGATTCTCTGCTCCAACTCTGG
GAACACGGCCACCCTGACCATCAGCAGGGTCGAAGCCGGGGATGAGGCCG
ACTATTACTGTCAGGTGTGGGATAGTAGTAGTGATCATTGGGTGTTCGGC
GGAGGGACCAAGCTGACCGTCCTA

TABLE 10B

Ab-50 Variable Region amino acid sequences

$V_H$ chain of Ab-50 (SEQ ID NO: 38)
QVQLVQSGGEVKKPGASVKVSCKASGYTLSSHGITWVRQAPGQGLEWMGW
ISAHNGHASNAQKVEDRVTMTTDTSTNTAYMELRSLTADDTAVYYCARVH
AALYYGMDVWGQGTLVTVSS $V_L$ chain of Ab-50 (SEQ ID NO: 40)
QSVLTQPPSVSVAPGQTARITCGGNNIGSKGVHWYQQKPGQAPVLVVYDD
SDRPSGIPERFSGSNSGNTATLTISRVEAGDEADYYCQVWDSSSDHWVFG
GGTKLTVL

TABLE 11A

Ab-52 Variable Region nucleic acid sequences

$V_H$ chain of Ab-52 (SEQ ID NO: 41)
CAGGTGCAGCTGCAGGAGTCGGGGGGAGGCGTGGTCAGCCTGGGAGGTC
CCTGAGACTCTCCTGTCAGCCTCTGGATTCACCTTCAGCAGACATGGCA
TGCACTGGGTCCGCCAGGCTCCAGGCAAGGGGCTGGAGTGGGTGGCAGTG
ATATCACATGATGGAAGTGTAAAATACTATGCAGACTCCATGAAGGGCCG
ATTCAGCATCTCCAGAGACAATTCCAACAACACACTGTATCTCCAAATGG
ACAGCCTGAGAGCTGACGACACGGCCGTTTATTACTGTGCGAGAGGACTG
TCGTACCAGGTGTCGGGGTGGTTCGACCCCTGGGGCCAGGGCACCCTGGT
CACCGTCTCCTCA $V_L$ chain of Ab-52 (SEQ ID NO: 43)
AATTTTATGCTGACTCAGCCCCACTCTGTGTCGGAGTCTCCGGGGAAGAC
GGTAACCATCTCCTGCACCCGCAGCAGTGGCAGCATTGCCAGCAACTATG
TGCAGTGGTACCAGCAGCGCCCGGGCAGTGCCCCCACCACTGTGATCTAT
GAGGATAACCAAAGACCCTCTGGGGTCCCTGATCGGTTCTCTGGCTCCAT
CGACAGCTCCTCCAACTCTGCCTCCCTCACCATCTCTGGACTGAAGACTG
AGGACGAGGCTGACTACTACTGTCAGTCTTATGATAGCACCACCCCTTCG
GTGTTCGGCGGCGGGACCAAGCTGACCGTCCTA

TABLE 11B

Ab-52 Variable Region amino acid sequences

$V_H$ chain of Ab-52 (SEQ ID NO: 42)
QVQLQESGGGVVQPGRSLRLSCSASGFTFSRHGMHWVRQAPGKGLEWVAV
ISHDGSVKYYADSMKGRFSISRDNSNNTLYLQMDSLRADDTAVYYCARGL
SYQVSGWFDPWGQGTLVTVSS $V_L$ chain of Ab-52 (SEQ ID NO: 44)
NFMLTQPHSVSESPGKTVTISCTRSSGSIASNYVQWYQQRPGSAPTTVIY
EDNQRPSGVPDRFSGSIDSSSNSASLTISGLKTEDEADYYCQSYDSTTPS
VFGGGTKLTVL

TABLE 12A

Ab-55 Variable Region nucleic acid sequences

$V_H$ chain of Ab-55 (SEQ ID NO: 45)
CAGGTGCAGCTGGTGCAGTCTGGAGCTGAGGTGAAGAAGCCTGGGGCCTC
AGTGAAGGTCTCCTGCAAGGCTTCTGGTTACACCTTTACCAGCTATGGTA
TCAGCTGGGTGCGACAGGCCCCTGGACAAGGGCTTGAGTGGATGGGATGG
ACCAGCCCTCATAATGGTCTCACAGCATTTGCACAGATCCTAGAGGGCCG
AGTCACCATGACCACAGACACATCCACGAACACAGCCTACATGGAATTGA
GGAACCTGACATTTGATGACACGGCCGTTTATTTCTGTGCGAAAGTACAT
CCTGTCTTCTCTTATGCGTTGGACGTCTGGGGCCAAGGCACCCTGGTCAC
CGTCTCCTCA $V_L$ chain of Ab-55 (SEQ ID NO: 47)
AATTTTATGCTGACTCAGCCCCACTCTGTGTCGGAGTCCCCGGGGAAGAC
GGTAACCATCTCCTGCACCCGCAGCAGTGGCAGCATTGCCAGCAACTATG
TACAGTGGTACCAGCAGCGCCCGGGCAGTTCCCCACCACTGTGATCTAT
GAAGATAACCAAAGACCCTCTGGGGTCCCTGATCGGTTCTCTGGCTCCAT
CGACACCTCCTCCAACTCTGCCTCCCTCACCATCTCTGGACTGAAGACTA
AGGACGAGGCGGACTACTACTGTCAGTCTTATGATGGCATCACTGTGATT
TTCGGCGGAGGGACCAAGTTGACCGTCCTA

TABLE 12B

Ab-55 Variable Region amino acid sequences

$V_H$ chain of Ab-55 (SEQ ID NO: 46)
QVQLVQSGAEVKKPGASVKVSCKASGYTFTSYGISWVRQAPGQGLEWMGW
TSPHNGLTAFAQILEGRVTMTTDTSTNTAYMELRNLTFDDTAVYFCAKVH
PVFSYALDVWGQGTLVTVSS $V_L$ chain of Ab-55 (SEQ ID NO: 48)
NFMLTQPHSVSESPGKTVTISCTRSSGSIASNYVQWYQQRPGSSPTTVIY
EDNQRPSGVPDRFSGSIDSSNSASLTISGLKTKDEADYYCQSYDGITVI
FGGGTKLTVL

TABLE 13A

Ab-56 Variable Region nucleic acid sequences

V_H chain of Ab-56 (SEQ ID NO: 49)
GAGGTGCAGCTGGTGGAGTCTGGGAGCTGAGGTGATGAACCCTGGGTCCTC
GGTGAGGGTCTCCTGCAGGGGTTCTGGAGGCGACTTCAGTACCTATGCTT
TCAGCTGGGTGCGACAGGCCCCTGGACAAGGGCTTGAGTGGATGGGAAGG
ATCATCCCTATCCTTGGTATAGCAAACTACGCACAGAAGTTCCAGGGCAG
GGTCACGATTACCGCGGACAAATCCACGAGCACAGCCTACATGGAGCTGA
GCAGCCTGAGATCTGACGATACGGCCGTGTATTACTGTGCGAGAGATGGC
TATGGTTCGGACCCGGTGCTATGGGGCCAGGGCACCCTGGTCACCGTCTC
CTCA V_L chain of Ab-56 (SEQ ID NO: 51)
AATTTTATGCTGACTCAGCCCCACTCTGTGTCGGGGTCTCCGGGGAAGAC
GGTAACCCTCCCCTGCACCCGCAGCAGTGGCAGCATTGCCAGCCACTATG
TCCAGTGGTACCAGCAGCGCCCGGGCAGTGCCCCCACCACTGTGATCTAT
GAGGATAACAAGAGACCCTCTGGGGTCCCTGATCGGTTCTCTGGCTCCAT
CGACAGCTCCTCCAACTCTGCCTCCCTCAGCATCTCTGGACTGAAGACTG
AGGACGAGGCTGACTACTACTGTCAGTCTTATGATAGCAGCAATCGTTGG
GTGTTCGGCGGAGGGACCAAGCTGACCGTCCTA

TABLE 13B

Ab-56 Variable Region amino acid sequences

V_H chain of Ab-56 (SEQ ID NO: 50)
EVQLVESGAEVMNPGSSVRVSCRGSGGDFSTYAFSWVRQAPGQGLEWMGR
IIPILGIANYAQKFQGRVTITADKSTSTAYMELSSLRSDDTAVYYCARDG
YGSDPVLWGQGTLVTVSS V_L chain of Ab-56 (SEQ ID NO: 52)
NFMLTQPHSVSGSPGKTVTLPCTRSSGSIASHYVQWYQQRPGSAPTTVIY
EDNKRPSGVPDRFSGSIDSSSNSASLSISGLKTEDEADYYCQSYDSSNRW
VFGGGTKLTVL

TABLE 14A

Ab-65 Variable Region nucleic acid sequences

V_H chain of Ab-65 (SEQ ID NO: 53)
GAGGTGCAGCTGGTGCAGTCTGGAGCTGAGGTGAAGAAGCCTGGGGCCTC
AGTGAAGGTCTCCTGCAAGGCTTCTGGTTACACCTTTACCAACTATGGTA
TCAGCTGGGTGCGACAGGCCCCTGGACAAGGGCTTGAGTGGATGGGATGG
ATCAGCGCTTACAATGGTAACACAAACTATGCACAGAAGGTCCAGGGCAG
AGTCACCATGACCACAGACACATCCACGAGCACAGGCTACATGGAGCTGA
GGAGCCTGAGATCTGACGACACGGCCGTGTATTACTGTGCGAGAGGAGAT
TTTCGGAAACCCTTTGACTACTGGGGCCAGGGAACCCTGGTCACCGTCTC
CTCA V_L chain of Ab-65 (SEQ ID NO: 55)
CTGCCTGTGCTGACTCAGCCGGCTTCCCTCTCTGCATCCCCCGGAGCATC
AGCCAGTCTCACCTGCACCTTACGCAGTGGCCTCAATGTTGGTTCCTACA
GGATATACTGGTACCAGCAGAAGCCAGGGAGTCGTCCCCAGTATCTCCTG
AACTACAAATCAGACTCAAATAAACAGCAGGCCTCTGGAGTCCCCAGCCG
CTTCTCTGGATCCAAGGATGCTTCGGCCAATGCAGGGATTTTACTCATCT
CCGGGCTCCAGTCTGAGGATGAGGCTGACTATTACTGTATGATTTGGTAC
AGCAGCGCTGTGGTATTCGGCGGAGGGACCAAGCTGACCGTCCTA

TABLE 14B

Ab-65 Variable Region amino acid sequences

V_H chain of Ab-65 (SEQ ID NO: 54)
EVQLVQSGAEVKKPGASVKVSCKASGYTFTNYGISWVRQAPGQGLEWMGW
ISAYNGNTNYAQKVQGRVTMTTDTSTSTGYMELRSLRSDDTAVYYCARGD
FRKPFDYWGQGTLVTVSS V_L chain of Ab-65 (SEQ ID NO: 56)
LPVLTQPASLSASPGASASLTCTLRSGLNVGSYRIYWYQQKPGSRPQYLL
NYKSDSNKQQASGVPSRFSGSKDASANAGILLISGLQSEDEADYYCMIWY
SSAVVFGGGTKLTVL The amino acid sequences of the heavy and light chain complementary determining regions of the huPD-L1 antibodies are shown in Table 15A and 15B below.

TABLE 15A

Amino acid sequences of the complementary determining regions of the heavy chain.

| Antibody | CDR1 | SEQ ID NO: | CDR2 | SEQ ID NO: | CDR3 | SEQ ID NO: |
|---|---|---|---|---|---|---|
| Consensus | SYAIS | 57 | WISPIGGSTNYAQKVQG | 70 | GLXXXXXXXXXXXXXXDV | 85 |
| Ab-14 | SYGIS | 58 | WISAYNGNTNYAQKLED | 71 | ALPSGTILVGGWFDP | 86 |
| Ab-16 | SYALS | 59 | AISGGGGSTYYADSVKD | 72 | DVFPETFSMNYGMDV | 87 |
| Ab-22 | DYAMH | 60 | LISGDGGSTYYADSVKD | 73 | VLLPCSSTSCYGSVGAFDI | 88 |
| Ab-30 | NYDMS | 61 | RVNWNGGSTTYADAVKD | 74 | EFVGAYDL | 89 |
| Ab-31 | GLYIH | 62 | WIIPIFGTANYAQKFED | 75 | GLRWGIWGWFDP | 90 |
| Ab-32 | DNAIS | 63 | WIIPIFGKPNYAQKFED | 76 | TMVRGFLGVMDV | 91 |
| Ab-38 | SYAMS | 64 | AISGSGGSTYYADSVKD | 77 | DQFVTIFGVPRYGMDV | 92 |
| Ab-42 | SYAIS | 57 | WIIPIFGTANYAQKFED | 78 | GRQMFGAGIDF | 93 |
| Ab-46 | TYALN | 65 | RIVPLIGLVNYAHNFED | 79 | EVYGGNSDY | 94 |
| Ab-50 | SHGIT | 66 | WISAHNGHASNAQKVED | 80 | VHAALYYGMDV | 95 |
| Ab-52 | RHGMH | 67 | VISHDGSVKYYADSMKD | 81 | GLSYQVSGWFDP | 96 |
| Ab-55 | SYGIS | 58 | WTSPHNGLTAFAQILED | 82 | VHPVFSYALDV | 97 |

TABLE 15A-continued

Amino acid sequences of the complementary determining regions of the heavy chain.

| Antibody | CDR1 | SEQ ID NO: | CDR2 | SEQ ID NO: | CDR3 | SEQ ID NO: |
|---|---|---|---|---|---|---|
| Ab-56 | TYAFS | 68 | RIIPILGIANYAQKFED | 83 | DGYGSDPVL | 98 |
| Ab-65 | NYGIS | 69 | WISAYNGNTNYAQKVED | 84 | GDFRKPFDY | 99 |

TABLE 15B

Amino acid sequences of the complementary determining regions of the light chain.

| Antibody | CDR1 | SEQ ID NO: | CDR2 | SEQ ID NO: | CDR3 | SEQ ID NO: |
|---|---|---|---|---|---|---|
| Consensus | TRSSGSIGSNYVQ | 100 | EDNQRPS | 115 | QSYDSSTWV | 126 |
| Ab-14 | TRSSGNIASNYVQ | 101 | EDNQRPS | 115 | QSYDSSNLWV | 127 |
| Ab-16 | QGDSLRSYYAS | 102 | GKNNRPS | 116 | NSRDSSGNHYV | 128 |
| Ab-22 | GGSDIGRKSVH | 103 | SDRDRPS | 117 | QVWDNNSDHYV | 129 |
| Ab-30 | TGTSSDVGGYNYVS | 104 | DVSNRPS | 118 | SSYTSSTLP | 130 |
| Ab-31 | RASQSIGNSLA | 105 | GASSRAT | 119 | QQHTIPTFS | 131 |
| Ab-32 | RASQGIGSYLA | 106 | AASTLQS | 120 | QQLNNYPIT | 132 |
| Ab-38 | SGDKLGNKYAY | 107 | QDIKRPS | 121 | QTWDNSVV | 133 |
| Ab-42 | TRSSGSIDSNYVQ | 108 | EDNQRPS | 115 | QSYDSNNRHVI | 134 |
| Ab-46 | TRSSGNIGTNYVQ | 109 | EDYRRPS | 122 | QSYHSSGWE | 135 |
| Ab-50 | GGNNIGSKGVH | 110 | DDSDRPS | 123 | QVWDSSSDHWV | 136 |
| Ab-52 | TRSSGSIASNYVQ | 111 | EDNQRPS | 115 | QSYDSTTPSV | 137 |
| Ab-55 | TRSSGSIASNYVQ | 112 | EDNQRPS | 115 | QSYDGITVI | 138 |
| Ab-56 | TRSSGSIASHYVQ | 113 | EDNKRPS | 124 | QSYDSSNRWV | 139 |
| Ab-65 | TLRSGLNVGSYRIY | 114 | YKSDSNKQQAS | 125 | MIWYSSAVV | 140 |

The huPD-L1 antibodies described herein bind to PD-L1. In one aspect, the huPD-L1 antibodies have high affinity and high specificity for PD-L1. In another aspect, the huPD-L1 antibodies can bind the PD-1 receptor and prevent, inhibit, or block the ligand PD-L1 from binding its receptor PD-1. In some instances, the huPD-L1 antibodies may have some cross-reactivity with PD-L2. In some instances, the huPD-L1 antibodies do not exhibit any cross-reactivity with PD-L2. In some instances, the huPD-L1 antibodies bind to PD-L1 with higher affinity and/or higher specificity than to PD-L2.

The present invention also features antibodies that have a specified percentage identity or similarity to the amino acid or nucleotide sequences of the huPD-L1 antibodies described herein. For example, the antibodies may have 60%, 70%, 75%, 80%, 85%, 90%, 91%, 92%, 93%, 94%, 95%, 96%, 97%, 98%, 99%, or higher identity when compared a specified region or the full length of any one of the huPD-L1 antibodies described herein. Sequence identity or similarity to the nucleic acids and proteins of the present invention can be determined by sequence comparison and/or alignment by methods known in the art. For example, sequence comparison algorithms (i.e. BLAST or BLAST 2.0), manual alignment or visual inspection can be utilized to determine percent sequence identity or similarity for the nucleic acids and proteins of the present invention.

As to amino acid sequences, one of skill in the art will readily recognize that individual substitutions, deletions or additions to a nucleic acid, peptide, polypeptide, or protein sequence which alters, adds, deletes, or substitutes a single amino acid or a small percentage of amino acids in the encoded sequence is collectively referred to herein as a "conservatively modified variant". In some embodiments the alteration results in the substitution of an amino acid with a chemically similar amino acid. Conservative substitution tables providing functionally similar amino acids are well known in the art. Such conservatively modified variants of the huPD-L1 antibody disclosed herein may exhibit increased cross-reactivity to PD-L2 in comparison to an unmodified huPD-L1 antibody.

Antibodies

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically binds" or "immunoreacts with" is meant that the antibody reacts with one or more antigenic determinants of the desired antigen and does not react with other polypeptides. Antibodies include, but are not limited to, polyclonal, monoclonal, chimeric, dAb (domain antibody), single chain, $F_{ab}$, $Fab_{ab'}$ and $F_{(ab')2}$ fragments, scFvs, and $F_{ab}$ expression libraries.

A single chain Fv ("scFv") polypeptide molecule is a covalently linked $V_H{:}V_L$ heterodimer, which can be expressed from a gene fusion including $V_H$- and $V_L$-encoding genes linked by a peptide-encoding linker. (See Huston et al. (1988) Proc Nat Acad Sci USA 85(16):5879-5883). A number of methods have been described to discern chemical structures for converting the naturally aggregated, but chemically separated, light and heavy polypeptide chains from an antibody V region into an scFv molecule, which will fold into a three dimensional structure substantially similar to the structure of an antigen-binding site. See, e.g., U.S. Pat. Nos. 5,091,513; 5,132,405; and 4,946,778.

Very large naïve human scFv libraries have been and can be created to offer a large source of rearranged antibody genes against a plethora of target molecules. Smaller libraries can be constructed from individuals with infectious diseases in order to isolate disease-specific antibodies. (See Barbas et al., Proc. Natl. Acad. Sci. USA 89:9339-43 (1992); Zebedee et al., Proc. Natl. Acad. Sci. USA 89:3175-79 (1992)).

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. The term "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." CDRs for the VH and VL regions of the scFv antibodies are shown in FIG. 2.

As used herein, the term "epitope" includes any protein determinant capable of specific binding to an immunoglobulin, a scFv, or a T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to a PD-L1 epitope when the equilibrium binding constant ($K_d$) is ≤10 μM, preferably ≤10 nM, more preferably ≤10 nM, and most preferably ≤100 pM to about 1 pM, as measured by assays such as radioligand binding assays or similar assays known to those skilled in the art.

An PD-L1 protein of the invention, or a derivative, fragment, analog, homolog or ortholog thereof, may be utilized as an immunogen in the generation of antibodies that immunospecifically bind these protein components. A PD-L1 protein or a derivative, fragment, analog, homolog, or ortholog thereof, coupled to a proteoliposome may be utilized as an immunogen in the generation of antibodies that immunospecifically bind these protein components.

Those skilled in the art will recognize that it is possible to determine, without undue experimentation, if a human monoclonal antibody has the same specificity as a human monoclonal antibody of the invention by ascertaining whether the former prevents the latter from binding to PD-L1. If the human monoclonal antibody being tested competes with the human monoclonal antibody of the invention, as shown by a decrease in binding by the human monoclonal antibody of the invention, then it is likely that the two monoclonal antibodies bind to the same, or to a closely related, epitope.

Another way to determine whether a human monoclonal antibody has the specificity of a human monoclonal antibody of the invention is to pre-incubate the human monoclonal antibody of the invention with the PD-L1 protein, with which it is normally reactive, and then add the human monoclonal antibody being tested to determine if the human monoclonal antibody being tested is inhibited in its ability to bind PD-L1. If the human monoclonal antibody being tested is inhibited then, in all likelihood, it has the same, or functionally equivalent, epitopic specificity as the monoclonal antibody of the invention. Screening of human monoclonal antibodies of the invention can be also carried out by utilizing PD-L1 and determining whether the test monoclonal antibody is able to neutralize PD-L1.

Various procedures known within the art may be used for the production of polyclonal or monoclonal antibodies directed against a protein of the invention, or against derivatives, fragments, analogs homologs or orthologs thereof (See, for example, Antibodies: A Laboratory Manual, Harlow E, and Lane D, 1988, Cold Spring Harbor Laboratory Press, Cold Spring Harbor, N.Y., incorporated herein by reference).

Antibodies can be purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

The term "monoclonal antibody" or "MAb" or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

Monoclonal antibodies can be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, *Monoclonal Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Fully human antibodies are antibody molecules in which the entire sequence of both the light chain and the heavy chain, including the CDRs, arise from human genes. Such antibodies are termed "humanized antibodies", "human antibodies", or "fully human antibodies" herein. Human monoclonal antibodies can be prepared by using trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with *Epstein Barr Virus* in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries. (See Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al., Bio/Technology 10, 779-783 (1992); Lonberg et al., Nature 368 856-859 (1994); Morrison, Nature 368, 812-13 (1994); Fishwild et al, Nature Biotechnology 14, 845-51 (1996); Neuberger, Nature Biotechnology 14, 826 (1996); and Lonberg and Huszar, Intern. Rev. Immunol. 13 65-93 (1995).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv (scFv) molecules.

An example of a method of producing a nonhuman host, exemplified as a mouse, lacking expression of an endogenous immunoglobulin heavy chain is disclosed in U.S. Pat. No. 5,939,598. It can be obtained by a method, which includes deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

One method for producing an antibody of interest, such as a human antibody, is disclosed in U.S. Pat. No. 5,916,771. This method includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen and a correlative method for selecting an antibody that binds immunospecifically to the relevant epitope with high affinity, are disclosed in PCT publication WO 99/53049.

The antibody can be expressed by a vector containing a DNA segment encoding the single chain antibody described above.

These can include vectors, liposomes, naked DNA, adjuvant-assisted DNA, gene gun, catheters, etc. Vectors include chemical conjugates such as described in WO 93/64701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include *moloney murine leukemia viruses*. DNA viral vectors are preferred. These vectors include pox vectors such as *orthopox* or *avipox* vectors, *herpesvirus* vectors such as a *herpes simplex I virus* (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci USA 87:1149 (1990), *Adenovirus* Vectors (see LeGal LaSalle et al., Science, 259:988 (1993); Davidson, et al., Nat. Genet 3:219 (1993); Yang, et al., J. Virol. 69:2004 (1995) and *Adeno-associated Virus* Vectors (see Kaplitt, M. G. et al., Nat. Genet. 8:148 (1994).

Pox viral vectors introduce the gene into the cells cytoplasm. *Avipox virus* vectors result in only a short term expression of the nucleic acid. *Adenovirus* vectors, *adeno-associated virus* vectors and *herpes simplex virus* (HSV) vectors are preferred for introducing the nucleic acid into neural cells. The *adenovirus* vector results in a shorter term expression (about 2 months) than *adeno-associated virus* (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g. *adenovirus*, HSV) to a desired location. Additionally, the particles can be delivered by intracerebroventricular (icv) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266:292-305 (1994)). Other methods that can be used include catheters, intravenous, parenteral, intraperitoneal and subcutaneous injection, and oral or other known routes of administration.

These vectors can be used to express large quantities of antibodies that can be used in a variety of ways. For example, to detect the presence of PD-L1 in a sample. The antibody can also be used to try to bind to and disrupt a PD-L1 activity.

Techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275-1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Heteroconjugate antibodies are also within the scope of the present invention. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the antibody of the invention with respect to effector function, so as to enhance, e.g., the effectiveness of the antibody in treating cancer. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies or to other molecules of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987)). Preferred linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxy-sulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

Use of Antibodies Against PD-L1

Antibodies specifically binding a PD-L1 protein or a fragment thereof of the invention can be administered for the treatment of cancer or other proliferative disorders. Many cancers overexpress PD-L1 and the upregulation of PD-L1 is associated with high risk prognostic factors. Overexpression of PD-L1 in tumor cells can also indicate a mechanism by which the tumor cells evade anti-tumor immunity, such as by inducing T cell exhaustion. Such cancers include renal cell carcinoma and breast cancer. Other exemplary cancers are those cancers that are associated with or utilize T cell exhaustion to evade anti-tumor T cell activity. Use of the antibody of the invention can enhance the ability of tumor antigen-specific T cells to proliferate and produce cytokines in response to stimulation with tumor antigen peptides, thereby augmenting T cell activity or anti-tumor immune response.

Antibodies specifically binding a PD-L1 protein or fragment thereof of the invention can be administered for the treatment of a chronic infection. Such chronic infections include, for example, viral, bacterial and parasitic infections. An exemplary chronic viral infection is HIV. During chronic HIV infection, HIV-specific CD8+ T cells are functionally impaired, showing a reduced capacity to produce cytokines and effector molecules as well as a diminished ability to proliferate. PD-1 is highly expressed on HIV-specific CD8+ T cells of HIV infected individuals. Use of the antibody of the invention can enhance the ability of HIV-specific T cells to proliferate and produce cytokines in response to stimulation with HIV peptides, thereby augmenting T cell activity or anti-viral immune response.

Antibodies of the invention, including bi-specific, polyclonal, monoclonal, humanized and fully human antibodies, may be used as therapeutic agents. Such agents will generally be employed to treat or prevent cancer in a subject, increase vaccine efficiency or augment a natural immune response. An antibody preparation, preferably one having high specificity and high affinity for its target antigen, is administered to the subject and will generally have an effect due to its binding with the target. Administration of the antibody may abrogate or inhibit or interfere with an activity of the PD-L1 protein.

Antibodies of the invention are capable of inducing cell death. Cell death is induced by either direct or indirect mechanisms. For instance, PD-L1 binding by the huPD-L1 antibody can lead to complement-dependent cytotoxicity (CDC). Alternatively, the huPD-L1 antibody binds PD-L1, and leads to the recruitment of a second cell type that will kill the PD-L14-expressing target cell. Exemplary mechanisms by which the huPD-L1 antibody mediates cell death by recruitment of a second cell type include, but are not limited to, antibody-dependent cellular toxicity (ADCC) and antibody dependent cellular phagocytosis (ADCP). Target PD-L1-expressing cell types comprise tumor and T cells, for example, activated T cells.

Antibodies specifically binding a PD-L1 protein or fragment thereof of the invention can be administered for the treatment of a cancer or chronic infection in the form of pharmaceutical compositions. Principles and considerations involved in preparing therapeutic compositions comprising the antibody, as well as guidance in the choice of components are provided, for example, in Remington: The Science And Practice Of Pharmacy 19th ed. (Alfonso R. Gennaro, et al., editors) Mack Pub. Co., Easton, Pa., 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

A therapeutically effective amount of an antibody of the invention relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods.

An antibody according to the invention can be used as an agent for detecting the presence of PD-L1 (or a protein or a protein fragment thereof) in a sample. Preferably, the antibody contains a detectable label. Antibodies can be polyclonal, or more preferably, monoclonal. An intact antibody, or a fragment thereof (e.g., $F_{ab}$, scFv, or $F_{(ab)2}$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA includes Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Antibodies directed against a PD-L1 protein (or a fragment thereof) may be used in methods known within the art relating to the localization and/or quantitation of a PD-L1 protein (e.g., for use in measuring levels of the PD-L1 protein within appropriate physiological samples, for use in diagnostic methods, for use in imaging the protein, and the like). In a given embodiment, antibodies specific to a PD-L1 protein, or derivative, fragment, analog or homolog thereof, that contain the antibody derived antigen binding domain, are utilized as pharmacologically active compounds (referred to hereinafter as "Therapeutics").

An antibody specific for a PD-L1 protein of the invention can be used to isolate a PD-L1 polypeptide by standard techniques, such as immunoaffinity, chromatography or immunoprecipitation. Antibodies directed against a PD-L1 protein (or a fragment thereof) can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Pharmaceutical Compositions

The antibodies or agents of the invention (also referred to herein as "active compounds"), and derivatives, fragments, analogs and homologs thereof, can be incorporated into pharmaceutical compositions suitable for administration. Such compositions typically comprise the antibody or agent and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Diagnostic Assays

The huPD-L1 antibody of the invention, when joined to a detectable moiety, provides a way for detecting "cancerous tissue" or tissue subject to aberrant cell proliferation and therefore at risk for cancer. In addition to tissue that becomes cancerous due to an in situ neoplasm, for example, the antibody-detectable moiety conjugates also provides a method of detecting cancerous metastatic tissue present in distal organs and/or tissues. Thus such tissue may be detected by contacting tissue suspected of being cancerous with the antibody-detectable moiety under appropriate conditions to cause the detectable moiety to be detected in cancerous tissue, thereby detecting the presence of cancerous tissue.

The huPD-L1 antibody of the invention, when joined to a detectable moiety, provides a way for detecting T cell exhaustion in a subject suffering from a cancer or a chronic infection. For example, the huPD-L1 antibody can be used to detect the levels of PD-L1 in a subject, wherein the levels in comparison to a reference level can indicate whether the subject is suffering from T cell exhaustion. Thus, this method can also be used to determine whether or not treatment using the huPD-L1 antibody to augment the immune response by reversing or inhibiting T cell exhaustion would be beneficial to the subject.

The detectable moieties can be conjugated directly to the antibodies or fragments, or indirectly by using, for example, a fluorescent secondary antibody. Direct conjugation can be accomplished by standard chemical coupling of, for example, a fluorophore to the antibody or antibody fragment, or through genetic engineering. Chimeras, or fusion proteins can be constructed which contain an antibody or antibody fragment coupled to a fluorescent or bioluminescent protein. For example, Casadei, et al., describe a method of making a vector construct capable of expressing a fusion protein of aequorin and an antibody gene in mammalian cells.

As used herein, the term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject (such as a biopsy), as well as tissues, cells and fluids present within a subject. That is, the detection method of the invention can be used to detect cancer, a cancer cell, or a cancer-associated cell (such as a stromal cell associated with a tumor or cancer cell) in a biological sample in vitro as well as in vivo. For example, in vitro techniques for detection of PD-L1 include enzyme linked immunosorbent assays (ELISAs), Western blots, immunoprecipitations, and immunofluorescence. Furthermore, in vivo techniques for detection of PD-L1 include introducing into a subject a labeled anti-PD-L1 antibody. For example, the antibody can be labeled with a radioactive marker whose presence and location in a subject can be detected by standard imaging techniques. In embodiments, the invention provides a non-invasive method of detecting a tumor or cancer cell in a subject. The subject is administered an antibody or scFv antibody of the invention, where the antibody is linked to a detectable moiety (i.e., any moiety capable of being detected by, e.g., fluorescent, chemical, chemiluminescent, radioactive, or other means known in the art), the antibody is allowed to localize to the tumor then is detected by observation of the detectable moiety.

In the case of "targeted" conjugates, that is, conjugates which contain a targeting moiety—a molecule or feature designed to localize the conjugate within a subject or animal at a particular site or sites, localization refers to a state when an equilibrium between bound, "localized", and unbound, "free" entities within a subject has been essentially achieved. The rate at which such equilibrium is achieved depends upon the route of administration. For example, a conjugate administered by intravenous injection to localize thrombi may achieve localization, or accumulation at the thrombi, within minutes of injection. On the other hand, a conjugate administered orally to localize an infection in the intestine may take hours to achieve localization. Alternatively, localization may simply refer to the location of the entity within the subject or animal at selected time periods after the entity is administered. By way of another example, localization is achieved when an moiety becomes distributed following administration.

In all of the above cases, a reasonable estimate of the time to achieve localization may be made by one skilled in the art. Furthermore, the state of localization as a function of time may be followed by imaging the detectable moiety (e.g., a light-emitting conjugate) according to the methods of the invention, such as with a photodetector device. The "photodetector device" used should have a high enough sensitivity to enable the imaging of faint light from within a mammal in a reasonable amount of time, and to use the signal from such a device to construct an image.

In cases where it is possible to use light-generating moieties which are extremely bright, and/or to detect light-generating fusion proteins localized near the surface of the subject or animal being imaged, a pair of "night-vision" goggles or a standard high-sensitivity video camera, such as a Silicon Intensified Tube (SIT) camera (e.g., from Hammamatsu Photonic Systems, Bridgewater, N.J.), may be used. More typically, however, a more sensitive method of light detection is required.

In extremely low light levels the photon flux per unit area becomes so low that the scene being imaged no longer appears continuous. Instead, it is represented by individual photons which are both temporally and spatially distinct form one another. Viewed on a monitor, such an image appears as scintillating points of light, each representing a single detected photon. By accumulating these detected photons in a digital image processor over time, an image can be acquired and constructed. In contrast to conventional cameras where the signal at each image point is assigned an intensity value, in photon counting imaging the amplitude of the signal carries no significance. The objective is to simply detect the presence of a signal (photon) and to count the occurrence of the signal with respect to its position over time.

At least two types of photodetector devices, described below, can detect individual photons and generate a signal which can be analyzed by an image processor. Reduced-Noise Photodetection devices achieve sensitivity by reducing the background noise in the photon detector, as opposed to amplifying the photon signal. Noise is reduced primarily by cooling the detector array. The devices include charge coupled device (CCD) cameras referred to as "backthinned", cooled CCD cameras. In the more sensitive instruments, the cooling is achieved using, for example, liquid nitrogen, which brings the temperature of the CCD array to approximately −120° C. "Backthinned" refers to an ultra-thin backplate that reduces the path length that a photon follows to be detected, thereby increasing the quantum efficiency. A particularly sensitive backthinned cryogenic CCD camera is the "TECH 512", a series 200 camera available from Photometrics, Ltd. (Tucson, Ariz.).

"Photon amplification devices" amplify photons before they hit the detection screen. This class includes CCD cameras with intensifiers, such as microchannel intensifiers. A microchannel intensifier typically contains a metal array of channels perpendicular to and co-extensive with the detection screen of the camera. The microchannel array is placed between the sample, subject, or animal to be imaged, and the camera. Most of the photons entering the channels of the array contact a side of a channel before exiting. A voltage applied across the array results in the release of many electrons from each photon collision. The electrons from such a collision exit their channel of origin in a "shotgun" pattern, and are detected by the camera.

Even greater sensitivity can be achieved by placing intensifying microchannel arrays in series, so that electrons generated in the first stage in turn result in an amplified signal of electrons at the second stage. Increases in sensitivity, however, are achieved at the expense of spatial resolution, which decreases with each additional stage of amplification. An exemplary microchannel intensifier-based single-photon detection device is the C2400 series, available from Hamamatsu.

Image processors process signals generated by photodetector devices which count photons in order to construct an image which can be, for example, displayed on a monitor or printed on a video printer. Such image processors are typically sold as part of systems which include the sensitive photon-counting cameras described above, and accordingly, are available from the same sources. The image processors are usually connected to a personal computer, such as an IBM-compatible PC or an Apple Macintosh (Apple Computer, Cupertino, Calif.), which may or may not be included as part of a purchased imaging system. Once the images are in the form of digital files, they can be manipulated by a variety of image processing programs (such as "ADOBE PHOTOSHOP", Adobe Systems, Adobe Systems, Mt. View, Calif.) and printed.

In one embodiment, the biological sample contains protein molecules from the test subject. One preferred biological sample is a peripheral blood leukocyte sample isolated by conventional means from a subject.

The invention also encompasses kits for detecting the presence of PD-L1 or a PD-L1-expressing cell in a biological sample. For example, the kit can comprise: a labeled compound or agent capable of detecting a cancer or tumor cell (e.g., an anti-PD-L1 scFv or monoclonal antibody) in a biological sample; means for determining the amount of PD-L1 in the sample; and means for comparing the amount of PD-L1 in the sample with a standard. The standard is, in some embodiments, a non-cancer cell or cell extract thereof. The compound or agent can be packaged in a suitable container. The kit can further comprise instructions for using the kit to detect cancer in a sample.

Bi-Specific Antibodies

A bi-specific antibody (bsAb) is an antibody comprising two variable domains or scFv units such that the resulting antibody recognizes two different antigens. The present invention provides for bi-specific antibodies that recognize PD-L1 and a second antigen. Exemplary second antigens include tumor associated antigens, cytokines and cell surface receptors. In some embodiments, the second antigen can be CAIX (carbonic anhydrase IX, or G250), IL-10 or CCR4. In some embodiments, the second antigen can be a cell surface receptor, wherein the cell surface receptor is CCR4, IL21R, BTLA, HVEM or TIM3.

A bi-specific antibody of the present invention comprises a heavy chain and a light chain combination or scFv of the huPD-L1 antibodies disclosed herein.

Construction of Bi-Specific Antibodies

Bi-specific antibodies of the present invention can be constructed using methods known art. In some embodiments, the bi-specific antibody is a single polypeptide wherein the two scFv fragments are joined by a long linker polypeptide, of sufficient length to allow intramolecular association between the two scFv units to form an antibody. In other embodiments, the bi-specific antibody is more than one polypeptide linked by covalent or non-covalent bonds.

Figure 5:
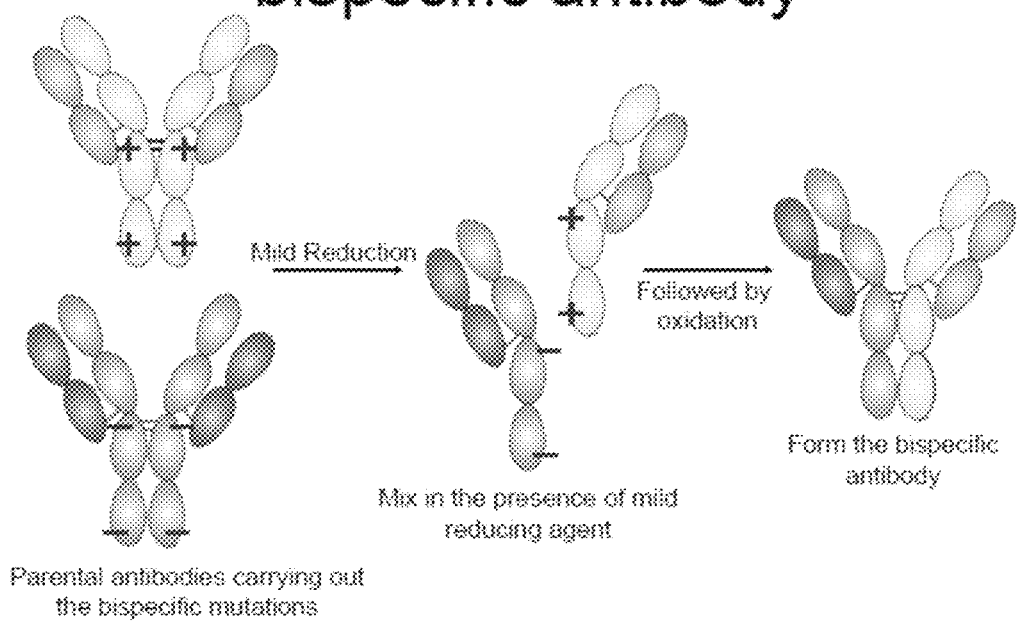
FIG. 5. Design and formation of bi-specific antibodies.
Figure 6:
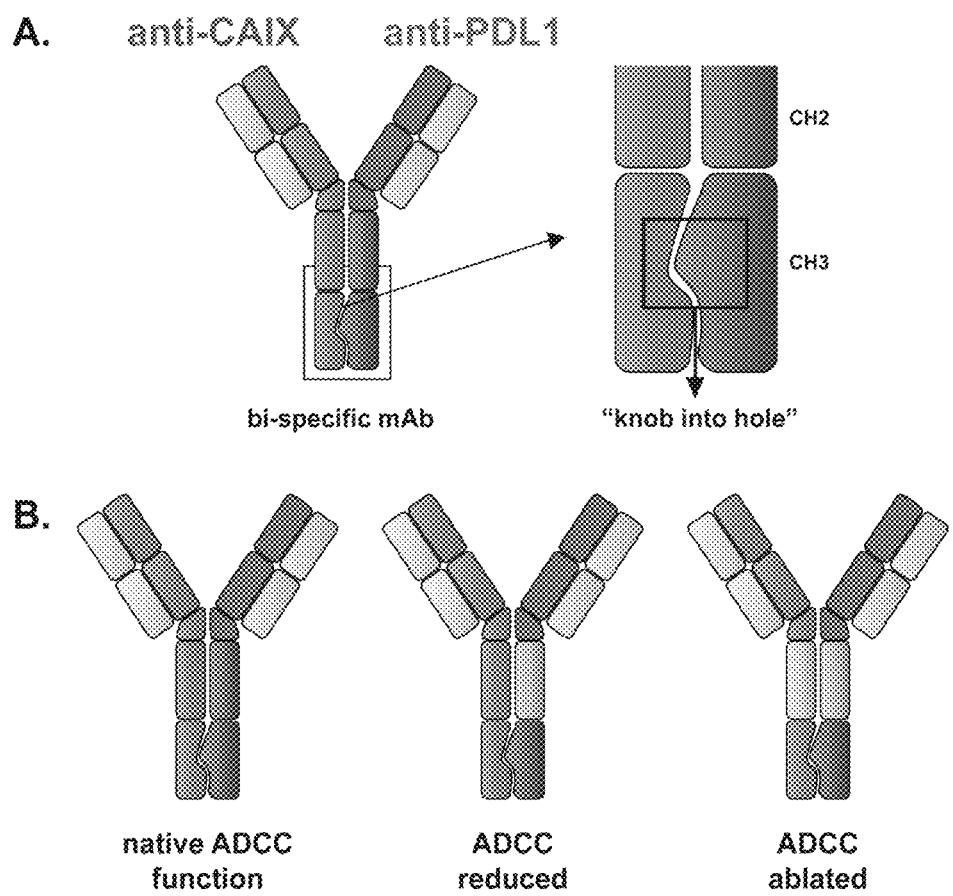
FIG. 6. Bi-specific antibody (bsAb) construct determination. A) Schematic representation of the bi-specific antibody that recognizes CAIX and PD-L1, and the "knob into hole" approach of linking the CH3 domains. B) Schematic representation of the three types of bsAb constructs with different mutations in the CH2 domain to alter ADCC activity.

In another embodiment, the bi-specific antibody is constructed using the "knob into hole" method (Ridgway et al., Protein Eng 7:617-621 (1996)). In this method, the Ig heavy chains of the two different variable domains are reduced to selectively break the heavy chain pairing while retaining the heavy-light chain pairing. The two heavy-light chain heterodimers that recognize two different antigens are mixed to promote heteroligation pairing, which is mediated through the engineered "knob into holes" of the CH3 domains, as shown in FIGS. 5 and 6A.

In another embodiment, the bi-specific antibody can be constructed through exchange of heavy-light chain dimers from two or more different antibodies to generate a hybrid antibody where the first heavy-light chain dimer recognizes PD-L1 and the second heavy-light chain dimer recognizes a second antigen. The mechanism for heavy-light chain dimer is similar to the formation of human IgG4, which also functions as a bispecific molecule. Dimerization of IgG heavy chains is driven by intramolecular force, such as the pairing the CH3 domain of each heavy chain and disulfide bridges. Presence of a specific amino acid in the CH3 domain (R409) has been shown to promote dimer exchange and construction of the IgG4 molecules. Heavy chain pairing is also stabilized further by interheavy chain disulfide bridges in the hinge region of the antibody. Specifically, in IgG4, the hinge region contains the amino acid sequence Cys-Pro-Ser-Cys (in comparison to the stable IgG1 hinge region which contains the sequence Cys-Pro-Pro-Cys) at amino acids 226-230. This sequence difference of Serine at position 229 has been linked to the tendency of IgG4 to form novel intrachain disulfides in the hinge region (Van der Neut Kolfschoten, M. et al., 2007, *Science* 317:1554-1557 and Labrijn, A. F. et al, 2011, *Journal of immunol* 187:3238-3246).

Therefore, bi-specific antibodies of the present invention can be created through introduction of the R409 residue in the CH3 domain and the Cys-Pro-Ser-Cys sequence in the hinge region of antibodies that recognize PD-L1 or a second antigen, so that the heavy-light chain dimers exchange to produce an antibody molecule with one heavy-light chain dimer recognizing PD-L1 and the second heavy-light chain dimer recognizing a second antigen, wherein the second antigen is any antigen disclosed herein. Preferably, the bi-specific antibody contains one anti-PD-L1 heavy-light chain dimer conjugated to one anti-CAIX (carbonic anhydrase IX, or 250) heavy-light chain dimer, as discussed in Examples 3 and 4. Heavy-light chain dimer exchange can also be enhanced with addition of a reducing agent, such as reduced glutathione, to promote the exchange. Known IgG4 molecules may also be altered such that the heavy and light chains recognize PD-L1 or a second antigen, as disclosed herein. Use of this method for constructing the bi-specific antibodies of the present invention may be beneficial due to the intrinsic characteristic of IgG4 molecules wherein the Fc region differs from other IgG subtypes in that it interacts poorly with effector systems of the immune response, such as complement and Fc receptors expressed by certain white blood cells. This specific property makes these IgG4-based bi-specific antibodies attractive for therapeutic applications, in which the antibody is required to bind the target(s) and functionally alter the signaling pathways associated with the target(s), however not trigger effector activities.

In some embodiments, mutations are introduced to the constant regions of the bsAb such that the antibody dependent cell-mediated cytotoxicity (ADCC) activity of the bsAb is altered. Such examples are depicted in FIG. 6B. For example, the mutation is an LALA mutation in the CH2 domain. In one aspect, the bsAb contains mutations on one scFv unit of the heterodimeric bsAb, which reduces the ADCC activity. In another aspect, the bsAb contains mutations on both chains of the heterodimeric bsAb, which completely ablates the ADCC activity. For example, the mutations introduced one or both scFv units of the bsAb are LALA mutations in the CH2 domain. These bsAbs with variable ADCC activity can be optimized such that the bsAbs exhibits maximal selective killing towards cells that express one antigen that is recognized by the bsAb, however exhibits minimal killing towards the second antigen that is recognized by the bsAb.

Exemplary Second Antigens

The present invention provides for bi-specific antibodies that recognize PD-L1 and a second antigen.

In some embodiments, the second antigen is a tumor associated antigen. In some embodiments, the tumor associated antigen is carbonic anhydrase IX (CAIX). For example, a CAIX/PD-L1 bi-specific antibody may be constructed, comprising one heavy and one light chain combination of the huPD-L1 antibodies described herein and one heavy and one light chain combination that recognizes CAIX (FIG. 5A). CAIX has been described as a prognostic marker for disease progression and a target for immunotherapy with IL-2. CAIX is a tumor-associated antigen that is highly expressed in cancers, such as renal cell carcinoma. In some cases, activation of the PD1/PD-L1 axis by tumor cells may induce T cell exhaustion for certain tumor-specific antigens, such as CAIX, whereby tumor cells expressing CAIX escape recognition by the immune system. The bsAb targeting both CAIX and PD-L1 serves as a novel cancer therapeutic. Treatment with a CAIX/PD-L1 bsAb would inhibit or reverse the PD-1/PD-L1-mediated T-cell exhaustion for CAIX, and promote tumor surveillance and an immune response against CAIX-expressing tumor cells. For example, treatment with a CAIX/PD-L1 bsAb would promote an antigen-specific immune response against tumor cells, where the antigen targeted is CAIX.

In some instances, mutations may be introduced to the CAIX or the PD-L1 chains at the constant regions (e.g., CH2 domain) to reduce ADCC activity (FIG. 5B). In some instances, mutations may be introduced into both the CAIX and the PD-L1 chains in the constant regions to completely ablate ADCC activity. Mutated bsAbs with variable ADCC activity can be assayed by methods known in the art for their specificity of killing tumor cells. Preferably, the CAIX/PD-L1 bsAb will exhibit maximal selective killing of CAIX-expressing tumor cells but exhibits only minimal killing of PD-L1-expressing endogenous peripheral blood mononuclear cells (PBMCs).

In some embodiments, the second antigen is a cell surface receptor, wherein the cell surface receptor is interleukin 21 receptor (IL21R). For example, an IL21R/PD-L1 bi-specific antibody may be constructed, comprising one heavy and one light chain combination of the huPD-L1 antibodies described herein and one heavy and one light chain combination that binds IL21R in an agonistic manner. The cytokine IL21 is secreted by CD4+ T helper cells and binds to IL21R to promote several immune activation pathways, particularly, promoting the antigen-specific cytotoxicity of CTLs and the maturation, proliferation and cytotoxicity of NK cells (Sondergaard, H et al., 2009 *Tissue antigens* 74:467-479; Kasaian, M. T. et al, 2002 *Immunity* 16:559-569; and Coquet, J. M. et al, 2008 *J Immunol* 178:2827-2834). In particular, IL21 has been shown to promote activation and cytotoxic capacity against melanoma antigens (Li, Y. et al, 2005, *J Immunol* 175:2261-2269). Systemic administration IL21 has been explored for use in treating cancer and has shown some efficacy (Schmidt, H. et al, 2010 *Clinical cancer research*, 16: 5312-5319), however, some data has also shown detrimental and undesirable side effects (Grunwald, V. et al, 2011, *Acta Oncol* 50:121-126).

The IL21R/PD-L1 bsAb of the present invention binds to IL21R in an agonistic manner, thereby acting as a mimic or surrogate for the cytokine IL21. Binding by the IL21R/PD-L1 bsAb can result in activation of the IL21R-mediated pathways and subsequent promotion of antigen-specific cytotoxic immune responses against tumor cells that have induced PD-L1-mediated T-cell exhaustion. One particular benefit of treatment with the bi-specific antibody of the invention is the localization of the IL21R activation to areas where PD-1/PD-L1-mediated T cell exhaustion has occurred, for example, in the tumor microenvironment, for example near or within tumors that have induced T cell exhaustion to evade anti-tumor immune responses. In this manner, the ILR/PD-L1 bsAb promotes anti-tumor immune response in a two-pronged mechanism: 1) by reversing or inhibiting PD-1/PD-L1-mediated T cell exhaustion, and 2) by promoting IL21/IL21R-mediated activation of cytotoxic immune response, thereby inducing antigen-specific or anti-tumor immune responses and cytotoxicity.

The IL21R/PD-L1 bi-specific antibody may also have use in a vaccine for vaccination of a subject, or as a vaccine adjuvant. In the germinal center reaction (GCR), in which high-affinity antibody-secreting plasma cells and memory B cells that ensure sustained immune protection and rapid recall responses against previously encountered foreign antigens are produced, PD1 is expressed by follicular T helper cells (TFH) while PDL1 is expressed by germinal center B cells (Crotty, S. et al, 2011, *Annual review of Immunology*, 29:621-623). Overexpression of PD1 or PD-L1 inhibits the expansion of antibody-producing B cells. Use of the IL21R/PD-L1 bi-specific antibody, wherein the PD-L1 portion of the antibody inhibits the PD1/PD-L1 axis, would result in the preferential expansion of only high affinity antibodies. As IL-21 strongly promotes the transition of antigen-specific B cells to antibody-secreting plasma cells, as well as the formation and persistence of TFH activity (Crotty, S. et al, 2011, *Annual review of Immunology*, 29:621-623), a bsAb against PDL1 with IL21 surrogate or agonistic activity could act as a GCR-specific adjuvant towards promotion of high affinity antibody production against particular antigens, such as antigens administered through a vaccine, or antigens of infectious agents.

In some embodiments, the second antigen is BTLA (B and T lymphocyte attenuator protein) or HVEM (*Herpesvirus entry mediator,* also known as TNFRSF14). For example, a BTLA/PD-L1 bi-specific antibody may be constructed, comprising one heavy and one light chain combination of the huPD-L1 antibodies described herein and one heavy and one light chain combination that binds BTLA. For example, an HVEM/PD-L1 bi-specific antibody may be constructed, comprising one heavy and one light chain combination of the huPD-L1 antibodies described herein and one heavy and one light chain combination that binds HVEM, preferably, to those regions of HVEM that mediate binding with BTLA. BTLA binding to HVEM results in T cell inhibition, similar to PD1/PD-L1 interactions. The BTLA/PD-L1 or HVEM/PD-L1 bi-specific antibodies of the present invention would inhibit or prevent the association between BTLA and HVEM, and prevent BTLA/HVE-mediated T cell inhibition. BTLA inhibition promotes tumor-specific T cell responses. Therefore, treatment with the bi-specific antibodies of the present invention results in the simultaneous blockade of two distinct inhibitor pathways that limit T cell activity.

In some instances, the HVEM/PD-L1 bsAb antibody would also prevent the association between HVEM and another HVEM ligand, CD160, which has been shown to be an agonist for the survival of B cell chronic lymphocytic leukemia (BCLL) cells, and strongly inhibits CD4+ T-cell activation and function. Treatment with the HVEM/PD-L1 bi-specific antibody that also prevents HVEM/CD160 binding of the present invention results in the simultaneous blockade of two inhibitor pathways that limit T cell activity and inhibition of CD160-mediated tumor survival pathways.

In some embodiments, the second antigen is TIM3 (T-cell immunoglobulin and mucin domain 3). For example, a TIM3/PD-L1 bi-specific antibody may be constructed, comprising one heavy and one light chain combination of the huPD-L1 antibodies described herein and one heavy and one light chain combination that binds TIM3. In one aspect, the antibodies of the present invention prevent or inhibit TIM3 binding with galectin-9 (GAL9). Interaction between TIM3 and GAL9 results in inhibition of T cell function and activation of macrophages (Sakuishi, K. et al, 2010, *The Journal of experimental medicine,* 207:2187-2194 and Zhang, Y. et al, 2012, *Journal of leukocyte biology,* 91: 189-196). TIM3 has also been shown to promote the activity of myeloid derived suppressor cells (MDSC) (Dardalhon, V. et al., 2012 *Journal of leukocyte biology,* 185:1383-1392). Therefore, treatment with a bispecific antibody of the present invention, such as the TIM3/PD-L1 bsAb, would reverse and prevent T-cell exhaustion, promote tumor surveillance and inhibit generation of MDSC. Use of the TIM3/PD-L1 bsAb may be particularly beneficial for treatment of subjects that suffer from cancers with polymorphisms in TIM3, such as renal cell carcinoma and metastatic renal cell carcinoma.

The bi-specific antibodies disclosed herein may be useful in treatment of diseases or medical conditions, for example, cancer. The bi-specific antibodies of the present invention may be particularly useful in diseases or medical conditions that are associated with T cell exhaustion. In some cases, the bi-specific antibodies disclosed herein may be used as a vaccine for promoting antigen-specific immune responses. The bi-specific antibodies of the present invention will target tumors that induce T-cell exhaustion.

Methods of Treatment

The invention provides for both prophylactic and therapeutic methods of treating a subject at risk of (or susceptible to) a cancer, or other cell proliferation-related diseases or disorders. Such diseases or disorders include but are not limited to, e.g., those diseases or disorders associated with aberrant expression of PD-L1. For example, the methods are used to treat, prevent or alleviate a symptom of renal cell carcinoma or breast cancer. Alternatively, the methods are used to treat, prevent or alleviate a symptom of a cancer in which PD-L1 plays a negative regulatory role in T cell response. Alternatively, the methods are used to treat, prevent or alleviate a symptom of a solid tumor such as breast cancer, lung cancer, ovarian cancer, prostate cancer, colon cancer, cervical cancer, brain cancer, liver cancer, pancreatic cancer or stomach cancer. Alternatively, the methods are used to treat, prevent or alleviate a symptom of a cancer that has metastasized.

The invention provides for both prophylactic and therapeutic methods of treating a subject at risk of (or susceptible to) a chronic viral, bacterial or parasitic infection. Particularly, the invention provides for both prophylactic and therapeutic methods of treating a subject at risk of (or susceptible to) HIV infection or AIDS.

The invention also provides for therapeutic methods for both prophylactic and therapeutic methods of treating a subject at risk of a disease or disorder or condition associated with T-cell exhaustion or a risk of developing T-cell exhaustion. The invention also provides for therapeutic methods for both prophylactic and therapeutic methods of treating a subject at risk of a disease or disorder or condition associated with T-cell exhaustion or a risk of developing T-cell exhaustion. Such diseases or disorder include, but are not limited to HIV, AIDS, and chronic bacterial, viral or parasitic infections. Other such chronic infections include those caused by, for example, *hepatitis B virus* (HBV), *hepatitis C virus* (HCV), *herpes simplex virus* 1 (HSV-1), *H. pylori,* or *Toxoplasma gondii.*

Accordingly, in one aspect, the invention provides methods for preventing, treating or alleviating a symptom cancer or a cell proliferative disease or disorder in a subject by administering to the subject a monoclonal antibody or scFv antibody of the invention. For example, a huPD-L1 antibody may be administered in therapeutically effective amounts.

Subjects at risk for cancer or cell proliferation-related diseases or disorders include patients who have a family history of cancer or a subject exposed to a known or suspected cancer-causing agent. Administration of a prophylactic agent can occur prior to the manifestation of cancer such that the disease is prevented or, alternatively, delayed in its progression.

In another aspect, tumor cell growth is inhibited or suppressor T cell activity is decreased by contacting a cell with a PD-L1 antibody of the invention. The cell is any cell that expresses PD-L1. For example the cell is T cell.

Also included in the invention are methods of increasing or enhancing an immune response to an antigen. An immune response is increased or enhanced by administering to the subject a monoclonal antibody or scFv antibody of the invention. The immune response is augmented for example by augmenting antigen specific T effector function. The antigen is a viral (e.g. HIV), bacterial, parasitic or tumor antigen. The immune response is a natural immune response. By natural immune response is meant an immune response that is a result of an infection. The infection is a chronic infection. Increasing or enhancing an immune response to an antigen can be measured by a number of methods known in the art. For example, an immune response can be measured by measuring any one of the following: T cell activity, T cell proliferation, T cell activation, production of effector cytokines, and T cell transcriptional profile.

Alternatively, the immune response is a response induced due to a vaccination. Accordingly, in another aspect the invention provides a method of increasing vaccine efficiency by administering to the subject a monoclonal antibody or scFv antibody of the invention and a vaccine. The antibody and the vaccine are administered sequentially or concurrently. The vaccine is a tumor vaccine a bacterial vaccine or a viral vaccine.

Combinatory Methods

The invention provides treating cancer in a patient by administering two antibodies that bind to the same epitope of the PD-L1 protein or, alternatively, two different epitopes of the PD-L1 protein. Alternatively, the cancer is treated by administering a first antibody that binds to PD-L1 and a second antibody that binds to a protein other than PD-L1. For example, the other protein other than PD-L1 may include, but is not limited to, CAIX, CCR4 and IL-10. For example, the other protein other than PD-L1 is a tumor-associated antigen.

In some embodiments, the invention provides administration of a huPD-L1 antibody alone or with an additional antibody that recognizes another protein other than PD-L1, with cells that are capable of effecting or augmenting an immune response. For example, these cells may be peripheral blood mononuclear cells (PBMC), or any cell type that is found in PBMC, e.g., cytotoxic T cells, macrophages, and natural killer (NK) cells.

Additionally, the invention provides administration of an antibody that binds to the PD-L1 protein and an anti-neoplastic agent, such a small molecule, a growth factor, a cytokine or other therapeutics including biomolecules such as peptides, peptidomimetics, peptoids, polynucleotides, lipid-derived mediators, small biogenic amines, hormones, neuropeptides, and proteases. Small molecules include, but are not limited to, inorganic molecules and small organic molecules. Suitable growth factors or cytokines include an IL-2, GM-CSF, IL-12, and TNF-alpha. Small molecule libraries are known in the art. (See, Lam, Anticancer Drug Des., 12:145, 1997.)

The invention will be further described in the following examples, which do not limit the scope of the invention described in the claims.

EXAMPLES

Example 1: Generation of Human mAbs Against PD-L1

Human mAbs against human PD-L1 were generated by panning against a 27-billion member human scFv phage display library. Using full length PD-L1 in the form of paramagnetic proteoliposomes (PMPL), which assure proper orientation of the extracellular domain of PD-L1 for presentation to the library, 14 unique scFv-phage were identified that bind PD-L1. Human IgG constructs were constructed for these 14 unique scFv-phage: Ab-14, Ab-16, Ab-22, Ab-30, Ab-31, Ab-32, Ab-38, Ab-42, Ab-46, Ab-50, Ab-52, Ab-55, Ab-56 and Ab-65.

Example 2: Characterization of huPD-L1 mAbs Binding to PD-L1

Binding analysis of huPD-L1 antibodies were performed using PD-L1-expressing cells. Four types of cells were tested, including parental cell line 300.19, and transfected cell lines expressing human PD-L1 (hPD-L1), human PD-L2 (HPD-L2), and human C-type lectin domain family 2 member (hCLEC2D). The binding assays were performed in duplicate, with the results summarized below in Tables 16-19 and FIG. 2. Antibody affinity was tested by using four antibody concentrations: 10 µg/ml, 1 µg/ml, 0.1 µg/ml and 0.01 µg/ml. GF1538 and GF1757 antibodies were used as controls: GF1538 is a humanized Ab against hPD-L1, and GF1757 is a humanized Ab against hPD-L2. The secondary antibody utilized was PE-goat anti-human IgG. All values represent mean fluorescence intensity (GMFI), as detected by FACs analysis.

Results from the binding assay show that the tested huPD-L1 antibodies show highly affinity and specificity for binding PD-L1. Use of the parental cell line 300.19, which does not express human PD-L1, as a control established the basal or non-specific fluorescence (Table 16 and FIG. 2, top left). Staining of 300.19 cells that express human PD-L1 by transfection with huPD-L1 antibodies showed significantly higher mean fluorescence intensity (MFI), demonstrating that the antibodies can bind to PD-L1. Significant FMI values, even at the lowest dilution of 0.01 µg/ml of antibody, demonstrated the high affinity of the huPD-L1 for binding PD-L1 protein (Tables 17A, 17B and FIG. 2, top right). HuPD-L1 antibodies demonstrated some capacity to bind human PD-L2 or CLEC2D when expressed in 300.19 cells, as demonstrated by Tables 18A, 18B, 19A, 19B and FIG. 2, bottom two graphs). However, the MFI values obtained for staining of PD-L2 and CLE2D were not as high as the values obtained for PD-L1. Moreover, at the lower dilutions, the MFI values were not significantly higher than the basal levels, indicating that the huPD-L1 antibodies did not have high affinity or specificity for PD-L2 or CLE2D. Although a few huPD-L1 antibodies, for example Ab-42, demonstrated some cross-reactivity with PD-L2, the antibodies have significantly higher affinity and specificity for PD-L1.

TABLE 16

Staining using huPD-L1 on untransfected 300.19 cells

| | | | Cells PE-A Mean | | | |
|---|---|---|---|---|---|---|
| Well | huPD-L1 Ab # | | approx 10 ug/ml | 1 ug/ml | 0.1 ug/ml | 0.01 ug/ml |
| A1 | 14 | | 358 | 186 | 91 | 73 |
| A2 | 16 | | 269 | 105 | 79 | 67 |
| A3 | 30 | | 75 | 78 | 74 | 66 |
| A4 | 31 | | 324 | 137 | 82 | 73 |
| A5 | 42 | | 771 | 315 | 119 | 82 |
| A6 | 50 | | 145 | 95 | 70 | 71 |
| A7 | 52 | | 324 | 124 | 85 | 72 |
| A8 | 55 | | 110 | 75 | 74 | 69 |
| A9 | 1538 | GF anti-hPD-L1 | 79 | 72 | 75 | 71 |
| A10 | 1757 | GF anti-hPD-L2 | 108 | 74 | 70 | 71 |
| A11 | control hIgG | | 260 | 87 | 74 | 73 |
| A12 | Wash | | 81 | 73 | 73 | 73 |

TABLE 17A

Staining using huPD-L1 on hPD-L1-transfected 300.19 cells, assay 1 results.

| | | Cells PE-A Mean | | | |
|---|---|---|---|---|---|
| Well | huPD-L1 Ab # | approx 10 ug/ml | 1 ug/ml | 0.1 ug/ml | 0.01 ug/ml |
| E1 | 14 | 41500 | 23277 | 8095 | 1653 |
| E2 | 16 | 31837 | 8277 | 1866 | 386 |
| E3 | 30 | 47645 | 37503 | 17479 | 3509 |

TABLE 17A-continued

Staining using huPD-L1 on hPD-L1-transfected 300.19 cells, assay 1 results.

| Well | huPD-L1 Ab # | | approx 10 ug/ml | 1 ug/ml | 0.1 ug/ml | 0.01 ug/ml |
|---|---|---|---|---|---|---|
| | | | Cells PE-A Mean | | | |
| E4 | 31 | | 53790 | 44199 | 12498 | 2826 |
| E5 | 42 | | 53583 | 40923 | 14869 | 2084 |
| E6 | 50 | | 49437 | 42087 | 15083 | 2690 |
| E7 | 52 | | 28372 | 21430 | 5614 | 1073 |
| E8 | 55 | | 24422 | 9653 | 2298 | 543 |
| E9 | 1538 | GF anti-hPD-L1 | 64961 | 60765 | 27366 | 5091 |
| E10 | 1757 | GF anti-hPD-L2 | 154 | 60 | 56 | 54 |
| E11 | control hIgG | | 195 | 64 | 52 | 51 |
| E12 | wash | | 52 | 51 | 49 | 51 |

TABLE 17B

Staining using huPD-L1 on hPD-L1-transfected 300.19 cells, assay 2 results.

| Well | huPD-L1 Ab # | | approx 10 ug/ml | 1 ug/ml | 0.1 ug/ml | 0.01 ug/ml |
|---|---|---|---|---|---|---|
| | | | Cells PE-A Mean | | | |
| E1 | 14 | | 77893 | 53207 | 17715 | 3700 |
| E2 | 16 | | 60182 | 46561 | 14101 | 4218 |
| E3 | 30 | | 67252 | 61219 | 39104 | 7722 |
| E4 | 31 | | 76388 | 70951 | 37698 | 6830 |
| E5 | 42 | best | 76824 | 72143 | 49449 | 11559 |
| E6 | 50 | | 69598 | 63446 | 28694 | 5198 |
| E7 | 52 | | 37203 | 34863 | 14718 | 2689 |
| E8 | 55 | | 42433 | 26528 | 8911 | 1758 |
| E9 | 1538 hPD-L1 | | 83021 | 85450 | 47677 | 8164 |
| E11 | 1757 hPD-L2 | | 122 | 72 | 63 | 57 |
| E10 | con hIgG | | 283 | 88 | 71 | 81 |

TABLE 18A

Staining using huPD-L1 on hPD-L2-transfected 300.19 cells, assay 1 results.

| Well | huPD-L1 Ab # | | approx 10 ug/ml | 1 ug/ml | 0.1 ug/ml | 0.01 ug/ml |
|---|---|---|---|---|---|---|
| | | | Cells PE-A Mean | | | |
| A1 | 14 | | 137 | 464 | 173 | 67 |
| A2 | 16 | | 678 | 224 | 80 | 53 |
| A3 | 30 | | 60 | 52 | 49 | 50 |
| A4 | 31 | | 795 | 239 | 91 | 82 |
| A5 | 42 | | 1417 | 668 | 254 | 72 |
| A6 | 50 | | 444 | 149 | 88 | 51 |
| A7 | 52 | | 813 | 190 | 79 | 55 |
| A8 | 55 | | 132 | 69 | 55 | 51 |
| A9 | 1538 | GF anti-hPD-L1 | 60 | 50 | 62 | 51 |
| A10 | 1757 | GF anti-hPD-L2 | 104849 | 105994 | 36970 | 4810 |
| A11 | control hIgG | | 481 | 176 | 60 | 92 |
| A12 | wash | | 69 | 51 | 52 | 60 |

TABLE 18B

Staining using huPD-L1 on hPD-L2-transfected 300.19 cells, assay 2 results.

| huPD-L1 Ab # | approx 10 ug/ml | 1 ug/ml | 0.1 ug/ml | 0.01 ug/ml |
|---|---|---|---|---|
| | Cells PE-A Mean | | | |
| 14 | 1394 | 847 | 295 | 133 |
| 16 | 1502 | 858 | 317 | 129 |
| 30 | 112 | 78 | 74 | 67 |
| 31 | 1573 | 834 | 182 | 87 |
| 42 | 2310 | 1496 | 761 | 213 |
| 50 | 680 | 386 | 220 | 79 |
| 52 | 1467 | 656 | 182 | 85 |
| 55 | 440 | 200 | 82 | 69 |
| 1538 hPD-L1 | 78 | 70 | 97 | 74 |
| 1757 hPD-L2 | 132613 | 117381 | 66269 | 11160 |
| con hIgG | 443 | 118 | 77 | 71 |

TABLE 19A

Staining using huPD-L1 on hCLEC2D-transfected 300.19 cells, assay 1.

| Well | huPD-L1 Ab # | | approx 10 ug/ml | 1 ug/ml | 0.1 ug/ml | 0.01 ug/ml |
|---|---|---|---|---|---|---|
| | | | Cells PE-A Mean | | | |
| E1 | 14 | | 3629 | 1924 | 793 | 245 |
| E2 | 16 | | 2371 | 898 | 294 | 154 |
| E3 | 30 | | 283 | 161 | 153 | 144 |
| E4 | 31 | | 2954 | 870 | 360 | 153 |
| E5 | 42 | | 4669 | 2318 | 748 | 234 |
| E6 | 50 | | 1957 | 869 | 327 | 167 |
| E7 | 52 | | 3138 | 1105 | 298 | 166 |
| E8 | 55 | | 944 | 297 | 171 | 139 |
| E9 | 1538 | GF anti-hPD-L1 | 199 | 143 | 141 | 137 |
| E10 | 1757 | GF anti-hPD-L2 | 343 | 163 | 141 | 137 |
| E11 | control hIgG | | 1541 | 351 | 175 | 146 |
| E12 | wash | | 139 | 141 | 142 | 136 |

TABLE 19B

Staining using huPD-L1 on hCLEC2-transfected 300.19 cells, assay 2.

| Well | huPD-L1 Ab # | | approx 10 ug/ml | 1 ug/ml | 0.1 ug/ml | 0.01 ug/ml |
|---|---|---|---|---|---|---|
| | | | Cells PE-A Mean | | | |
| E1 | 14 | | 3629 | 1924 | 793 | 245 |
| E2 | 16 | | 2371 | 898 | 294 | 154 |
| E3 | 30 | | 283 | 161 | 153 | 144 |
| E4 | 31 | | 2954 | 870 | 360 | 153 |
| E5 | 42 | | 4669 | 2318 | 748 | 234 |
| E6 | 50 | | 1957 | 869 | 327 | 167 |
| E7 | 52 | | 3138 | 1105 | 298 | 166 |
| E8 | 55 | | 944 | 297 | 171 | 139 |
| E9 | 1538 | GF anti-hPD-L1 | 199 | 143 | 141 | 137 |
| E10 | 1757 | GF anti-hPD-L2 | 343 | 163 | 141 | 137 |
| E11 | control hIgG | | 1541 | 351 | 175 | 146 |
| E12 | wash | | 139 | 141 | 142 | 136 |

Example 2: Characterization of Anti-PD-L1 Phage-Antibodies Blocking PD/PD-L1 Binding A competitive FACS analysis was performed to characterize the inhibition of hPD1 binding to hPD-L1 by anti- PD-L1 phage antibodies. All anti-hPD-L1 antibodies were in phage-scFv form. 293T cells were transfected with a vector encoding human PD-L1 fused to human Fc region for expression of hPD-L1-Fc. In this assay, $10^{12}$ plaque-forming units (pfu) of phage-scFvs were mixed with about 0.25 mg/ml of soluble hPD-1-hFc fusion protein and then added to the hPD-L1-expressing 293T cells. After washing, the cells were incubated with FITC-anti-human IgG antibody and analyzed by FACS to measure the binding of hPD1-hFc to hPD-L1 on the cell surface.

Figure 3:
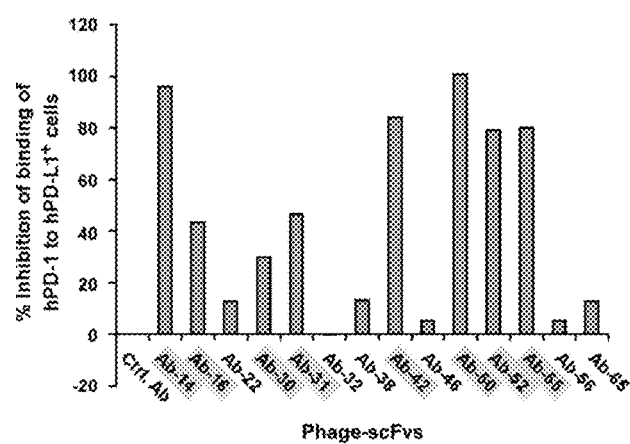
FIG. 3. Inhibition of hPD-1 binding to hPD-L1 by anti-PD-L1 phage-antibodies in a competitive FACS analysis. All anti-hPD-L1 Abs in phage-scFv form were tested for inhibition of the binding of hPD1-hFc fusion protein with hPD-L1 expressing 293T cells. $10^{12}$ pfu of phage-scFvs were mixed with ~0.25 µg/mL of soluble hPD1-hFc and added to hPD-L1 expressing-plasmid transfected 293T cells. After washing, the cells were incubated with FITC-anti-human IgG antibody to measure the binding of hPD1-hFc to hPD-L1 on cell surface.

Fluorescence values were obtained by FACS analysis and used to generate a percentage of inhibition of binding of hPD-1 to hPD-L1+ cells. These values are displayed in FIG. 3. Almost all anti-PD-L1 phage scFvs demonstrated some ability to inhibit the binding of hPD-1 to hPD-L1. Particularly, Ab-14, Ab-16, Ab-30, Ab-31, Ab-42, Ab-50, Ab-52, and Ab-55 phage-scFvs demonstrated significant inhibition of hPD-1/hPD-L1 binding.

Example 3: Characterization of huPD-L1 Soluble mAbs Blocking PD/PD-L1 Binding

Figure 4:
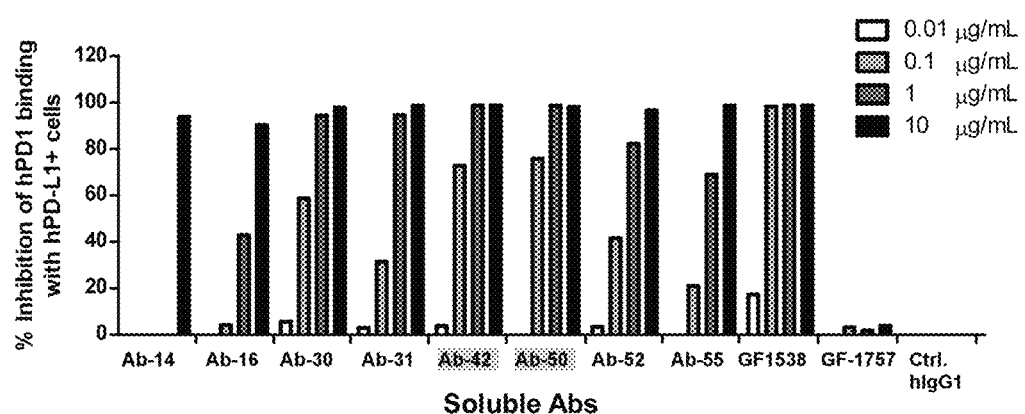
FIG. 4. Inhibition of hPD-1 binding to hPD-L1 by anti-PD-L1 soluble antibodies in a competitive FACS analysis. All anti-hPD-L1 Abs were pre-incubated with hPD-L1 expressing-plasmid transfected 300.9 cells at indicated concentrations for 30 mins, 0.125 µg of hPD-1-mouse IgG2a was then added to each reaction and incubated for another 30 mins. After washing, PE-goat-anti-mouse IgG2a Ab was added and followed by washing and FACS analysis. GF1538 is a humanized Ab against hPD-L1. GF1757 is a humanized Ab against hPD-L2.

A competitive FACS analysis was performed to characterize the inhibition of hPD1 binding to hPD-L1 by the soluble huPD-L1 antibodies of the present invention. All huPD-L1 antibodies were tested for their ability to inhibit the binding of hPD1-IgG fusion protein with hPD-L1-expressing 300.19 cells. In this assay, 50,000 cells expressing hPD-L1 were pre-incubated with the huPD-L1 or control antibodies for 30 minutes at the following concentrations: 10 μg/ml, 1 μg/ml, 0.1 μg/ml and 0.01 μg/ml. After the pre-incubation, 0.125 μg of human PD1 fused to mouse IgG2α was added to the cells and incubated for another 30 minutes. The cells were washed twice, and then 0.125 μg of goat anti-mouse IgG2α-PE antibody was added to the cells. After 30 minutes of incubation, the cells were washed twice and then analyzed by FACS. The values obtained from FACS analysis are represented as mean fluorescence intensity units (MFI) and are summarized in Table 20. MFI values from Table 20 are used to generate a percent inhibition of hPD1 binding with hPD-L1+ cells for FIG. 4. As shown herein, all of the tested huPD-L1 soluble antibodies demonstrated nearly complete inhibition of hPD1 binding with hPD-L1 at 10 μg/ml. At successively lower concentrations, most of the soluble antibodies still demonstrated very good inhibition of PD1/PD-L1 binding, particularly Ab-42 and Ab-50.

TABLE 20

Results from blocking of PD-1 binding using huPD-L1

| Well | huPD-L1 Ab # | | Cells PE-A Mean | | | |
|---|---|---|---|---|---|---|
| | | | 10 ugml | 1 ug/ml | 0.1 ug/ml | 0.01 ug/ml |
| A1 | 14 | | 696 | 11991 | 14859 | 15840 |
| A2 | 16 | | 1092 | 6660 | 11080 | 14783 |
| A3 | 30 | | 244 | 661 | 4775 | 11585 |
| A4 | 31 | | 157 | 623 | 7934 | 11908 |
| A5 | 42 | | 139 | 142 | 3137 | 11797 |
| A6 | 50 | | 207 | 156 | 2795 | 12517 |
| A7 | 52 | | 380 | 2070 | 6746 | 11856 |
| A8 | 55 | | 150 | 3625 | 9137 | 12926 |
| A9 | 1538 | GF anti-hPD-L1 | 143 | 148 | 198 | 10145 |
| A10 | 1757 | GF anti-hPD-L2 | 10922 | 11447 | 11197 | 13167 |
| A11 | control hIgG | | 11355 | 11664 | 11571 | 12274 |

TABLE 20-continued

Results from blocking of PD-1 binding using huPD-L1

| Well | huPD-L1 Ab # | | Cells PE-A Mean | | | |
|---|---|---|---|---|---|---|
| | | | 10 ugml | 1 ug/ml | 0.1 ug/ml | 0.01 ug/ml |
| A12 | wash | | 10339 | 10274 | 9842 | 12305 |
| E1 | wash neg control | | 155 | 137 | 130 | |
| E4 | mIgG2a neg control | | 128 | 207 | 131 | |
| average positive control | | | 11363 | | | |
| average negative control | | | 155 | | | |

Example 4: Formation of Bi-Specific Antibodies

Based on the role of the hinge in generating half-monomers of $IgG_4$ molecules, it was hypothesized that that introducing charged mutations in the hinge region of human $IgG_1$ may not only facilitate half-monomer exchange but also potentially stabilize the bi-specific molecule. This example demonstrates that the combination of hinge and CH3 mutations increase bi-specific antibody formation.

To further stabilize the heterodimer formation, an oppositely charged mutation was further replaced in CH3 domain, which is a concept of "Knobs-into-holes". Formation of bispecific antibodies was achieved in the following steps. First, the two parental antibodies carrying the bispecific mutations were expressed and purified separately. Then the antibodies were mixed in the presence of a mild reducing agent. The mild reduction of the antibodies caused dissociation of the antibodies into two monomers, each with a variable heavy and light chain. The monomers were then mixed together, followed by an oxidation step which causes the formation of bi-specific antibody molecules.

Bi-specific antibodies that recognize PD-L1 and G250 (Carbonic Anhydrase IX) were generated. Anti-G250 parental (G37 wild type, G37WT) and engineered (G37 KIHA) antibodies were generated and purified by two independent vectors. G37 KIHA, which conforms to a "knob-in-hole" concept and carried bispecific mutations, was altered in the sequence of immunoglobulin hinge region.

Figure 1:
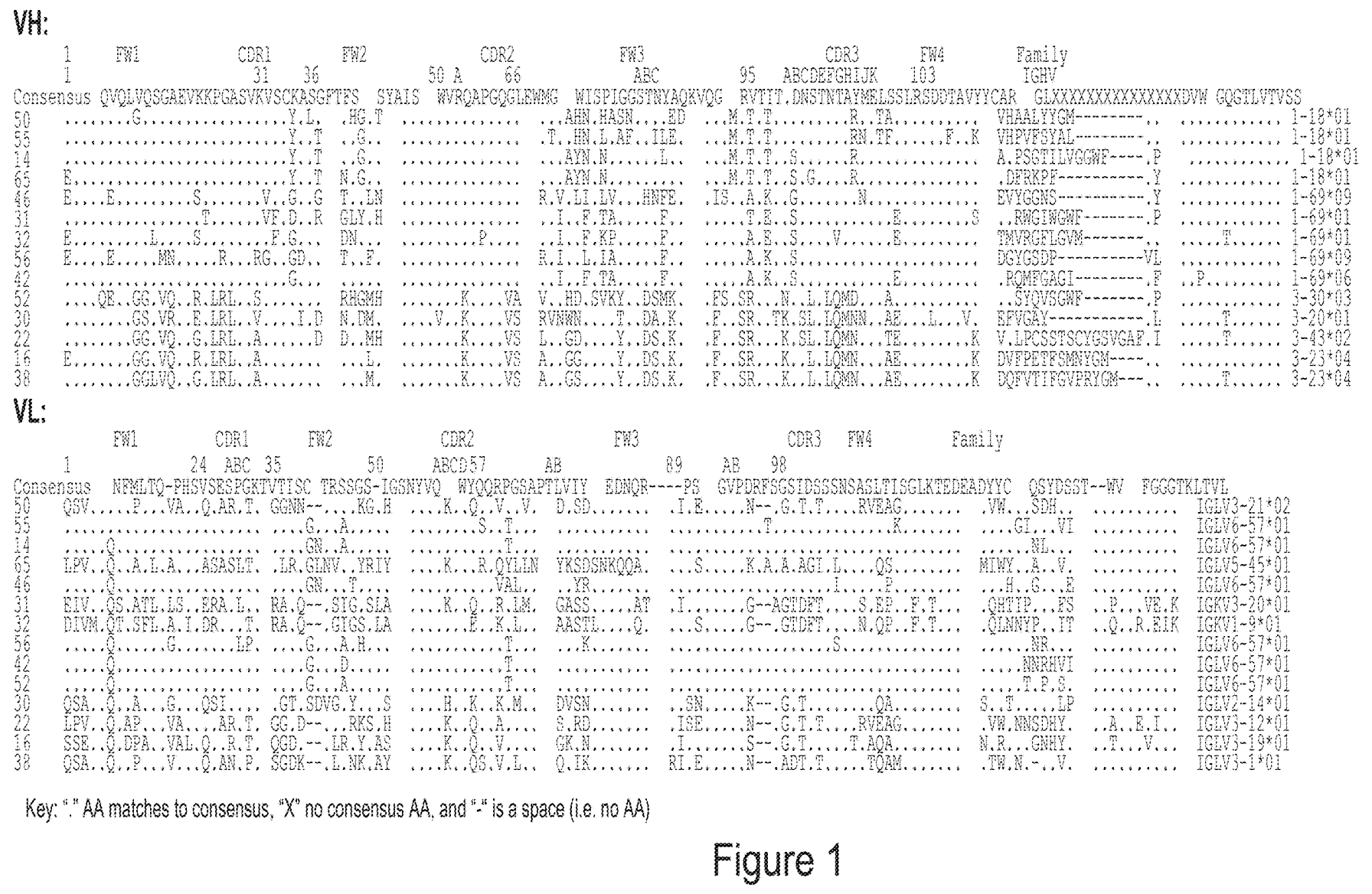

To understand the dissociation activity of G37 KIHA, antibodies were mixed in the presence of mild reducing agent to interrupt to form antibody monomer by glutathione (GSH) in different concentrations (FIG. 1A). Addition of increasing concentration of reducing agent (GSH) caused dissociation of the antibody into monomers, as indicated by the increase in the levels of the lower molecular weight species in FIG. 1A.

Figure 7A:
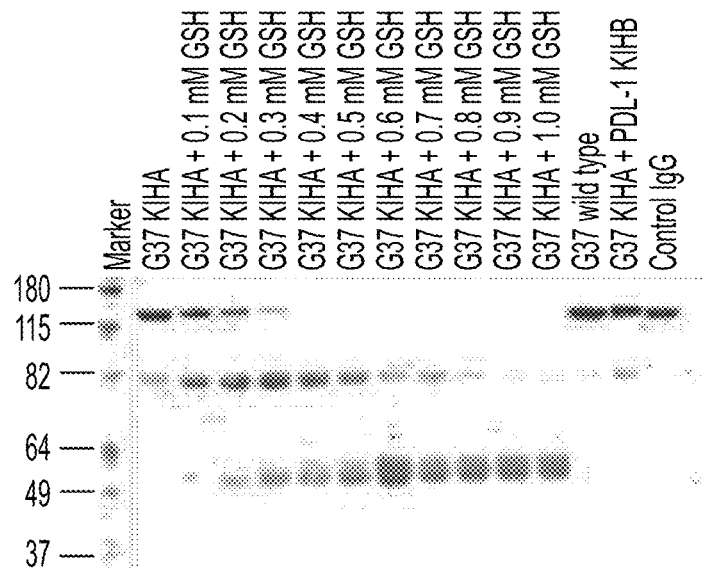
FIG. 7A, FIG. 7B and FIG. 7C. Generation of bi-specific antibody and its function.
Figure 7B:
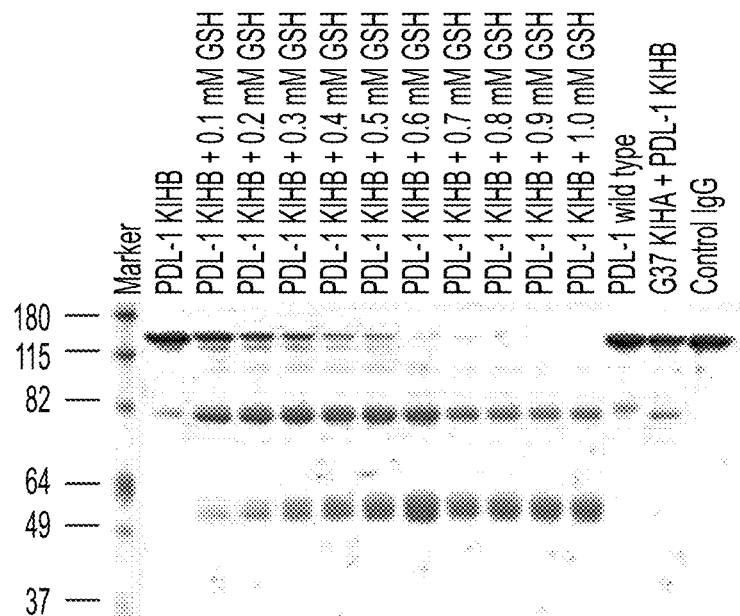
Figure 7C:
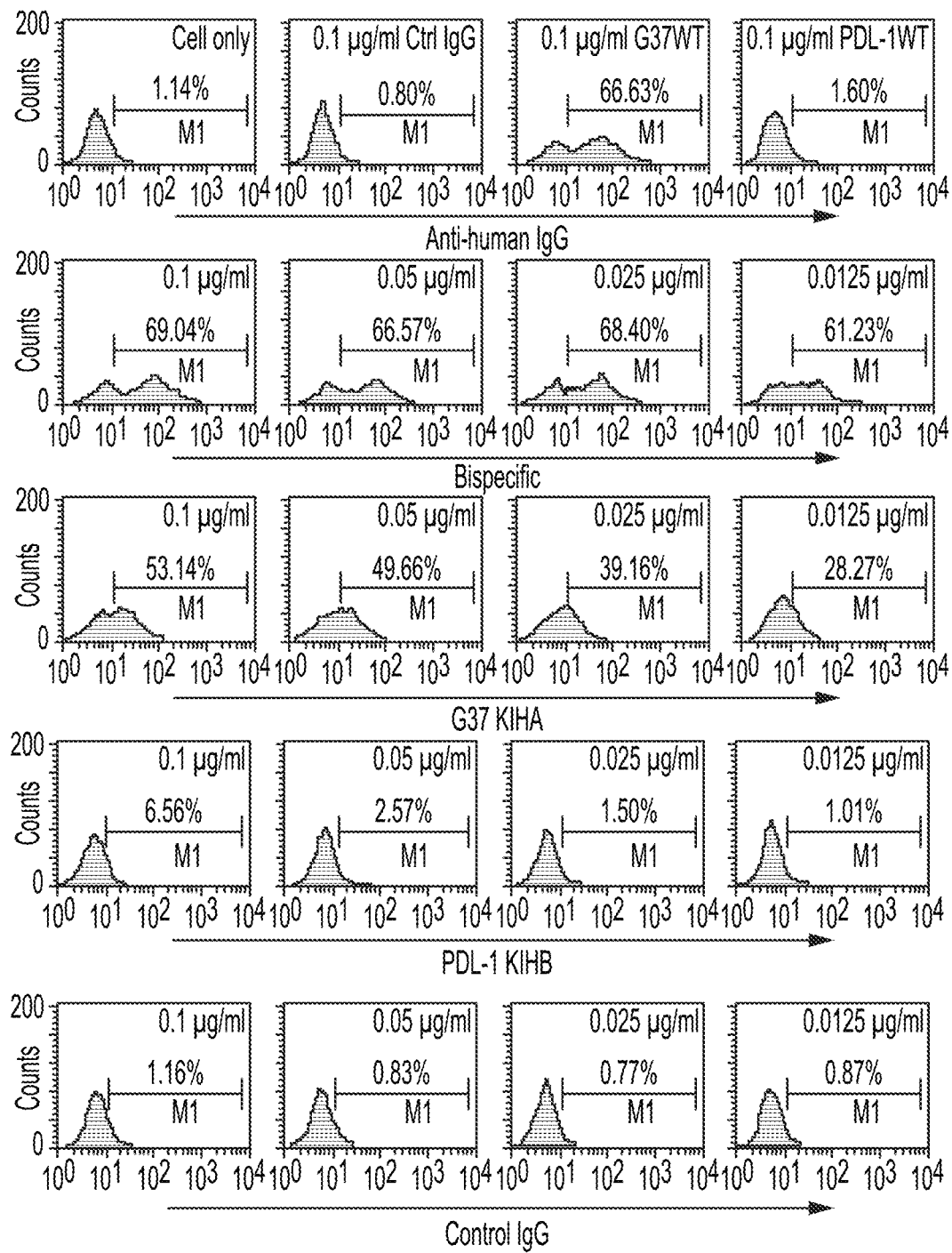

Similarly, Anti-PD-L1 parental (PD-L1 wild type, PDL-1WT) and engineered (PD-L1 KIHB) antibodies were generated and purified by two independent vectors. Using different concentrations of GSH verified the appropriate condition to obtain anti-PD-L1 monomers (FIG. 7B). The best condition of GSH concentration was selected and resulting anti-PD-L1 monomers were incubated with the G37 KIHA monomers. The formation of bispecific antibody was observed at the same size of wild type IgG, indicating that antibodies containing two heavy-light chain monomers were generated, one PD-L1-specific monomer and one G250-specific monomer.

Example 5: Bi-Specific Antibody Function

The bi-specific antibodies generated in Example 3 were next tested for their ability to recognize both antigens, for example, PD-L1 and G250. The function of the PD-L1 and G250 bi-specific antibodies was tested using flow cytometry. CAIX⁺PD-L1⁻SKRC-52 express CAIX (250) but not PD-L1, and therefore it was expected that cells could be recognized by only anti-CAIX antibody G37 and not PD-L1. To avoid the saturation of antibody binding, the concentration of antibody was low and in a reduced dose manner. Indeed, parental anti-G37 recognized SKRC-52 cells, while parental anti-PD-L1 did not (levels same as control). The bi-specific antibody, containing conjugated anti-G37 and anti-PD-L1 monomers, recognized SKRC-52 cells in a half reduced concentration compared to the parental G37 antibody, thereby demonstrating the functionality of a bi-specific antibody generated using the methods and antibodies described herein.

Example 6: Functional Characterization of mAb42

Further functional characterization of the monoclonal antibody against PD-L1 (mAb42) was performed. Peripheral blood mononuclear cells (PBMCs) were cultured from 4 different healthy donors (D1-D4). PBMCs were cultured either in the presence of mAb42 or in the presence of a control isotype IgG antibody. PMBCs were stimulated with 0.1 μg/ml SEB (*staphylococcal* enterotoxin B) and TNFα production was measured using MSD (Meso Scale Delivery). Sample analyses were performed in triplicate.

Figure 8:
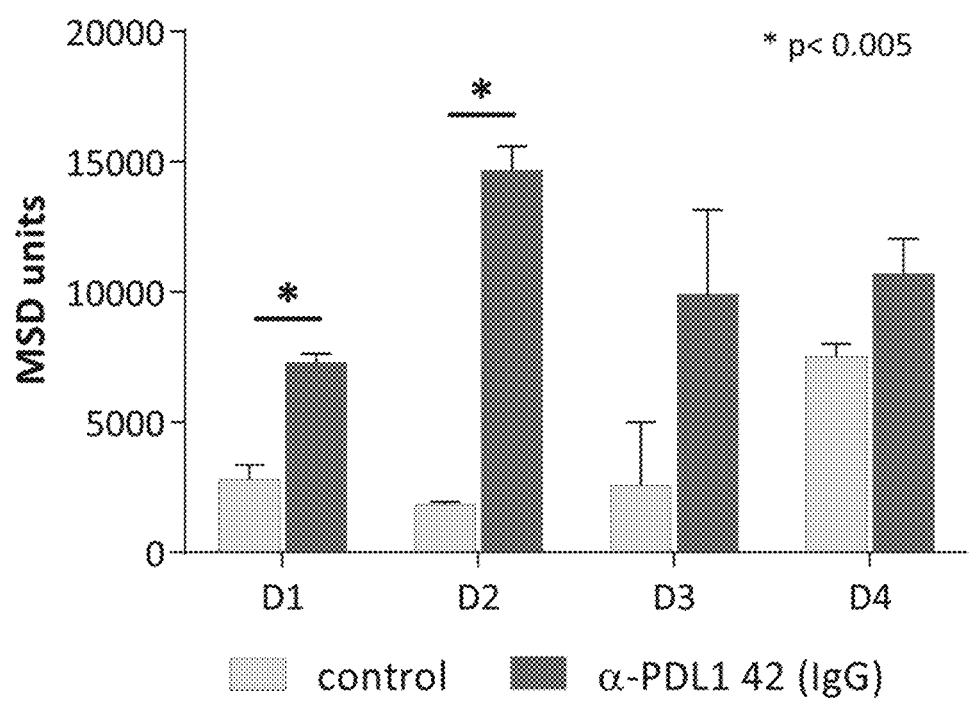
FIG. 8. Functional characterization of PD-L1 specific mAb42. PBMCs from four healthy donors (D1-D4) were cultured in the presence of αPDL1 (mAb42) or control isotype antibody stimulated with 0.1 µg/ml SEB for 48 hours and TNFα production was measured by MSD units. Data presented as means of triplicates *, p<0.0005.

As shown in FIG. 8, culturing PBMCs in the presence of mAb42 caused an increase in production of TNFα in response to SEB when cultured in the presence of anti-PD-L1 antibody (mAb42) compared to control antibody in all four donor samples. Furthermore, the increase in TNFα production was statistically significant, with a $p<0.0005$. Thus, treatment with anti-PD-L1 antibody augments the immune response in response to an antigen, or infection, in humans.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of augmenting an immune response to an antigen comprising administering to a subject in need thereof a composition comprising an isolated humanized monoclonal antibody having a heavy chain with three CDRs comprising the amino acid sequences SYAIS (SEQ ID NO:57), WIIPIFGTANYAQKFED (SEQ ID NO:78), and GRQMFGAGIDF (SEQ ID NO:93) respectively and a light chain with three CDRs comprising the amino acid sequences TRSSGSIDSNYVQ (SEQ ID NO:108), EDNQRPS (SEQ ID NO:115), and QSYDSNNRHVI (SEQ ID NO:134) respectively; wherein said antibody binds human Programmed Death Ligand-1, and wherein said augmentation of an immune response is an increase in TNFα production.

2. The method of claim 1, wherein said antibody is monovalent or bivalent.

3. The method of claim 1, wherein said antibody is a single chain antibody.

4. The method of claim 1, wherein said antibody is encoded by a nucleotide sequence comprising a $V_H$ nucleotide sequence comprising SEQ ID NO: 29 and a $V_L$ nucleotide sequence comprising SEQ ID NO 31.

5. The method of claim 1, wherein said antibody has a $V_H$ amino acid sequence comprising SEQ ID NO: 30 and a $V_L$ amino acid sequence comprising SEQ ID NO: 32.

6. The method of claim 1, wherein said antibody is a bi-specific antibody that also binds to a tumor-associated antigen, a cytokine or a cell surface receptor.

7. The method of claim 6, wherein said tumor-associated antigen is CAIX.

8. The method of claim 6, wherein said cytokine is IL-10.

9. The method of claim 6, wherein said cell surface receptor is CCR4, IL21R, BTLA, HVEM or TIM3.

10. The method according to claim 1, wherein said antibody is linked to a therapeutic agent.

11. The method of claim 10, wherein said therapeutic agent comprises a toxin, a radiolabel, a siRNA, a small molecule, or a cytokine.

12. The method of claim 1, wherein said antigen is a viral antigen, a bacterial antigen or a tumor associated antigen.

13. The method of claim 12 wherein said viral antigen is HIV.

14. The method of claim 12, wherein said tumor associated antigen is CAIX.

15. The method of claim 1, wherein said antibody is administered prior to or after exposure to the antigen.

* * * * *

SEQUENCE LISTING

```
<160> NUMBER OF SEQ ID NOS: 140

<210> SEQ ID NO 1
<211> LENGTH: 372
<212> TYPE: DNA
<213> ORGANISM: Artificial Sequence
<220> FEATURE:
<223> OTHER INFORMATION: Variable heavy chain of Ab-14

<400> SEQUENCE: 1
caggtgcagc tggtgcagtc tggagctgag gtgaagaagc ctggggcctc agtgaaggtc      60
tcctgcaagg cttctggtta caccttacc agctatggta tcagctgggt gcgacaggcc     120
cctggacaag ggcttgagtg gatgggatgg atcagcgctt acaatggtaa cacaaactat     180
gcacagaagc tccagggcag agtcaccatg accacagaca catccacgag cacagcctac     240
atggagctga ggagcctgag atctgacgac acggccgtgt attactgtgc gagagctcta     300
cctagtggga ctatactggt cggaggttgg ttcgacccct ggggccaggg aaccctggtc     360
accgtctcct ca                                                          372

<210> SEQ ID NO 2
<211> LENGTH: 124
<212> TYPE: PRT
<213> ORGANISM: Artificial Sequence
<220> FEATURE:
<223> OTHER INFORMATION: Variable heavy chain of Ab-14

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80
```

```
Met Glu Leu Arg Ser Leu Arg Ser Asp Asp Thr Ala Val Tyr Tyr Cys
                85                  90                  95

Ala Arg Ala Leu Pro Ser Gly Thr Ile Leu Val Gly Gly Trp Phe Asp
            100                 105                 110

Pro Trp Gly Gln Gly Thr Leu Val Thr Val Ser Ser
        115                 120

<210> SEQ ID NO 3
<211> LENGTH: 333
<212> TYPE: DNA
<213> ORGANISM: Artificial Sequence
<220> FEATURE:
<223> OTHER INFORMATION: Variable light chain of Ab-14

<400> SEQUENCE: 3
aattttatgc tgactcagcc ccactctgtg tcggagtctc cggggaagac ggtaaccatc      60
tcctgcaccc gcagcagtgg caacattgcc agcaattatg tgcagtggta ccaacagcgc     120
ccgggcagtg cccccaccac tgtgatctat gaggataacc aaagaccctc tggggtccct     180
gatcggttct ctggctccat cgacagctcc tccaactctg cctccctcac catctctgga     240
ctgaagactg aggacgaggc tgactactac tgtcagtctt atgatagcag caatctttgg     300
gtgttcggcg agggaccaa gctgaccgtc cta                                   333

<210> SEQ ID NO 4
<211> LENGTH: 111
<212> TYPE: PRT
<213> ORGANISM: Artificial Sequence
<220> FEATURE:
<223> OTHER INFORMATION: Variable light chain of Ab-14

<400> SEQUENCE: 4

Asn Phe Met Leu Thr Gln Pro His Ser Val Ser Glu Ser Pro Gly Lys
1               5                   10                  15

Thr Val Thr Ile Ser Cys Thr Arg Ser Ser Gly Asn Ile Ala Ser Asn
            20                  25                  30

Tyr Val Gln Trp Tyr Gln Gln Arg Pro Gly Ser Ala Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn Leu Trp Val Phe Gly Gly Gly Thr Lys Leu Thr Val Leu
            100                 105                 110

<210> SEQ ID NO 5
<211> LENGTH: 372
<212> TYPE: DNA
<213> ORGANISM: Artificial Sequence
<220> FEATURE:
<223> OTHER INFORMATION: Variable heavy chain of Ab-16

<400> SEQUENCE: 5
gaggtgcagc tggtgcagtc tggggggaggc gtggtccagc ctggagggtc cctgagactc      60
tcctgtgcag cctctggatt cacctttagc agctatgccc tgagctgggt ccgccaggct     120
ccagggaagg ggctggagtg gtctctcagct attagtggtg gtggtggtag cacatactac     180
```

```
gcagactccg tgaagggccg gttcaccatc tccagagaca attccaagaa cacgctgtat    240
ctgcaaatga acagcctgag agccgaggac acggccgtat attactgtgc gaaagacgtg    300
tttccagaga cttttccgat gaactacggt atggacgtct ggggccaagg aaccctggtc    360
accgtctcct ca                                                       372
```

```
<210> SEQ ID NO 6
<211> LENGTH: 124
<212> TYPE: PRT
<213> ORGANISM: Artificial Sequence
<220> FEATURE:
<223> OTHER INFORMATION: Variable heavy chain Ab-16

<400> SEQUENCE: 6
```

```
Glu Val Gln Leu Val Gln Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Ala Leu Ser Trp Val Arg Gln Ala Pro Gly Lys Gly Leu Glu Trp Val
        35                  40                  45

Ser Ala Ile Ser Gly Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Lys Asp Val Phe Pro Glu Thr Phe Ser Met Asn Tyr Gly Met Asp
            100                 105                 110

Val Trp Gly Gln Gly Thr Leu Val Thr Val Ser Ser
        115                 120
```

```
<210> SEQ ID NO 7
<211> LENGTH: 324
<212> TYPE: DNA
<213> ORGANISM: Artificial Sequence
<220> FEATURE:
<223> OTHER INFORMATION: Variable light chain of Ab-16

<400> SEQUENCE: 7
```

```
tcttctgagc tgactcagga ccctgctgtg tctgtggcct tgggacagac agtcaggatc    60
acatgccaag agacagcct cagaagctat tatgcaagct ggtaccagca gaagccagga   120
caggcccctg tacttgtcat ctatggtaaa acaaccggc cctcaggat cccagaccga   180 ttctctggct ccagctcagg aaacacagct tccttgacca tcactggggc tcaggcggaa   240
gatgaggctg actattactg taactcccgg gacagcagtg gtaaccatta tgtcttcgga   300
actgggacca aggtcaccgt ccta                                         324
```

```
<210> SEQ ID NO 8
<211> LENGTH: 108
<212> TYPE: PRT
<213> ORGANISM: Artificial Sequence
<220> FEATURE:
<223> OTHER INFORMATION: Variable light chain of Ab-16

<400> SEQUENCE: 8
```

```
Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Ala
            20                  25                  30
```

Ser Trp Tyr Gln Gln Lys Pro Gly Gln Ala Pro Val Leu Val Ile Tyr
         35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Tyr Val Phe Gly Thr Gly Thr Lys Val Thr Val Leu
            100                 105

<210> SEQ ID NO 9
<211> LENGTH: 384
<212> TYPE: DNA
<213> ORGANISM: Artificial Sequence
<220> FEATURE:
<223> OTHER INFORMATION: Variable heavy chain of Ab-22

<400> SEQUENCE: 9
caggtgcagc tggtgcagtc tgggggaggc gtggtacagc ctggggggtc cctgagactc      60
tcctgtgcag cctctggatt cacctttgat gattatgcca tgcactgggt ccgtcaagct     120
ccagggaagg gtctggagtg ggtctctctt attagtgggg atggtggtag cacatactat     180
gcagactctg tgaagggccg attcaccatc tccagagaca acagcaaaaa ctccctgtat     240
ctgcaaatga acagtctgag aactgaggac accgccttgt attactgtgc aaaagtgctc     300
ctcccctgta gtagtaccag ctgctatgga agcgtcggtg cttttgatat ctggggccaa     360
gggaccacgg tcaccgtctc ctca                                            384

<210> SEQ ID NO 10
<211> LENGTH: 128
<212> TYPE: PRT
<213> ORGANISM: Artificial Sequence
<220> FEATURE:
<223> OTHER INFORMATION: Variable heavy chain of Ab-22

<400> SEQUENCE: 10

Gln Val Gln Leu Val Gln Ser Gly Gly Gly Val Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Leu Ile Ser Gly Asp Gly Gly Ser Thr Tyr Tyr Ala Asp Ser Val
    50                  55                  60

Lys Gly Arg Phe Thr Ile Ser Arg Asp Asn Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Lys Val Leu Leu Pro Cys Ser Ser Thr Ser Cys Tyr Gly Ser Val
            100                 105                 110

Gly Ala Phe Asp Ile Trp Gly Gln Gly Thr Thr Val Thr Val Ser Ser
        115                 120                 125

<210> SEQ ID NO 11
<211> LENGTH: 324
<212> TYPE: DNA
<213> ORGANISM: Artificial Sequence
<220> FEATURE:
<223> OTHER INFORMATION: Variable light chain Ab-22

<400> SEQUENCE: 11

```
taggacgatg agctcggtcc cagctccgaa gacataatga tcactattat tatcccacac    60
ctgacagtaa taatcggcct catcaccggc ttcgaccctg ctgatggtca ggtggccgt    120
gttcccagag ttggagccag agaatcgctc agagatccct gagggccggt ccctatcaga   180
gtagatgacc aacgcagggg cctggcctgg cttctgctgg taccagtgca cactcttcct   240
tccaatgtcg cttcccccac aggtaatcct ggccgtcttt cctggggcca ctgacactga   300
gggtgcctga gtcagcacag gcag                                          324
```

<210> SEQ ID NO 12
<211> LENGTH: 108
<212> TYPE: PRT
<213> ORGANISM: Artificial Sequence
<220> FEATURE:
<223> OTHER INFORMATION: Variable light chain of Ab-22

<400> SEQUENCE: 12

```
Leu Pro Val Leu Thr Gln Ala Pro Ser Val Ser Val Ala Pro Gly Lys
1               5                   10                  15
Thr Ala Arg Ile Thr Cys Gly Gly Ser Asp Ile Gly Arg Lys Ser Val
            20                  25                  30
His Trp Tyr Gln Gln Lys Pro Gly Gln Ala Pro Ala Leu Val Ile Tyr
        35                  40                  45
Ser Asp Arg Asp Arg Pro Ser Gly Ile Ser Glu Arg Phe Ser Gly Ser
    50                  55                  60
Asn Ser Gly Asn Thr Ala Thr Leu Thr Ile Ser Arg Val Glu Ala Gly
65                  70                  75                  80
Asp Glu Ala Asp Tyr Tyr Cys Gln Val Trp Asp Asn Asn Ser Asp His
                85                  90                  95
Tyr Val Phe Gly Ala Gly Thr Glu Leu Ile Val Leu
            100                 105
```

<210> SEQ ID NO 13
<211> LENGTH: 351
<212> TYPE: DNA
<213> ORGANISM: Artificial Sequence
<220> FEATURE:
<223> OTHER INFORMATION: Variable heavy chain of Ab-30

<400> SEQUENCE: 13

```
caggtgcagc tggtgcagtc tgggggaagt gtggtacggc ctggggaatc cctcagactc    60
tcctgtgtag cctctggatt catctttgat aattatgaca tgagttgggt ccgccaagtt   120
ccagggaagg gctggagtg gtctctcgt gttaattgga atggtggtag cacaacttat    180
gcagacgctg tgaagggccg attcaccatc tccagagaca caccaagaa ctccctgtat    240
ctacaaatga caacctgag agccgaagac acggccgtgt attactgtgt gcgcgagttt   300
gtcggtgctt atgatctctg ggccagggg accacggtca ccgtctcctc a             351
```

<210> SEQ ID NO 14
<211> LENGTH: 117
<212> TYPE: PRT
<213> ORGANISM: Artificial Sequence
<220> FEATURE:
<223> OTHER INFORMATION: Variable heavy chain of Ab-30

<400> SEQUENCE: 14

-continued

Gln Val Gln Leu Val Gln Ser Gly Gly Ser Val Val Arg Pro Gly Glu
1               5                   10                  15

Ser Leu Arg Leu Ser Cys Val Ala Ser Gly Phe Ile Phe Asp Asn Tyr
            20                  25                  30

Asp Met Ser Trp Val Arg Gln Val Pro Gly Lys Gly Leu Glu Trp Val
        35                  40                  45

Ser Arg Val Asn Trp Asn Gly Gly Ser Thr Thr Tyr Ala Asp Ala Val
    50                  55                  60

Lys Gly Arg Phe Thr Ile Ser Arg Asp Asn Thr Lys Asn Ser Leu Tyr
65                  70                  75                  80

Leu Gln Met Asn Asn Leu Arg Ala Glu Asp Thr Ala Val Tyr Tyr Cys
                85                  90                  95

Val Arg Glu Phe Val Gly Ala Tyr Asp Leu Trp Gly Gln Gly Thr Thr
            100                 105                 110

Val Thr Val Ser Ser
        115

<210> SEQ ID NO 15
<211> LENGTH: 327
<212> TYPE: DNA
<213> ORGANISM: Artificial Sequence
<220> FEATURE:
<223> OTHER INFORMATION: Variable light chain of Ab-30

<400> SEQUENCE: 15
cagtctgccc tgactcagcc tgcctccgtg tctgggtctc ctggacagtc gatcaccatc      60
tcctgcactg gaaccagcag tgacgttggt ggttataact atgtctcctg gtaccaacaa     120
cacccaggca agcccccaa actcatgatt tatgatgtca gtaatcggcc ctcaggggtt      180
tctaatcgct tctctggctc caagtctggc aacacggcct ccctgaccat ctctggctc     240 caggctgagg acgaggctga ttattactgc agctcatata caagcagcac tctgccgttc     300
ggcggaggga ccaagctgac cgtccta                                          327

<210> SEQ ID NO 16
<211> LENGTH: 109
<212> TYPE: PRT
<213> ORGANISM: Artificial Sequence
<220> FEATURE:
<223> OTHER INFORMATION: Variable light chain of Ab-30

<400> SEQUENCE: 16

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Thr Leu Pro Phe Gly Gly Gly Thr Lys Leu Thr Val Leu
            100                 105

```
<210> SEQ ID NO 17
<211> LENGTH: 363
<212> TYPE: DNA
<213> ORGANISM: Artificial Sequence
<220> FEATURE:
<223> OTHER INFORMATION: Variable heavy chain of Ab-31

<400> SEQUENCE: 17
caggtgcagc tggtgcagtc tggggctgag gtgaagaagc caggggccac agtgaaggtc      60
tcctgcaagg ttttggaga caccttccgc ggcctctata tacactgggt gcgacaggcc     120
cctggacaag gcttgagtg gatgggaggg atcatccta tctttggtac agcaaactac     180
gcacagaagt tccagggcag agtcacgatt accacgacg aatccacgag cacagcctac     240
atggagctga gcagcctgag atctgaggac acggccgtgt attactgtgc gagcggacta     300
cgttggggga tctggggctg gttcgacccc tggggccagg gcaccctggt caccgtctcc     360
tca                                                                  363

<210> SEQ ID NO 18
<211> LENGTH: 121
<212> TYPE: PRT
<213> ORGANISM: Artificial Sequence
<220> FEATURE:
<223> OTHER INFORMATION: Variable heavy chain of Ab-31

<400> SEQUENCE: 18

Gln Val Gln Leu Val Gln Ser Gly Ala Glu Val Lys Lys Pro Gly Ala
1               5                   10                  15

Thr Val Lys Val Ser Cys Lys Val Phe Gly Asp Thr Phe Arg Gly Leu
            20                  25                  30

Tyr Ile His Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Thr Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Gly Leu Arg Trp Gly Ile Trp Gly Trp Phe Asp Pro Trp Gly
            100                 105                 110

Gln Gly Thr Leu Val Thr Val Ser Ser
        115                 120

<210> SEQ ID NO 19
<211> LENGTH: 321
<212> TYPE: DNA
<213> ORGANISM: Artificial Sequence
<220> FEATURE:
<223> OTHER INFORMATION: Variable light chain of Ab-31

<400> SEQUENCE: 19
gaaattgtgt tgacgcagtc tccagccacc ctgtctttgt ctccagggga aagagccacc      60
ctctcctgca gggccagtca gagtattggc aacagcttag cctggtacca gcagaaacct     120
ggccaggctc ccaggctcct catgtatggt gcatccagca gggccactgg catcccagac     180
aggttcagtg gcagtggggc tgggacagac ttcactctca ccatcagcag cctagagcct     240
gaagattttg caacgtatta ctgtcagcag catactatcc caacattctc tttcggccct     300
gggaccaaag tggaagtcaa a                                               321
```

<210> SEQ ID NO 20
<211> LENGTH: 107
<212> TYPE: PRT
<213> ORGANISM: Artificial Sequence
<220> FEATURE:
<223> OTHER INFORMATION: Variable light chain of Ab-31

<400> SEQUENCE: 20

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Gly Asn Ser
            20                  25                  30

Leu Ala Trp Tyr Gln Gln Lys Pro Gly Gln Ala Pro Arg Leu Leu Met
        35                  40                  45

Tyr Gly Ala Ser Ser Arg Ala Thr Gly Ile Pro Asp Arg Phe Ser Gly
50                  55                  60

Ser Gly Ala Gly Thr Asp Phe Thr Leu Thr Ile Ser Ser Leu Glu Pro
65                  70                  75                  80

Glu Asp Phe Ala Thr Tyr Tyr Cys Gln Gln His Thr Ile Pro Thr Phe
                85                  90                  95

Ser Phe Gly Pro Gly Thr Lys Val Glu Val Lys
            100                 105
```

<210> SEQ ID NO 21
<211> LENGTH: 363
<212> TYPE: DNA
<213> ORGANISM: Artificial Sequence
<220> FEATURE:
<223> OTHER INFORMATION: Variable heavy chain of Ab-32

<400> SEQUENCE: 21

```
gaggtgcagc tggtgcagtc tggggctgag ctgaagaagc ctgggtcctc ggtgaaggtc      60
tcctgcaagg cttttggagg caccttcagt gacaatgcta tcagctgggt gcgacaggcc     120
cctggacaag ggcctgagtg gatgggggc atcattccta tctttggaaa accaaactac      180
gcacagaagt tccagggcag agtcacgatt accgcggacg aatccacgag cactgcctac     240
atggtcctga gcagcctgag atctgaggac acggccgtat attactgtgc gagaactatg     300
gttcggggct tcttggggt tatggacgtc tggggccaag gaccacggt caccgtctcc       360 tca                                                                   363
```

<210> SEQ ID NO 22
<211> LENGTH: 121
<212> TYPE: PRT
<213> ORGANISM: Artificial Sequence
<220> FEATURE:
<223> OTHER INFORMATION: Variable heavy chain of Ab-32

<400> SEQUENCE: 22

```
Glu Val Gln Leu Val Gln Ser Gly Ala Glu Leu Lys Lys Pro Gly Ser
1               5                   10                  15

Ser Val Lys Val Ser Cys Lys Ala Phe Gly Gly Thr Phe Ser Asp Asn
            20                  25                  30

Ala Ile Ser Trp Val Arg Gln Ala Pro Gly Gln Gly Pro Glu Trp Met
        35                  40                  45

Gly Gly Ile Ile Pro Ile Phe Gly Lys Pro Asn Tyr Ala Gln Lys Phe
    50                  55                  60

Gln Gly Arg Val Thr Ile Thr Ala Asp Glu Ser Thr Ser Thr Ala Tyr
65                  70                  75                  80
```

```
Met Val Leu Ser Ser Leu Arg Ser Glu Asp Thr Ala Val Tyr Tyr Cys
             85                  90                  95

Ala Arg Thr Met Val Arg Gly Phe Leu Gly Val Met Asp Val Trp Gly
            100                 105                 110

Gln Gly Thr Thr Val Thr Val Ser Ser
        115                 120

<210> SEQ ID NO 23
<211> LENGTH: 321
<212> TYPE: DNA
<213> ORGANISM: Artificial Sequence
<220> FEATURE:
<223> OTHER INFORMATION: Variable light chain of Ab-32

<400> SEQUENCE: 23
gatattgtga tgacccagac tccatccttc ctgtccgcat ccataggaga cagagtcacc      60
atcacttgcc gggccagtca gggcattggc agttatttag cctggtatca gcaaagacca     120
ggggaagccc ctaagctcct gatctatgct gcatcgactt tgcaaagtgg agtcccatca     180
aggttcagcg gcagtggatc tgggacggac ttcactctca caatcagcaa cctgcagcct     240
gaagattttg caacttatta ctgtcaacag cttaataatt acccgatcac cttcggccaa     300
gggacacgac tggagattaa a                                               321

<210> SEQ ID NO 24
<211> LENGTH: 107
<212> TYPE: PRT
<213> ORGANISM: Artificial Sequence
<220> FEATURE:
<223> OTHER INFORMATION: Variable light chain of Ab-32

<400> SEQUENCE: 24

Asp Ile Val Met Thr Gln Thr Pro Ser Phe Leu Ser Ala Ser Ile Gly
1               5                   10                  15

Asp Arg Val Thr Ile Thr Cys Arg Ala Ser Gln Gly Ile Gly Ser Tyr
            20                  25                  30

Leu Ala Trp Tyr Gln Gln Arg Pro Gly Glu Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Asn Leu Gln Pro
65                  70                  75                  80

Glu Asp Phe Ala Thr Tyr Tyr Cys Gln Gln Leu Asn Asn Tyr Pro Ile
                85                  90                  95

Thr Phe Gly Gln Gly Thr Arg Leu Glu Ile Lys
            100                 105

<210> SEQ ID NO 25
<211> LENGTH: 375
<212> TYPE: DNA
<213> ORGANISM: Artificial Sequence
<220> FEATURE:
<223> OTHER INFORMATION: Variable heavy chain of Ab-38

<400> SEQUENCE: 25
caggtgcagc tggtgcagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg gtctctcagct attagtggta gtggtggtag cacatactac    180
```

```
gcagactccg tgaagggccg gttcaccatc tccagagaca attccaagaa cacgctgtat    240
ctgcaaatga acagcctgag agccgaggac acggccgtat attactgtgc gaaagatcag    300
ttcgttacga ttttggagt gccaagatac ggtatggacg tctggggcca agggaccacg    360
gtcaccgtct cctca                                                    375
```

```
<210> SEQ ID NO 26
<211> LENGTH: 125
<212> TYPE: PRT
<213> ORGANISM: Artificial Sequence
<220> FEATURE:
<223> OTHER INFORMATION: Variable heavy chain of Ab-38

<400> SEQUENCE: 26
```

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gln Phe Val Thr Ile Phe Gly Val Pro Arg Tyr Gly Met
            100                 105                 110

Asp Val Trp Gly Gln Gly Thr Thr Val Thr Val Ser Ser
        115                 120                 125

```
<210> SEQ ID NO 27
<211> LENGTH: 315
<212> TYPE: DNA
<213> ORGANISM: Artificial Sequence
<220> FEATURE:
<223> OTHER INFORMATION: Variable light chain of Ab-38

<400> SEQUENCE: 27
cagtctgccc tgactcagcc accctcagtg tccgtgtccc caggacagac agccaacatc    60
ccctgctctg gagataaatt ggggaataaa tatgcttact ggtatcagca gaagccaggc   120
cagtcccctg tactgctcat ctatcaagat atcaagcggc cctcaaggat ccctgagcga   180
ttctctggct ccaactctgc ggacacagcc actctgacca tcagcgggac ccaggctatg   240
gatgaggctg actattactg tcagacgtgg gacaacagcg tggtcttcgg cggcgggacc   300
aagctgaccg tcctc                                                   315
```

```
<210> SEQ ID NO 28
<211> LENGTH: 105
<212> TYPE: PRT
<213> ORGANISM: Artificial Sequence
<220> FEATURE:
<223> OTHER INFORMATION: Variable light chain of Ab-38

<400> SEQUENCE: 28
```

Gln Ser Ala Leu Thr Gln Pro Pro Ser Val Ser Val Ser Pro Gly Gln
1               5                   10                  15

Thr Ala Asn Ile Pro Cys Ser Gly Asp Lys Leu Gly Asn Lys Tyr Ala
            20                  25                  30

```
Tyr Trp Tyr Gln Gln Lys Pro Gly Gln Ser Pro Val Leu Leu Ile Tyr
            35                  40                  45

Gln Asp Ile Lys Arg Pro Ser Arg Ile Pro Glu Arg Phe Ser Gly Ser
 50                  55                  60

Asn Ser Ala Asp Thr Ala Thr Leu Thr Ile Ser Gly Thr Gln Ala Met
 65                  70                  75                  80

Asp Glu Ala Asp Tyr Tyr Cys Gln Thr Trp Asp Asn Ser Val Val Phe
                 85                  90                  95

Gly Gly Gly Thr Lys Leu Thr Val Leu
            100                 105

<210> SEQ ID NO 29
<211> LENGTH: 360
<212> TYPE: DNA
<213> ORGANISM: Artificial Sequence
<220> FEATURE:
<223> OTHER INFORMATION: Variable heavy chain of Ab-42

<400> SEQUENCE: 29
caggtgcagc tggtgcagtc tggggctgag gtgaagaagc ctgggtcctc ggtgaaggtc      60
tcctgcaagg cttctggagg caccttcagc agctatgcta tcagctgggt gcgacaggcc    120
cctggacaag ggcttgagtg gatgggaggg atcatcccta tctttggtac agcaaactac    180
gcacagaagt tccagggcag agtcacgatt accgcggaca aatccacgag cacagcctac    240
atggagctga gcagcctgag atctgaggac acggccgtct attactgtgc gagagggcgt    300
caaatgttcg gtgcgggaat tgatttctgg ggcccgggca ccctggtcac cgtctcctca    360

<210> SEQ ID NO 30
<211> LENGTH: 120
<212> TYPE: PRT
<213> ORGANISM: Artificial Sequence
<220> FEATURE:
<223> OTHER INFORMATION: Variable heavy chain of Ab-42

<400> SEQUENCE: 30

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Arg Gln Met Phe Gly Ala Gly Ile Asp Phe Trp Gly Pro
            100                 105                 110

Gly Thr Leu Val Thr Val Ser Ser
        115                 120

<210> SEQ ID NO 31
<211> LENGTH: 336
<212> TYPE: DNA
<213> ORGANISM: Artificial Sequence
<220> FEATURE:
<223> OTHER INFORMATION: Variable light chain of Ab-42
```

<400> SEQUENCE: 31

```
aattttatgc tgactcagcc ccactctgtg tcggagtctc cggggaagac ggtaaccatc      60
tcctgcaccc gcagcagtgg cagcattgac agcaactatg tgcagtggta ccagcagcgc     120
ccgggcagcg cccccaccac tgtgatctat gaggataacc aaagaccctc tggggtccct     180
gatcggttct ctggctccat cgacagctcc tccaactctg cctccctcac catctctgga     240
ctgaagactg aggacgaggc tgactactac tgtcagtctt atgatagcaa caatcgtcat     300
gtgatattcg gcggagggac caagctgacc gtccta                               336
```

<210> SEQ ID NO 32
<211> LENGTH: 112
<212> TYPE: PRT
<213> ORGANISM: Artificial Sequence
<220> FEATURE:
<223> OTHER INFORMATION: Variable light chain of Ab-42

<400> SEQUENCE: 32

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Asp Ser Asn
            20                  25                  30

Tyr Val Gln Trp Tyr Gln Gln Arg Pro Gly Ser Ala Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Asn Asn Arg His Val Ile Phe Gly Gly Gly Thr Lys Leu Thr Val Leu
            100                 105                 110
```

<210> SEQ ID NO 33
<211> LENGTH: 354
<212> TYPE: DNA
<213> ORGANISM: Artificial Sequence
<220> FEATURE:
<223> OTHER INFORMATION: Variable heavy chain of Ab-46

<400> SEQUENCE: 33

```
gaggtgcagc tggtggagtc tggggctgaa gtaaagaagc ctgggtcctc ggtgaaagtc      60
tcctgcaagg tttcaggagg cacattcggc acctatgctc tcaactgggt gcgccaggcc     120
cctggacaag gcttgagtg gatgggaagg atcgtccctc tcattggtct agtaaactac     180
gcacataact ttgagggcag aatctcgatt accgcgacag agtccacggg cacagcctac     240
atggaactga gcaacctgag atctgacgac acggccgtgt attactgtgc gagagaggtc     300
tacggtggta actccgacta ctgggggcag ggaaccctgg tcaccgtctc ctca            354
```

<210> SEQ ID NO 34
<211> LENGTH: 118
<212> TYPE: PRT
<213> ORGANISM: Artificial Sequence
<220> FEATURE:
<223> OTHER INFORMATION: Variable heavy chain of Ab-46

<400> SEQUENCE: 34

```
Glu Val Gln Leu Val Glu Ser Gly Ala Glu Val Lys Lys Pro Gly Ser
```

```
1               5                   10                  15
Ser Val Lys Val Ser Cys Lys Val Ser Gly Gly Thr Phe Gly Thr Tyr
                20                  25                  30

Ala Leu Asn Trp Val Arg Gln Ala Pro Gly Gln Gly Leu Glu Trp Met
                35                  40                  45

Gly Arg Ile Val Pro Leu Ile Gly Leu Val Asn Tyr Ala His Asn Phe
        50                  55                  60

Glu Gly Arg Ile Ser Ile Thr Ala Asp Lys Ser Thr Gly Thr Ala Tyr
65                  70                  75                  80

Met Glu Leu Ser Asn Leu Arg Ser Asp Asp Thr Ala Val Tyr Tyr Cys
                85                  90                  95

Ala Arg Glu Val Tyr Gly Gly Asn Ser Asp Tyr Trp Gly Gln Gly Thr
                100                 105                 110

Leu Val Thr Val Ser Ser
        115
```

<210> SEQ ID NO 35
<211> LENGTH: 330
<212> TYPE: DNA
<213> ORGANISM: Artificial Sequence
<220> FEATURE:
<223> OTHER INFORMATION: Variable light chain of Ab-46

<400> SEQUENCE: 35

```
aattttatgc tgactcagcc ccactcagtg tcggagtctc cggggaagac ggtaaccatc    60
tcctgcactc gcagtagtgg caacattggc accaactatg tgcagtggta ccagcagcgc   120
ccgggcagtg cccccgtcgc tttgatctac gaggattatc gaagaccctc tggggtccct   180
gatcggttct ctggctccat cgacagctcc tccaactctg cctccctcat catctctgga   240
ctgaagcctg aggacgaggc tgactactac tgtcagtctt atcatagcag cggttgggaa   300
ttcggcggag ggaccaagct gaccgtcctc                                    330
```

<210> SEQ ID NO 36
<211> LENGTH: 110
<212> TYPE: PRT
<213> ORGANISM: Artificial Sequence
<220> FEATURE:
<223> OTHER INFORMATION: Variable light chain of Ab-46

<400> SEQUENCE: 36

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Asn Ile Gly Thr Asn
                20                  25                  30

Tyr Val Gln Trp Tyr Gln Gln Arg Pro Gly Ser Ala Pro Val Ala Leu
                35                  40                  45

Ile Tyr Glu Asp Tyr Arg Arg Pro Ser Gly Val Pro Asp Arg Phe Ser
        50                  55                  60

Gly Ser Ile Asp Ser Ser Ser Asn Ser Ala Ser Leu Ile Ile Ser Gly
65                  70                  75                  80

Leu Lys Pro Glu Asp Glu Ala Asp Tyr Tyr Cys Gln Ser Tyr His Ser
                85                  90                  95

Ser Gly Trp Glu Phe Gly Gly Gly Thr Lys Leu Thr Val Leu
                100                 105                 110
```

<210> SEQ ID NO 37
<211> LENGTH: 360

<212> TYPE: DNA
<213> ORGANISM: Artificial Sequence
<220> FEATURE:
<223> OTHER INFORMATION: Variable heavy chain of Ab-50

<400> SEQUENCE: 37

```
caggtgcagc tggtgcagtc tggaggtgag gtgaagaagc cggggggcctc agtgaaggtc      60 tcctgcaagg cttctggtta caccttgagc agtcatggta taacctgggt gcgacaggcc     120
cctggacaag gcttgagtg gatgggatgg atcagcgctc acaatggtca cgctagcaat     180
gcacagaagg tggaggacag agtcactatg actactgaca catccacgaa cacagcctac     240
atggaactga ggagcctgac agctgacgac acggccgtgt attactgtgc gagagtacat     300
gctgccctct actatggtat ggacgtctgg ggccaaggaa ccctggtcac cgtctcctca     360
```

<210> SEQ ID NO 38
<211> LENGTH: 120
<212> TYPE: PRT
<213> ORGANISM: Artificial Sequence
<220> FEATURE:
<223> OTHER INFORMATION: Variable heavy chain of Ab-50

<400> SEQUENCE: 38

```
Gln Val Gln Leu Val Gln Ser Gly Gly Glu Val Lys Lys Pro Gly Ala
1               5                   10                  15

Ser Val Lys Val Ser Cys Lys Ala Ser Gly Tyr Thr Leu Ser Ser His
            20                  25                  30

Gly Ile Thr Trp Val Arg Gln Ala Pro Gly Gln Gly Leu Glu Trp Met
        35                  40                  45

Gly Trp Ile Ser Ala His Asn Gly His Ala Ser Asn Ala Gln Lys Val
    50                  55                  60

Glu Asp Arg Val Thr Met Thr Thr Asp Thr Ser Thr Asn Thr Ala Tyr
65                  70                  75                  80

Met Glu Leu Arg Ser Leu Thr Ala Asp Asp Thr Ala Val Tyr Tyr Cys
                85                  90                  95

Ala Arg Val His Ala Ala Leu Tyr Tyr Gly Met Asp Val Trp Gly Gln
            100                 105                 110

Gly Thr Leu Val Thr Val Ser Ser
        115                 120
```

<210> SEQ ID NO 39
<211> LENGTH: 324
<212> TYPE: DNA
<213> ORGANISM: Artificial Sequence
<220> FEATURE:
<223> OTHER INFORMATION: Variable light chain of Ab-50

<400> SEQUENCE: 39

```
cagtctgtgc tgactcagcc accctcggtg tcagtggccc caggacagac ggccaggatt      60
acctgtgggg gaaacaacat tggaagtaaa ggtgtgcact ggtatcagca gaagccaggc     120
caggcccctg tactggtcgt ctatgatgat agtgaccggc cctcagggat ccctgagcga     180
ttctctggct ccaactctgg gaacacggcc accctgacca tcagcagggt cgaagccggg     240
gatgaggccg actattactg tcaggtgtgg gatagtagta gtgatcattg ggtgttcggc     300
ggagggacca agctgaccgt ccta                                            324
```

<210> SEQ ID NO 40
<211> LENGTH: 108
<212> TYPE: PRT

```
<213> ORGANISM: Artificial Sequence
<220> FEATURE:
<223> OTHER INFORMATION: Variable light chain of Ab-50

<400> SEQUENCE: 40

Gln Ser Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Gly Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp His
                85                  90                  95

Trp Val Phe Gly Gly Gly Thr Lys Leu Thr Val Leu
            100                 105

<210> SEQ ID NO 41
<211> LENGTH: 363
<212> TYPE: DNA
<213> ORGANISM: Artificial Sequence
<220> FEATURE:
<223> OTHER INFORMATION: Variable heavy chain of Ab-52

<400> SEQUENCE: 41
caggtgcagc tgcaggagtc gggggaggc gtggtgcagc ctggagggtc cctgagactc      60
tcctgttcag cctctggatt caccttcagc agacatggca tgcactgggt ccgccaggct    120
ccaggcaagg ggctggagtg ggtggcagtg atatcacatg atggaagtgt aaaatactat    180
gcagactcca tgaagggccg attcagcatc tccagagaca attccaacaa cacactgtat    240
ctccaaatgg acagcctgag agctgacgac acggccgttt attactgtgc gagaggactg    300
tcgtaccagg tgtcggggtg gttcgacccc tggggccagg gcaccctggt caccgtctcc    360
tca                                                                  363

<210> SEQ ID NO 42
<211> LENGTH: 121
<212> TYPE: PRT
<213> ORGANISM: Artificial Sequence
<220> FEATURE:
<223> OTHER INFORMATION: Variable heavy chain of Ab-52

<400> SEQUENCE: 42

Gln Val Gln Leu Gln Glu Ser Gly Gly Gly Val Val Gln Pro Gly Arg
1               5                   10                  15

Ser Leu Arg Leu Ser Cys Ser Ala Ser Gly Phe Thr Phe Ser Arg His
            20                  25                  30

Gly Met His Trp Val Arg Gln Ala Pro Gly Lys Gly Leu Glu Trp Val
        35                  40                  45

Ala Val Ile Ser His Asp Gly Ser Val Lys Tyr Tyr Ala Asp Ser Met
    50                  55                  60

Lys Gly Arg Phe Ser Ile Ser Arg Asp Asn Ser Asn Asn Thr Leu Tyr
65                  70                  75                  80

Leu Gln Met Asp Ser Leu Arg Ala Asp Asp Thr Ala Val Tyr Tyr Cys
                85                  90                  95
```

Ala Arg Gly Leu Ser Tyr Gln Val Ser Gly Trp Phe Asp Pro Trp Gly
            100                 105                 110

Gln Gly Thr Leu Val Thr Val Ser Ser
        115                 120

<210> SEQ ID NO 43
<211> LENGTH: 333
<212> TYPE: DNA
<213> ORGANISM: Artificial Sequence
<220> FEATURE:
<223> OTHER INFORMATION: Variable light chain of Ab-52

<400> SEQUENCE: 43
aattttatgc tgactcagcc ccactctgtg tcggagtctc cggggaagac ggtaaccatc    60
tcctgcaccc gcagcagtgg cagcattgcc agcaactatg tgcagtggta ccagcagcgc   120
ccgggcagtg cccccaccac tgtgatctat gaggataacc aaagaccctc tggggtccct   180
gatcggttct ctggctccat cgacagctcc tccaactctg cctccctcac catctctgga   240
ctgaagactg aggacgaggc tgactactac tgtcagtctt atgatagcac cccccttcg    300 gtgttcggcg gcgggaccaa gctgaccgtc cta                                333

<210> SEQ ID NO 44
<211> LENGTH: 111
<212> TYPE: PRT
<213> ORGANISM: Artificial Sequence
<220> FEATURE:
<223> OTHER INFORMATION: Variable light chain of Ab-52

<400> SEQUENCE: 44

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ala Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Thr Thr Pro Ser Val Phe Gly Gly Gly Thr Lys Leu Thr Val Leu
            100                 105                 110

<210> SEQ ID NO 45
<211> LENGTH: 360
<212> TYPE: DNA
<213> ORGANISM: Artificial Sequence
<220> FEATURE:
<223> OTHER INFORMATION: Variable heavy chain of Ab-55

<400> SEQUENCE: 45
caggtgcagc tggtgcagtc tggagctgag gtgaagaagc ctggggcctc agtgaaggtc    60
tcctgcaagg cttctggtta cacctttacc agctatggta tcagctgggt gcgacaggcc   120
cctggacaag gcttgagtg gatgggatgg accagccctc ataatggtct cacagcattt    180
gcacagatcc tagagggccg agtcaccatg accacagaca catccacgaa cacagcctac   240
atggaattga ggaacctgac atttgatgac acggccgttt atttctgtgc gaaagtacat   300
cctgtcttct cttatgcgtt ggacgtctgg ggccaaggca ccctggtcac cgtctcctca        360

<210> SEQ ID NO 46
<211> LENGTH: 120
<212> TYPE: PRT
<213> ORGANISM: Artificial Sequence
<220> FEATURE:
<223> OTHER INFORMATION: Variable heavy chain of Ab-55

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Thr Ser Pro His Asn Gly Leu Thr Ala Phe Ala Gln Ile Leu
    50                  55                  60

Glu Gly Arg Val Thr Met Thr Thr Asp Thr Ser Thr Asn Thr Ala Tyr
65                  70                  75                  80

Met Glu Leu Arg Asn Leu Thr Phe Asp Asp Thr Ala Val Tyr Phe Cys
                85                  90                  95

Ala Lys Val His Pro Val Phe Ser Tyr Ala Leu Asp Val Trp Gly Gln
            100                 105                 110

Gly Thr Leu Val Thr Val Ser Ser
        115                 120

<210> SEQ ID NO 47
<211> LENGTH: 330
<212> TYPE: DNA
<213> ORGANISM: Artificial Sequence
<220> FEATURE:
<223> OTHER INFORMATION: Variable light chain of Ab-55

<400> SEQUENCE: 47
aattttatgc tgactcagcc ccactctgtg tcggagtccc cggggaagac ggtaaccatc         60
tcctgcaccc gcagcagtgg cagcattgcc agcaactatg tacagtggta ccagcagcgc        120
ccgggcagtt cccccaccac tgtgatctat gaagataacc aaagacccct ctggggtccct      180 gatcggttct ctggctccat cgacacctcc tccaactctg cctccctcac catctctgga       240
ctgaagacta aggacgaggc ggactactac tgtcagtctt atgatggcat cactgtgatt       300
ttcggcggag ggaccaagtt gaccgtccta                                         330

<210> SEQ ID NO 48
<211> LENGTH: 110
<212> TYPE: PRT
<213> ORGANISM: Artificial Sequence
<220> FEATURE:
<223> OTHER INFORMATION: Variable light chain of Ab-55

<400> SEQUENCE: 48

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Thr Ser Ser Asn Ser Ala Ser Leu Thr Ile Ser Gly
65                  70                  75                  80

Leu Lys Thr Lys Asp Glu Ala Asp Tyr Tyr Cys Gln Ser Tyr Asp Gly
                85                  90                  95

Ile Thr Val Ile Phe Gly Gly Gly Thr Lys Leu Thr Val Leu
            100                 105                 110

<210> SEQ ID NO 49
<211> LENGTH: 354
<212> TYPE: DNA
<213> ORGANISM: Artificial Sequence
<220> FEATURE:
<223> OTHER INFORMATION: Variable heavy chain of Ab-56

<400> SEQUENCE: 49

```
gaggtgcagc tggtggagtc tgagctgag gtgatgaacc ctgggtcctc ggtgagggtc      60
tcctgcaggg gttctggagg cgacttcagt acctatgctt tcagctgggt gcgacaggcc    120
cctggacaag ggcttgagtg gatgggaagg atcatcccta ccttggtat agcaaactac     180 gcacagaagt tccagggcag ggtcacgatt accgcggaca atccacgag cacagcctac     240 atggagctga gcagcctgag atctgacgat acggccgtgt attactgtgc gagagatggc    300
tatggttcgg acccggtgct atggggccag ggcaccctgg tcaccgtctc ctca          354
```

<210> SEQ ID NO 50
<211> LENGTH: 118
<212> TYPE: PRT
<213> ORGANISM: Artificial Sequence
<220> FEATURE:
<223> OTHER INFORMATION: Variable heavy chain of Ab-56

<400> SEQUENCE: 50

Glu Val Gln Leu Val Glu Ser Gly Ala Glu Val Met Asn Pro Gly Ser
1               5                   10                  15

Ser Val Arg Val Ser Cys Arg Gly Ser Gly Gly Asp Phe Ser Thr Tyr
            20                  25                  30

Ala Phe Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Asp Gly Tyr Gly Ser Asp Pro Val Leu Trp Gly Gln Gly Thr
            100                 105                 110

Leu Val Thr Val Ser Ser
        115

<210> SEQ ID NO 51
<211> LENGTH: 333
<212> TYPE: DNA
<213> ORGANISM: Artificial Sequence
<220> FEATURE:
<223> OTHER INFORMATION: Variable light chain of Ab-56

<400> SEQUENCE: 51

```
aattttatgc tgactcagcc ccactctgtg tcggggtctc cggggaagac ggtaaccctc      60
ccctgcaccc gcagcagtgg cagcattgcc agccactatg tccagtggta ccagcagcgc    120
```

```
ccgggcagtg cccccaccac tgtgatctat gaggataaca agagaccctc tggggtccct    180
gatcggttct ctggctccat cgacagctcc tccaactctg cctccctcag catctctgga    240
ctgaagactg aggacgaggc tgactactac tgtcagtctt atgatagcag caatcgttgg    300
gtgttcggcg agggaccaa gctgaccgtc cta                                   333
```

<210> SEQ ID NO 52
<211> LENGTH: 111
<212> TYPE: PRT
<213> ORGANISM: Artificial Sequence
<220> FEATURE:
<223> OTHER INFORMATION: Variable light chain of Ab-56

<400> SEQUENCE: 52

```
Asn Phe Met Leu Thr Gln Pro His Ser Val Ser Gly Ser Pro Gly Lys
1               5                   10                  15

Thr Val Thr Leu Pro Cys Thr Arg Ser Ser Gly Ser Ile Ala Ser His
            20                  25                  30

Tyr Val Gln Trp Tyr Gln Gln Arg Pro Gly Ser Ala Pro Thr Thr Val
        35                  40                  45

Ile Tyr Glu Asp Asn Lys Arg Pro Ser Gly Val Pro Asp Arg Phe Ser
    50                  55                  60

Gly Ser Ile Asp Ser Ser Ser Asn Ser Ala Ser Leu Ser Ile Ser Gly
65                  70                  75                  80

Leu Lys Thr Glu Asp Glu Ala Asp Tyr Tyr Cys Gln Ser Tyr Asp Ser
                85                  90                  95

Ser Asn Arg Trp Val Phe Gly Gly Gly Thr Lys Leu Thr Val Leu
            100                 105                 110
```

<210> SEQ ID NO 53
<211> LENGTH: 354
<212> TYPE: DNA
<213> ORGANISM: Artificial Sequence
<220> FEATURE:
<223> OTHER INFORMATION: Variable heavy chain of Ab-65

<400> SEQUENCE: 53

```
gaggtgcagc tggtgcagtc tggagctgag gtgaagaagc ctggggcctc agtgaaggtc     60
tcctgcaagg cttctggtta cacctttacc aactatggta tcagctgggt gcgacaggcc    120
cctggacaag gcttgagtg gatgggatgg atcagcgctt acaatggtaa cacaaactat    180
gcacagaagg tccagggcag agtcaccatg accacagaca catccacgag cacaggctac    240
atggagctga ggagcctgag atctgacgac acggccgtgt attactgtgc gagaggagat    300
tttcggaaac cctttgacta ctggggccag ggaaccctgg tcaccgtctc ctca           354
```

<210> SEQ ID NO 54
<211> LENGTH: 118
<212> TYPE: PRT
<213> ORGANISM: Artificial Sequence
<220> FEATURE:
<223> OTHER INFORMATION: Variable heavy chain of Ab-65

<400> SEQUENCE: 54

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Met
```

35                  40                  45
Gly Trp Ile Ser Ala Tyr Asn Gly Asn Thr Asn Tyr Ala Gln Lys Val
        50                  55                  60
Gln Gly Arg Val Thr Met Thr Thr Asp Thr Ser Thr Ser Thr Gly Tyr
65                  70                  75                  80
Met Glu Leu Arg Ser Leu Arg Ser Asp Asp Thr Ala Val Tyr Tyr Cys
                85                  90                  95
Ala Arg Gly Asp Phe Arg Lys Pro Phe Asp Tyr Trp Gly Gln Gly Thr
            100                 105                 110
Leu Val Thr Val Ser Ser
            115

<210> SEQ ID NO 55
<211> LENGTH: 345
<212> TYPE: DNA
<213> ORGANISM: Artificial Sequence
<220> FEATURE:
<223> OTHER INFORMATION: Variable light chain of Ab-65

<400> SEQUENCE: 55
ctgcctgtgc tgactcagcc ggcttccctc tctgcatccc ccggagcatc agccagtctc        60
acctgcacct tacgcagtgg cctcaatgtt ggttcctaca ggatatactg gtaccagcag       120
aagccaggga gtcgtcccca gtatctcctg aactacaaat cagactcaaa taaacagcag       180
gcctctggag tccccagccg cttctctgga tccaaggatg cttcggccaa tgcagggatt       240
ttactcatct ccgggctcca gtctgaggat gaggctgact attactgtat gatttggtac       300
agcagcgctg tggtattcgg cggagggacc aagctgaccg tccta                       345

<210> SEQ ID NO 56
<211> LENGTH: 115
<212> TYPE: PRT
<213> ORGANISM: Artificial Sequence
<220> FEATURE:
<223> OTHER INFORMATION: Variable light chain of Ab-65

<400> SEQUENCE: 56

Leu Pro Val Leu Thr Gln Pro Ala Ser Leu Ser Ala Ser Pro Gly Ala
1               5                   10                  15
Ser Ala Ser Leu Thr Cys Thr Leu Arg Ser Gly Leu Asn Val Gly Ser
            20                  25                  30
Tyr Arg Ile Tyr Trp Tyr Gln Gln Lys Pro Gly Ser Arg Pro Gln Tyr
        35                  40                  45
Leu Leu Asn Tyr Lys Ser Asp Ser Asn Lys Gln Gln Ala Ser Gly Val
    50                  55                  60
Pro Ser Arg Phe Ser Gly Ser Lys Asp Ala Ser Ala Asn Ala Gly Ile
65                  70                  75                  80
Leu Leu Ile Ser Gly Leu Gln Ser Glu Asp Glu Ala Asp Tyr Tyr Cys
                85                  90                  95
Met Ile Trp Tyr Ser Ser Ala Val Val Phe Gly Gly Gly Thr Lys Leu
            100                 105                 110
Thr Val Leu
        115

<210> SEQ ID NO 57
<211> LENGTH: 5
<212> TYPE: PRT
<213> ORGANISM: Artificial Sequence
<220> FEATURE:

<223> OTHER INFORMATION: Heavy chain CDR1 consensus, Ab-42

<400> SEQUENCE: 57

Ser Tyr Ala Ile Ser
1               5

<210> SEQ ID NO 58
<211> LENGTH: 5
<212> TYPE: PRT
<213> ORGANISM: Artificial Sequence
<220> FEATURE:
<223> OTHER INFORMATION: Heavy chain CDR1 of Ab-14, Ab-55

<400> SEQUENCE: 58

Ser Tyr Gly Ile Ser
1               5

<210> SEQ ID NO 59
<211> LENGTH: 5
<212> TYPE: PRT
<213> ORGANISM: Artificial Sequence
<220> FEATURE:
<223> OTHER INFORMATION: Heavy chain CDR1 of Ab-16

<400> SEQUENCE: 59

Ser Tyr Ala Leu Ser
1               5

<210> SEQ ID NO 60
<211> LENGTH: 5
<212> TYPE: PRT
<213> ORGANISM: Artificial Sequence
<220> FEATURE:
<223> OTHER INFORMATION: Heavy chain CDR1 of Ab-22

<400> SEQUENCE: 60

Asp Tyr Ala Met His
1               5

<210> SEQ ID NO 61
<211> LENGTH: 5
<212> TYPE: PRT
<213> ORGANISM: Artificial Sequence
<220> FEATURE:
<223> OTHER INFORMATION: Heavy chain CDR1 of Ab-30

<400> SEQUENCE: 61

Asn Tyr Asp Met Ser
1               5

<210> SEQ ID NO 62
<211> LENGTH: 5
<212> TYPE: PRT
<213> ORGANISM: Artificial Sequence
<220> FEATURE:
<223> OTHER INFORMATION: Heavy chain CDR1 of Ab-31

<400> SEQUENCE: 62

Gly Leu Tyr Ile His
1               5

<210> SEQ ID NO 63
<211> LENGTH: 5
<212> TYPE: PRT
<213> ORGANISM: Artificial Sequence
<220> FEATURE:
<223> OTHER INFORMATION: Heavy chain CDR1 of Ab-32

```
<400> SEQUENCE: 63

Asp Asn Ala Ile Ser
1               5

<210> SEQ ID NO 64
<211> LENGTH: 5
<212> TYPE: PRT
<213> ORGANISM: Artificial Sequence
<220> FEATURE:
<223> OTHER INFORMATION: Heavy chain CDR1 of Ab-38

<400> SEQUENCE: 64

Ser Tyr Ala Met Ser
1               5

<210> SEQ ID NO 65
<211> LENGTH: 5
<212> TYPE: PRT
<213> ORGANISM: Artificial Sequence
<220> FEATURE:
<223> OTHER INFORMATION: Heavy chain CDR1 of Ab-46

<400> SEQUENCE: 65

Thr Tyr Ala Leu Asn
1               5

<210> SEQ ID NO 66
<211> LENGTH: 5
<212> TYPE: PRT
<213> ORGANISM: Artificial Sequence
<220> FEATURE:
<223> OTHER INFORMATION: Heavy chain CDR1 of Ab-50

<400> SEQUENCE: 66

Ser His Gly Ile Thr
1               5

<210> SEQ ID NO 67
<211> LENGTH: 5
<212> TYPE: PRT
<213> ORGANISM: Artificial Sequence
<220> FEATURE:
<223> OTHER INFORMATION: Heavy chain CDR1 Ab-52

<400> SEQUENCE: 67

Arg His Gly Met His
1               5

<210> SEQ ID NO 68
<211> LENGTH: 5
<212> TYPE: PRT
<213> ORGANISM: Artificial Sequence
<220> FEATURE:
<223> OTHER INFORMATION: Heavy chain CDR1 of Ab-56

<400> SEQUENCE: 68

Thr Tyr Ala Phe Ser
1               5

<210> SEQ ID NO 69
<211> LENGTH: 5
<212> TYPE: PRT
<213> ORGANISM: Artificial Sequence
<220> FEATURE:
<223> OTHER INFORMATION: Heavy chain CDR1 of Ab-65
```

```
<400> SEQUENCE: 69

Asn Tyr Gly Ile Ser
1               5

<210> SEQ ID NO 70
<211> LENGTH: 17
<212> TYPE: PRT
<213> ORGANISM: Artificial Sequence
<220> FEATURE:
<223> OTHER INFORMATION: Heavy chain CDR2 consensus

<400> SEQUENCE: 70

Trp Ile Ser Pro Ile Gly Gly Ser Thr Asn Tyr Ala Gln Lys Val Gln
1               5                   10                  15

Gly

<210> SEQ ID NO 71
<211> LENGTH: 17
<212> TYPE: PRT
<213> ORGANISM: Artificial Sequence
<220> FEATURE:
<223> OTHER INFORMATION: Heavy chain CDR2 of Ab-14

<400> SEQUENCE: 71

Trp Ile Ser Ala Tyr Asn Gly Asn Thr Asn Tyr Ala Gln Lys Leu Glu
1               5                   10                  15

Asp

<210> SEQ ID NO 72
<211> LENGTH: 17
<212> TYPE: PRT
<213> ORGANISM: Artificial Sequence
<220> FEATURE:
<223> OTHER INFORMATION: Heavy chain CDR2 of Ab-16

<400> SEQUENCE: 72

Ala Ile Ser Gly Gly Gly Gly Ser Thr Tyr Tyr Ala Asp Ser Val Lys
1               5                   10                  15

Asp

<210> SEQ ID NO 73
<211> LENGTH: 17
<212> TYPE: PRT
<213> ORGANISM: Artificial Sequence
<220> FEATURE:
<223> OTHER INFORMATION: Heavy chain CDR2 of Ab-22

<400> SEQUENCE: 73

Leu Ile Ser Gly Asp Gly Gly Ser Thr Tyr Tyr Ala Asp Ser Val Lys
1               5                   10                  15

Asp

<210> SEQ ID NO 74
<211> LENGTH: 17
<212> TYPE: PRT
<213> ORGANISM: Artificial Sequence
<220> FEATURE:
<223> OTHER INFORMATION: Heavy chain CDR2 of Ab-30

<400> SEQUENCE: 74

Arg Val Asn Trp Asn Gly Gly Ser Thr Thr Tyr Ala Asp Ala Val Lys
1               5                   10                  15

Asp
```

```
<210> SEQ ID NO 75
<211> LENGTH: 17
<212> TYPE: PRT
<213> ORGANISM: Artificial Sequence
<220> FEATURE:
<223> OTHER INFORMATION: Heavy chain CDR2 of Ab-31

<400> SEQUENCE: 75

Trp Ile Ile Pro Ile Phe Gly Thr Ala Asn Tyr Ala Gln Lys Phe Glu
1               5                   10                  15

Asp

<210> SEQ ID NO 76
<211> LENGTH: 17
<212> TYPE: PRT
<213> ORGANISM: Artificial Sequence
<220> FEATURE:
<223> OTHER INFORMATION: Heavy chain CDR2 of Ab-32

<400> SEQUENCE: 76

Trp Ile Ile Pro Ile Phe Gly Lys Pro Asn Tyr Ala Gln Lys Phe Glu
1               5                   10                  15

Asp

<210> SEQ ID NO 77
<211> LENGTH: 17
<212> TYPE: PRT
<213> ORGANISM: Artificial Sequence
<220> FEATURE:
<223> OTHER INFORMATION: Heavy chain CDR2 of Ab-38

<400> SEQUENCE: 77

Ala Ile Ser Gly Ser Gly Gly Ser Thr Tyr Tyr Ala Asp Ser Val Lys
1               5                   10                  15

Asp

<210> SEQ ID NO 78
<211> LENGTH: 17
<212> TYPE: PRT
<213> ORGANISM: Artificial Sequence
<220> FEATURE:
<223> OTHER INFORMATION: Heavy chain CDR2 of Ab-42

<400> SEQUENCE: 78

Trp Ile Ile Pro Ile Phe Gly Thr Ala Asn Tyr Ala Gln Lys Phe Glu
1               5                   10                  15

Asp

<210> SEQ ID NO 79
<211> LENGTH: 17
<212> TYPE: PRT
<213> ORGANISM: Artificial Sequence
<220> FEATURE:
<223> OTHER INFORMATION: Heavy chain CDR2 of Ab-46

<400> SEQUENCE: 79

Arg Ile Val Pro Leu Ile Gly Leu Val Asn Tyr Ala His Asn Phe Glu
1               5                   10                  15

Asp

<210> SEQ ID NO 80
<211> LENGTH: 17
```

```
<212> TYPE: PRT
<213> ORGANISM: Artificial Sequence
<220> FEATURE:
<223> OTHER INFORMATION: Heavy chain CDR2 of Ab-50

<400> SEQUENCE: 80

Trp Ile Ser Ala His Asn Gly His Ala Ser Asn Ala Gln Lys Val Glu
1               5                   10                  15

Asp

<210> SEQ ID NO 81
<211> LENGTH: 17
<212> TYPE: PRT
<213> ORGANISM: Artificial Sequence
<220> FEATURE:
<223> OTHER INFORMATION: Heavy chain CDR2 of Ab-52

<400> SEQUENCE: 81

Val Ile Ser His Asp Gly Ser Val Lys Tyr Tyr Ala Asp Ser Met Lys
1               5                   10                  15

Asp

<210> SEQ ID NO 82
<211> LENGTH: 17
<212> TYPE: PRT
<213> ORGANISM: Artificial Sequence
<220> FEATURE:
<223> OTHER INFORMATION: Heavy chain CDR2 of Ab-55

<400> SEQUENCE: 82

Trp Thr Ser Pro His Asn Gly Leu Thr Ala Phe Ala Gln Ile Leu Glu
1               5                   10                  15

Asp

<210> SEQ ID NO 83
<211> LENGTH: 17
<212> TYPE: PRT
<213> ORGANISM: Artificial Sequence
<220> FEATURE:
<223> OTHER INFORMATION: Heavy chain CDR2 of Ab-56

<400> SEQUENCE: 83

Arg Ile Ile Pro Ile Leu Gly Ile Ala Asn Tyr Ala Gln Lys Phe Glu
1               5                   10                  15

Asp

<210> SEQ ID NO 84
<211> LENGTH: 17
<212> TYPE: PRT
<213> ORGANISM: Artificial Sequence
<220> FEATURE:
<223> OTHER INFORMATION: Heavy chain CDR2 of Ab-65

<400> SEQUENCE: 84

Trp Ile Ser Ala Tyr Asn Gly Asn Thr Asn Tyr Ala Gln Lys Val Glu
1               5                   10                  15

Asp

<210> SEQ ID NO 85
<211> LENGTH: 19
<212> TYPE: PRT
<213> ORGANISM: Artificial Sequence
<220> FEATURE:
<223> OTHER INFORMATION: Heavy chain CDR3 consensus
```

```
<220> FEATURE:
<221> NAME/KEY: misc_feature
<222> LOCATION: (3)..(17)
<223> OTHER INFORMATION: Xaa can be any naturally occurring amino acid

<400> SEQUENCE: 85

Gly Leu Xaa Xaa Xaa Xaa Xaa Xaa Xaa Xaa Xaa Xaa Xaa Xaa Xaa
1               5                   10                  15

Xaa Asp Val

<210> SEQ ID NO 86
<211> LENGTH: 15
<212> TYPE: PRT
<213> ORGANISM: Artificial Sequence
<220> FEATURE:
<223> OTHER INFORMATION: Heavy chain CDR3 of Ab-14

<400> SEQUENCE: 86

Ala Leu Pro Ser Gly Thr Ile Leu Val Gly Gly Trp Phe Asp Pro
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: Heavy chain CDR3 of Ab-16

<400> SEQUENCE: 87

Asp Val Phe Pro Glu Thr Phe Ser Met Asn Tyr Gly Met Asp Val
1               5                   10                  15

<210> SEQ ID NO 88
<211> LENGTH: 19
<212> TYPE: PRT
<213> ORGANISM: Artificial Sequence
<220> FEATURE:
<223> OTHER INFORMATION: Heavy chain CDR3 of Ab-22

<400> SEQUENCE: 88

Val Leu Leu Pro Cys Ser Ser Thr Ser Cys Tyr Gly Ser Val Gly Ala
1               5                   10                  15

Phe Asp Ile

<210> SEQ ID NO 89
<211> LENGTH: 8
<212> TYPE: PRT
<213> ORGANISM: Artificial Sequence
<220> FEATURE:
<223> OTHER INFORMATION: Heavy chain CDR3 of Ab-30

<400> SEQUENCE: 89

Glu Phe Val Gly Ala Tyr Asp Leu
1               5

<210> SEQ ID NO 90
<211> LENGTH: 12
<212> TYPE: PRT
<213> ORGANISM: Artificial Sequence
<220> FEATURE:
<223> OTHER INFORMATION: Heavy chain CDR3 of Ab-31

<400> SEQUENCE: 90

Gly Leu Arg Trp Gly Ile Trp Gly Trp Phe Asp Pro
1               5                   10
```

<210> SEQ ID NO 91
<211> LENGTH: 12
<212> TYPE: PRT
<213> ORGANISM: Artificial Sequence
<220> FEATURE:
<223> OTHER INFORMATION: Heavy chain CDR3 of Ab-32

<400> SEQUENCE: 91

Thr Met Val Arg Gly Phe Leu Gly Val Met Asp Val
1               5                   10

<210> SEQ ID NO 92
<211> LENGTH: 16
<212> TYPE: PRT
<213> ORGANISM: Artificial Sequence
<220> FEATURE:
<223> OTHER INFORMATION: Heavy chain CDR3 of Ab-38

<400> SEQUENCE: 92

Asp Gln Phe Val Thr Ile Phe Gly Val Pro Arg Tyr Gly Met Asp Val
1               5                   10                  15

<210> SEQ ID NO 93
<211> LENGTH: 11
<212> TYPE: PRT
<213> ORGANISM: Artificial Sequence
<220> FEATURE:
<223> OTHER INFORMATION: Heavy chain CDR3 of Ab-42

<400> SEQUENCE: 93

Gly Arg Gln Met Phe Gly Ala Gly Ile Asp Phe
1               5                   10

<210> SEQ ID NO 94
<211> LENGTH: 9
<212> TYPE: PRT
<213> ORGANISM: Artificial Sequence
<220> FEATURE:
<223> OTHER INFORMATION: Heavy chain CDR3 of Ab-46

<400> SEQUENCE: 94

Glu Val Tyr Gly Gly Asn Ser Asp Tyr
1               5

<210> SEQ ID NO 95
<211> LENGTH: 11
<212> TYPE: PRT
<213> ORGANISM: Artificial Sequence
<220> FEATURE:
<223> OTHER INFORMATION: Heavy chain CDR3 of Ab-50

<400> SEQUENCE: 95

Val His Ala Ala Leu Tyr Tyr Gly Met Asp Val
1               5                   10

<210> SEQ ID NO 96
<211> LENGTH: 12
<212> TYPE: PRT
<213> ORGANISM: Artificial Sequence
<220> FEATURE:
<223> OTHER INFORMATION: Heavy chain CDR3 of Ab-52

<400> SEQUENCE: 96

Gly Leu Ser Tyr Gln Val Ser Gly Trp Phe Asp Pro
1               5                   10

```
<210> SEQ ID NO 97
<211> LENGTH: 11
<212> TYPE: PRT
<213> ORGANISM: Artificial Sequence
<220> FEATURE:
<223> OTHER INFORMATION: Heavy chain CDR3 of Ab-55

<400> SEQUENCE: 97

Val His Pro Val Phe Ser Tyr Ala Leu Asp Val
1               5                   10

<210> SEQ ID NO 98
<211> LENGTH: 9
<212> TYPE: PRT
<213> ORGANISM: Artificial Sequence
<220> FEATURE:
<223> OTHER INFORMATION: Heavy chain CDR3 of Ab-56

<400> SEQUENCE: 98

Asp Gly Tyr Gly Ser Asp Pro Val Leu
1               5

<210> SEQ ID NO 99
<211> LENGTH: 9
<212> TYPE: PRT
<213> ORGANISM: Artificial Sequence
<220> FEATURE:
<223> OTHER INFORMATION: Heavy chain CDR3 of Ab-65

<400> SEQUENCE: 99

Gly Asp Phe Arg Lys Pro Phe Asp Tyr
1               5

<210> SEQ ID NO 100
<211> LENGTH: 13
<212> TYPE: PRT
<213> ORGANISM: Artificial Sequence
<220> FEATURE:
<223> OTHER INFORMATION: Light chain CDR1 consensus

<400> SEQUENCE: 100

Thr Arg Ser Ser Gly Ser Ile Gly Ser Asn Tyr Val Gln
1               5                   10

<210> SEQ ID NO 101
<211> LENGTH: 13
<212> TYPE: PRT
<213> ORGANISM: Artificial Sequence
<220> FEATURE:
<223> OTHER INFORMATION: Light chain CDR1 of Ab-14

<400> SEQUENCE: 101

Thr Arg Ser Ser Gly Asn Ile Ala Ser Asn Tyr Val Gln
1               5                   10

<210> SEQ ID NO 102
<211> LENGTH: 11
<212> TYPE: PRT
<213> ORGANISM: Artificial Sequence
<220> FEATURE:
<223> OTHER INFORMATION: Light chain CDR1 of Ab-16

<400> SEQUENCE: 102

Gln Gly Asp Ser Leu Arg Ser Tyr Tyr Ala Ser
1               5                   10

<210> SEQ ID NO 103
```

```
<211> LENGTH: 11
<212> TYPE: PRT
<213> ORGANISM: Artificial Sequence
<220> FEATURE:
<223> OTHER INFORMATION: Light chain CDR1 of Ab-22

<400> SEQUENCE: 103

Gly Gly Ser Asp Ile Gly Arg Lys Ser Val His
1               5                   10

<210> SEQ ID NO 104
<211> LENGTH: 14
<212> TYPE: PRT
<213> ORGANISM: Artificial Sequence
<220> FEATURE:
<223> OTHER INFORMATION: Light chain CDR1 of Ab-30

<400> SEQUENCE: 104

Thr Gly Thr Ser Ser Asp Val Gly Gly Tyr Asn Tyr Val Ser
1               5                   10

<210> SEQ ID NO 105
<211> LENGTH: 11
<212> TYPE: PRT
<213> ORGANISM: Artificial Sequence
<220> FEATURE:
<223> OTHER INFORMATION: Light chain CDR1 of Ab-31

<400> SEQUENCE: 105

Arg Ala Ser Gln Ser Ile Gly Asn Ser Leu Ala
1               5                   10

<210> SEQ ID NO 106
<211> LENGTH: 11
<212> TYPE: PRT
<213> ORGANISM: Artificial Sequence
<220> FEATURE:
<223> OTHER INFORMATION: Light chain CDR1 of Ab-32

<400> SEQUENCE: 106

Arg Ala Ser Gln Gly Ile Gly Ser Tyr Leu Ala
1               5                   10

<210> SEQ ID NO 107
<211> LENGTH: 11
<212> TYPE: PRT
<213> ORGANISM: Artificial Sequence
<220> FEATURE:
<223> OTHER INFORMATION: Light chain CDR1 of Ab-38

<400> SEQUENCE: 107

Ser Gly Asp Lys Leu Gly Asn Lys Tyr Ala Tyr
1               5                   10

<210> SEQ ID NO 108
<211> LENGTH: 13
<212> TYPE: PRT
<213> ORGANISM: Artificial Sequence
<220> FEATURE:
<223> OTHER INFORMATION: Light chain CDR1 of Ab-42

<400> SEQUENCE: 108

Thr Arg Ser Ser Gly Ser Ile Asp Ser Asn Tyr Val Gln
1               5                   10

<210> SEQ ID NO 109
<211> LENGTH: 13
```

```
<212> TYPE: PRT
<213> ORGANISM: Artificial Sequence
<220> FEATURE:
<223> OTHER INFORMATION: Light chain CDR1 of Ab-46

<400> SEQUENCE: 109

Thr Arg Ser Ser Gly Asn Ile Gly Thr Asn Tyr Val Gln
1               5                   10

<210> SEQ ID NO 110
<211> LENGTH: 11
<212> TYPE: PRT
<213> ORGANISM: Artificial Sequence
<220> FEATURE:
<223> OTHER INFORMATION: Light chain CDR1 of Ab-50

<400> SEQUENCE: 110

Gly Gly Asn Asn Ile Gly Ser Lys Gly Val His
1               5                   10

<210> SEQ ID NO 111
<211> LENGTH: 13
<212> TYPE: PRT
<213> ORGANISM: Artificial Sequence
<220> FEATURE:
<223> OTHER INFORMATION: Light chain CDR1 of Ab-52

<400> SEQUENCE: 111

Thr Arg Ser Ser Gly Ser Ile Ala Ser Asn Tyr Val Gln
1               5                   10

<210> SEQ ID NO 112
<211> LENGTH: 13
<212> TYPE: PRT
<213> ORGANISM: Artificial Sequence
<220> FEATURE:
<223> OTHER INFORMATION: Light chain CDR1 of Ab-55

<400> SEQUENCE: 112

Thr Arg Ser Ser Gly Ser Ile Ala Ser Asn Tyr Val Gln
1               5                   10

<210> SEQ ID NO 113
<211> LENGTH: 13
<212> TYPE: PRT
<213> ORGANISM: Artificial Sequence
<220> FEATURE:
<223> OTHER INFORMATION: Light chain CDR1 of Ab-56

<400> SEQUENCE: 113

Thr Arg Ser Ser Gly Ser Ile Ala Ser His Tyr Val Gln
1               5                   10

<210> SEQ ID NO 114
<211> LENGTH: 14
<212> TYPE: PRT
<213> ORGANISM: Artificial Sequence
<220> FEATURE:
<223> OTHER INFORMATION: Light chain CDR1 of Ab-65

<400> SEQUENCE: 114

Thr Leu Arg Ser Gly Leu Asn Val Gly Ser Tyr Arg Ile Tyr
1               5                   10

<210> SEQ ID NO 115
<211> LENGTH: 7
<212> TYPE: PRT
```

```
<213> ORGANISM: Artificial Sequence
<220> FEATURE:
<223> OTHER INFORMATION: Light chain CDR2 of consensus, Ab-14, Ab-42,
      Ab-52, Ab-55

<400> SEQUENCE: 115

Glu Asp Asn Gln Arg Pro Ser
1               5

<210> SEQ ID NO 116
<211> LENGTH: 7
<212> TYPE: PRT
<213> ORGANISM: Artificial Sequence
<220> FEATURE:
<223> OTHER INFORMATION: Light chain CDR2 of Ab-16

<400> SEQUENCE: 116

Gly Lys Asn Asn Arg Pro Ser
1               5

<210> SEQ ID NO 117
<211> LENGTH: 7
<212> TYPE: PRT
<213> ORGANISM: Artificial Sequence
<220> FEATURE:
<223> OTHER INFORMATION: Light chain CDR2 of Ab-22

<400> SEQUENCE: 117

Ser Asp Arg Asp Arg Pro Ser
1               5

<210> SEQ ID NO 118
<211> LENGTH: 7
<212> TYPE: PRT
<213> ORGANISM: Artificial Sequence
<220> FEATURE:
<223> OTHER INFORMATION: Light chain CDR2 of Ab-30

<400> SEQUENCE: 118

Asp Val Ser Asn Arg Pro Ser
1               5

<210> SEQ ID NO 119
<211> LENGTH: 7
<212> TYPE: PRT
<213> ORGANISM: Artificial Sequence
<220> FEATURE:
<223> OTHER INFORMATION: Light chain CDR2 of Ab-31

<400> SEQUENCE: 119

Gly Ala Ser Ser Arg Ala Thr
1               5

<210> SEQ ID NO 120
<211> LENGTH: 7
<212> TYPE: PRT
<213> ORGANISM: Artificial Sequence
<220> FEATURE:
<223> OTHER INFORMATION: Light chain CDR2 of Ab-32

<400> SEQUENCE: 120

Ala Ala Ser Thr Leu Gln Ser
1               5

<210> SEQ ID NO 121
<211> LENGTH: 7
<212> TYPE: PRT
```

<213> ORGANISM: Artificial Sequence
<220> FEATURE:
<223> OTHER INFORMATION: Light chain CDR2 of Ab-38

<400> SEQUENCE: 121

Gln Asp Ile Lys Arg Pro Ser
1               5

<210> SEQ ID NO 122
<211> LENGTH: 7
<212> TYPE: PRT
<213> ORGANISM: Artificial Sequence
<220> FEATURE:
<223> OTHER INFORMATION: Light chain CDR2 of Ab-46

<400> SEQUENCE: 122

Glu Asp Tyr Arg Arg Pro Ser
1               5

<210> SEQ ID NO 123
<211> LENGTH: 7
<212> TYPE: PRT
<213> ORGANISM: Artificial Sequence
<220> FEATURE:
<223> OTHER INFORMATION: Light chain CDR2 of Ab-50

<400> SEQUENCE: 123

Asp Asp Ser Asp Arg Pro Ser
1               5

<210> SEQ ID NO 124
<211> LENGTH: 7
<212> TYPE: PRT
<213> ORGANISM: Artificial Sequence
<220> FEATURE:
<223> OTHER INFORMATION: Light chain CDR2 of Ab-56

<400> SEQUENCE: 124

Glu Asp Asn Lys Arg Pro Ser
1               5

<210> SEQ ID NO 125
<211> LENGTH: 11
<212> TYPE: PRT
<213> ORGANISM: Artificial Sequence
<220> FEATURE:
<223> OTHER INFORMATION: Light chain CDR2 of Ab-65

<400> SEQUENCE: 125

Tyr Lys Ser Asp Ser Asn Lys Gln Gln Ala Ser
1               5                   10

<210> SEQ ID NO 126
<211> LENGTH: 9
<212> TYPE: PRT
<213> ORGANISM: Artificial Sequence
<220> FEATURE:
<223> OTHER INFORMATION: Light chain CDR3 consensus

<400> SEQUENCE: 126

Gln Ser Tyr Asp Ser Ser Thr Trp Val
1               5

<210> SEQ ID NO 127
<211> LENGTH: 10
<212> TYPE: PRT
<213> ORGANISM: Artificial Sequence

```
<220> FEATURE:
<223> OTHER INFORMATION: Light chain CDR3 of Ab-14

<400> SEQUENCE: 127

Gln Ser Tyr Asp Ser Ser Asn Leu Trp Val
1               5                   10

<210> SEQ ID NO 128
<211> LENGTH: 11
<212> TYPE: PRT
<213> ORGANISM: Artificial Sequence
<220> FEATURE:
<223> OTHER INFORMATION: Light chain CDR3 of Ab-16

<400> SEQUENCE: 128

Asn Ser Arg Asp Ser Ser Gly Asn His Tyr Val
1               5                   10

<210> SEQ ID NO 129
<211> LENGTH: 11
<212> TYPE: PRT
<213> ORGANISM: Artificial Sequence
<220> FEATURE:
<223> OTHER INFORMATION: Light chain CDR3 of Ab-22

<400> SEQUENCE: 129

Gln Val Trp Asp Asn Asn Ser Asp His Tyr Val
1               5                   10

<210> SEQ ID NO 130
<211> LENGTH: 9
<212> TYPE: PRT
<213> ORGANISM: Artificial Sequence
<220> FEATURE:
<223> OTHER INFORMATION: Light chain CDR3 of Ab-30

<400> SEQUENCE: 130

Ser Ser Tyr Thr Ser Ser Thr Leu Pro
1               5

<210> SEQ ID NO 131
<211> LENGTH: 9
<212> TYPE: PRT
<213> ORGANISM: Artificial Sequence
<220> FEATURE:
<223> OTHER INFORMATION: Light chain CDR3 of Ab-31

<400> SEQUENCE: 131

Gln Gln His Thr Ile Pro Thr Phe Ser
1               5

<210> SEQ ID NO 132
<211> LENGTH: 9
<212> TYPE: PRT
<213> ORGANISM: Artificial Sequence
<220> FEATURE:
<223> OTHER INFORMATION: Light chain CDR3 of Ab-32

<400> SEQUENCE: 132

Gln Gln Leu Asn Asn Tyr Pro Ile Thr
1               5

<210> SEQ ID NO 133
<211> LENGTH: 8
<212> TYPE: PRT
<213> ORGANISM: Artificial Sequence
<220> FEATURE:
```

-continued

<223> OTHER INFORMATION: Light chain CDR3 of Ab-38

<400> SEQUENCE: 133

Gln Thr Trp Asp Asn Ser Val Val
1               5

<210> SEQ ID NO 134
<211> LENGTH: 11
<212> TYPE: PRT
<213> ORGANISM: Artificial Sequence
<220> FEATURE:
<223> OTHER INFORMATION: Light chain CDR3 of Ab-42

<400> SEQUENCE: 134

Gln Ser Tyr Asp Ser Asn Asn Arg His Val Ile
1               5                   10

<210> SEQ ID NO 135
<211> LENGTH: 9
<212> TYPE: PRT
<213> ORGANISM: Artificial Sequence
<220> FEATURE:
<223> OTHER INFORMATION: Light chain CDR3 of Ab-46

<400> SEQUENCE: 135

Gln Ser Tyr His Ser Ser Gly Trp Glu
1               5

<210> SEQ ID NO 136
<211> LENGTH: 11
<212> TYPE: PRT
<213> ORGANISM: Artificial Sequence
<220> FEATURE:
<223> OTHER INFORMATION: Light chain CDR3 of Ab-50

<400> SEQUENCE: 136

Gln Val Trp Asp Ser Ser Ser Asp His Trp Val
1               5                   10

<210> SEQ ID NO 137
<211> LENGTH: 10
<212> TYPE: PRT
<213> ORGANISM: Artificial Sequence
<220> FEATURE:
<223> OTHER INFORMATION: Light chain CDR3 of Ab-52

<400> SEQUENCE: 137

Gln Ser Tyr Asp Ser Thr Thr Pro Ser Val
1               5                   10

<210> SEQ ID NO 138
<211> LENGTH: 9
<212> TYPE: PRT
<213> ORGANISM: Artificial Sequence
<220> FEATURE:
<223> OTHER INFORMATION: Light chain CDR3 of Ab-55

<400> SEQUENCE: 138

Gln Ser Tyr Asp Gly Ile Thr Val Ile
1               5

<210> SEQ ID NO 139
<211> LENGTH: 10
<212> TYPE: PRT
<213> ORGANISM: Artificial Sequence
<220> FEATURE:
<223> OTHER INFORMATION: Light chain CDR3 of Ab-56

```
<400> SEQUENCE: 139

Gln Ser Tyr Asp Ser Ser Asn Arg Trp Val
1               5                   10

<210> SEQ ID NO 140
<211> LENGTH: 9
<212> TYPE: PRT
<213> ORGANISM: Artificial Sequence
<220> FEATURE:
<223> OTHER INFORMATION: Light chain CDR3 of Ab-65

<400> SEQUENCE: 140

Met Ile Trp Tyr Ser Ser Ala Val Val
1               5
```